US010271719B2

(12) United States Patent
Morriss et al.

(10) Patent No.: US 10,271,719 B2
(45) Date of Patent: *Apr. 30, 2019

(54) PARANASAL OSTIUM FINDER DEVICES AND METHODS

(71) Applicant: Acclarent, Inc., Irvine, CA (US)

(72) Inventors: John H. Morriss, Emerald Hills, CA (US); Joshua Makower, Los Altos, CA (US); Carlos F. Fernandez, High Springs, FL (US); Eric Goldfarb, Belmont, CA (US); Thomas R. Jenkins, Alameda, CA (US)

(73) Assignee: Acclarent, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/625,013

(22) Filed: Jun. 16, 2017

(65) Prior Publication Data
US 2017/0347869 A1 Dec. 7, 2017

Related U.S. Application Data

(63) Continuation of application No. 14/446,537, filed on Jul. 30, 2014, now Pat. No. 9,750,401, which is a (Continued)

(51) Int. Cl.
*A61M 29/00* (2006.01)
*A61B 1/233* (2006.01)
(Continued)

(52) U.S. Cl.
CPC .............. *A61B 1/233* (2013.01); *A61B 17/24* (2013.01); *A61M 29/00* (2013.01);
(Continued)

(58) Field of Classification Search
CPC ... A61B 1/233; A61B 17/24; A61B 17/12104; A61B 17/12136; A61B 17/32;
(Continued)

(56) References Cited

U.S. PATENT DOCUMENTS

| 446,173 A | 2/1891 | Hancock |
| 504,424 A | 9/1893 | De Pezzer |

(Continued)

FOREIGN PATENT DOCUMENTS

| CH | 668188 | 12/1988 |
| CN | 2151720 | 1/1994 |

(Continued)

OTHER PUBLICATIONS

Argon Medical. Maxxim Medical. Ad for Sniper EliteTM Hydrophilic Ni—Ti Alloy Guidewire (2001).
(Continued)

*Primary Examiner* — Victor Nguyen
(74) *Attorney, Agent, or Firm* — Frost Brown Todd LLC

(57) ABSTRACT

Devices and methods for locating sinus ostia and positioning a guide wire within the sinus ostia. The subject devices comprise a shaft having a distal end, a proximal end, a curved region located between the distal and proximal ends, and an interior channel, an extensible and retractable guide wire movably mounted within the interior channel and a probe tip joined to the guide wire. Certain devices further include expandable portions for engaging and treating body anatomy.

17 Claims, 22 Drawing Sheets

Related U.S. Application Data continuation of application No. 12/512,420, filed on Jul. 30, 2009, now Pat. No. 8,979,888.

(60) Provisional application No. 61/084,965, filed on Jul. 30, 2008.

(51) Int. Cl.
  *A61B 17/24* (2006.01)
  *A61B 17/22* (2006.01)
  *A61B 17/32* (2006.01)
  *A61M 25/10* (2013.01)
  *A61M 29/02* (2006.01)

(52) U.S. Cl.
  CPC ............ *A61B 2017/22042* (2013.01); *A61B 2017/22051* (2013.01); *A61B 2017/320048* (2013.01); *A61M 25/1002* (2013.01); *A61M 2029/025* (2013.01)

(58) Field of Classification Search
  CPC .......... A61B 17/22; A61B 2017/22042; A61B 2017/22051; A61B 2017/320048; A61M 29/00; A61M 2029/025
  See application file for complete search history.

(56) References Cited

U.S. PATENT DOCUMENTS

| | | |
|---|---|---|
| 513,667 A | 1/1894 | Buckingham |
| 705,346 A | 7/1902 | Hamilton |
| 798,775 A | 9/1905 | Forsyte |
| 816,792 A | 4/1906 | Green |
| 1,080,934 A | 12/1913 | Shackleford |
| 1,200,267 A | 10/1916 | Sunnergren |
| 1,650,959 A | 11/1927 | Pitman |
| 1,735,519 A | 11/1929 | Vance |
| 1,828,986 A | 10/1931 | Stevens |
| 1,878,671 A | 9/1932 | Cantor |
| 2,201,749 A | 5/1940 | Vandegrift |
| 2,493,326 A | 1/1950 | Trinder |
| 2,525,183 A | 10/1950 | Robison |
| 2,847,997 A | 8/1958 | Tibone |
| 2,899,227 A | 8/1959 | Jeanrenaud |
| 2,906,179 A | 9/1959 | Bower |
| 2,995,832 A | 8/1961 | Alderson |
| 3,009,265 A | 11/1961 | Bexark |
| 3,037,286 A | 6/1962 | Bower |
| 3,173,418 A | 3/1965 | Baran |
| 3,347,061 A | 10/1967 | Stuemky |
| 3,376,659 A | 4/1968 | Asin et al. |
| 3,384,970 A | 5/1968 | Avalear |
| 3,393,073 A | 7/1968 | Reutenauer et al. |
| 3,435,826 A | 4/1969 | Fogarty |
| 3,469,578 A | 9/1969 | Bierman |
| 3,481,043 A | 12/1969 | Esch |
| 3,486,539 A | 12/1969 | Jacuzzi |
| 3,506,005 A | 4/1970 | Gilio et al. |
| 3,509,638 A | 5/1970 | Macleod |
| 3,515,888 A | 6/1970 | Lewis |
| 3,527,220 A | 9/1970 | Summers |
| 3,531,868 A | 10/1970 | Stevenson |
| 3,552,384 A | 1/1971 | Pierie et al. |
| 3,624,661 A | 11/1971 | Shebanow |
| 3,731,963 A | 5/1973 | Pond |
| 3,792,391 A | 2/1974 | Ewing |
| 3,800,788 A | 4/1974 | White |
| 3,802,096 A | 4/1974 | Matern |
| 3,804,081 A | 4/1974 | Kinoshita |
| 3,834,394 A | 9/1974 | Hunter et al. |
| 3,850,176 A | 11/1974 | Gottschalk |
| 3,856,000 A | 12/1974 | Chikama |
| 3,859,993 A | 1/1975 | Bitner |
| 3,871,365 A | 3/1975 | Chikama |
| 3,894,538 A | 7/1975 | Richter |
| 3,903,893 A | 9/1975 | Scheer |
| 3,910,617 A | 10/1975 | Scalza et al. |
| 3,921,636 A | 11/1975 | Zaffaroni |
| 3,948,254 A | 4/1976 | Zaffaroni |
| 3,948,262 A | 4/1976 | Zaffaroni |
| 3,967,618 A | 7/1976 | Zaffaroni |
| 3,993,069 A | 11/1976 | Buckles et al. |
| 3,993,072 A | 11/1976 | Zaffaroni |
| 3,993,073 A | 11/1976 | Zaffaroni |
| 4,016,251 A | 4/1977 | Higuchi et al. |
| 4,052,505 A | 10/1977 | Higuchi et al. |
| 4,053,975 A | 10/1977 | Olbrich et al. |
| 4,069,307 A | 1/1978 | Higuchi et al. |
| 4,102,342 A | 7/1978 | Akiyama et al. |
| 4,138,151 A | 2/1979 | Nakao |
| 4,184,497 A | 1/1980 | Kolff et al. |
| 4,198,766 A | 4/1980 | Camin et al. |
| 4,207,890 A | 6/1980 | Mamajek et al. |
| 4,209,919 A | 7/1980 | Kirikae et al. |
| 4,213,095 A | 7/1980 | Falconer |
| 4,217,898 A | 8/1980 | Theeuwes |
| 4,268,115 A | 5/1981 | Slemon et al. |
| 4,299,226 A | 11/1981 | Banka |
| 4,299,227 A | 11/1981 | Lincoff |
| 4,312,353 A | 1/1982 | Shahbabian |
| 4,338,941 A | 7/1982 | Payton |
| D269,204 S | 5/1983 | Trepp |
| 4,388,941 A | 6/1983 | Riedhammer |
| RE31,351 E | 8/1983 | Falconer |
| 4,435,716 A | 3/1984 | Zandbergen |
| 4,437,856 A | 3/1984 | Valli |
| 4,450,150 A | 5/1984 | Sidman |
| 4,459,977 A | 7/1984 | Pizon et al. |
| 4,464,175 A | 8/1984 | Altman et al. |
| 4,471,779 A | 9/1984 | Antoshkiw et al. |
| 4,499,899 A | 2/1985 | Lyons, III |
| 4,554,929 A | 11/1985 | Samson et al. |
| 4,564,364 A | 1/1986 | Zaffaroni et al. |
| 4,571,239 A | 2/1986 | Heyman |
| 4,571,240 A | 2/1986 | Samson et al. |
| 4,581,017 A | 4/1986 | Sahota |
| 4,585,000 A | 4/1986 | Hershenson |
| D283,921 S | 5/1986 | Dyak |
| 4,589,868 A | 5/1986 | Dretler |
| 4,596,528 A | 6/1986 | Lewis et al. |
| D284,892 S | 7/1986 | Glassman |
| 4,603,564 A | 8/1986 | Kleinhany et al. |
| 4,606,346 A | 8/1986 | Berg et al. |
| 4,607,622 A | 8/1986 | Fritch et al. |
| 4,637,389 A | 1/1987 | Heyden |
| 4,639,244 A | 1/1987 | Rizk et al. |
| 4,645,495 A | 2/1987 | Vaillancourt |
| 4,669,469 A | 6/1987 | Gifford, III |
| 4,672,961 A | 6/1987 | Davies |
| 4,675,613 A | 6/1987 | Naegeli et al. |
| 4,691,948 A | 9/1987 | Austin, Jr. et al. |
| 4,708,434 A | 11/1987 | Tsuno |
| 4,708,834 A | 11/1987 | Cohen et al. |
| 4,726,772 A | 2/1988 | Amplatz |
| 4,736,970 A | 4/1988 | McGourty et al. |
| 4,737,141 A | 4/1988 | Spits |
| 4,748,869 A | 6/1988 | Ohtsuka |
| 4,748,969 A | 6/1988 | Wardle |
| 4,748,986 A | 6/1988 | Morrison et al. |
| 4,755,171 A | 7/1988 | Tennant |
| 4,771,776 A | 9/1988 | Powell et al. |
| 4,793,359 A | 12/1988 | Sharrow |
| 4,795,439 A | 1/1989 | Guest |
| 4,796,629 A | 1/1989 | Grayzel |
| 4,803,076 A | 2/1989 | Ranade |
| 4,811,743 A | 3/1989 | Stevens |
| 4,815,478 A | 3/1989 | Buchbinder et al. |
| 4,819,619 A | 4/1989 | Augustine et al. |
| 4,846,186 A | 7/1989 | Box et al. |
| 4,847,258 A | 7/1989 | Sturm et al. |
| 4,851,228 A | 7/1989 | Zentner et al. |
| 4,854,330 A | 8/1989 | Evans, III et al. |
| 4,862,874 A | 9/1989 | Kellner |
| 4,867,138 A | 9/1989 | Kubota et al. |

(56) References Cited

U.S. PATENT DOCUMENTS

| | | |
|---|---|---|
| 4,883,465 A | 11/1989 | Brennan |
| 4,897,651 A | 1/1990 | DeMonte |
| 4,898,577 A | 2/1990 | Badger et al. |
| 4,917,419 A | 4/1990 | Mora, Jr. et al. |
| 4,917,667 A | 4/1990 | Jackson |
| 4,919,112 A | 4/1990 | Siegmund |
| 4,920,967 A | 5/1990 | Cottonaro et al. |
| 4,925,445 A | 5/1990 | Sakamoto et al. |
| 4,940,062 A | 7/1990 | Hampton et al. |
| 4,943,275 A | 7/1990 | Stricker |
| 4,946,466 A | 8/1990 | Pinchuk et al. |
| 4,961,433 A | 10/1990 | Christian |
| 4,966,163 A | 10/1990 | Kraus et al. |
| 4,968,300 A | 11/1990 | Moutafis et al. |
| 4,984,581 A | 1/1991 | Stice |
| 4,994,033 A | 2/1991 | Shockey et al. |
| 4,998,916 A | 3/1991 | Hammerslag et al. |
| 4,998,917 A | 3/1991 | Gaiser et al. |
| 5,001,825 A | 3/1991 | Halpern |
| 5,002,322 A | 3/1991 | Fukumoto |
| 5,019,075 A | 5/1991 | Spears et al. |
| 5,019,372 A | 5/1991 | Folkman et al. |
| 5,020,514 A | 6/1991 | Heckele |
| 5,021,043 A | 6/1991 | Becker et al. |
| 5,024,650 A | 6/1991 | Hagiwara et al. |
| 5,024,658 A | 6/1991 | Kozlov et al. |
| 5,026,384 A | 6/1991 | Farr et al. |
| 5,030,227 A | 7/1991 | Rosenbluth et al. |
| 5,041,089 A | 8/1991 | Mueller et al. |
| 5,044,678 A | 9/1991 | Detweiler |
| 5,053,007 A | 10/1991 | Euteneuer |
| 5,055,051 A | 10/1991 | Duncan |
| 5,060,660 A | 10/1991 | Gamble et al. |
| 5,067,489 A | 11/1991 | Lind |
| 5,069,226 A | 12/1991 | Tamauchi et al. |
| 5,087,244 A | 2/1992 | Wolinsky et al. |
| 5,087,246 A | 2/1992 | Smith |
| 5,090,595 A | 2/1992 | Vandeninck |
| 5,090,910 A | 2/1992 | Narlo |
| 5,112,228 A | 5/1992 | Zouras |
| 5,116,311 A | 5/1992 | Lofstedt |
| 5,127,393 A | 7/1992 | McFarlin et al. |
| 5,137,517 A | 8/1992 | Loney et al. |
| 5,139,510 A | 8/1992 | Goldsmith, III et al. |
| 5,139,832 A | 8/1992 | Hayashi et al. |
| D329,496 S | 9/1992 | Wotton |
| 5,152,747 A | 10/1992 | Oliver |
| 5,156,595 A | 10/1992 | Adams |
| 5,163,989 A | 11/1992 | Campbell et al. |
| 5,167,220 A | 12/1992 | Brown |
| 5,168,864 A | 12/1992 | Skockey |
| 5,169,043 A | 12/1992 | Catania |
| 5,169,386 A | 12/1992 | Becker et al. |
| 5,171,233 A | 12/1992 | Amplatz et al. |
| 5,180,368 A | 1/1993 | Garrison |
| 5,183,470 A | 2/1993 | Wettermann |
| 5,189,110 A | 2/1993 | Ikematu et al. |
| 5,195,168 A | 3/1993 | Yong |
| 5,197,457 A | 3/1993 | Adair |
| 5,207,695 A | 5/1993 | Trout, III |
| 5,211,952 A | 5/1993 | Spicer et al. |
| 5,215,105 A | 6/1993 | Kizelshteyn et al. |
| 5,221,260 A | 6/1993 | Burns et al. |
| 5,226,302 A | 7/1993 | Anderson |
| 5,230,348 A | 7/1993 | Ishibe et al. |
| 5,236,422 A | 8/1993 | Eplett, Jr. |
| 5,243,996 A | 9/1993 | Hall |
| D340,111 S | 10/1993 | Yoshikawa |
| 5,250,059 A | 10/1993 | Andreas et al. |
| 5,251,092 A | 10/1993 | Brady et al. |
| 5,252,183 A | 10/1993 | Shaban et al. |
| 5,255,679 A | 10/1993 | Imran |
| 5,256,144 A | 10/1993 | Kraus et al. |
| 5,263,926 A | 11/1993 | Wilk |
| 5,264,260 A | 11/1993 | Saab |
| 5,267,965 A | 12/1993 | Deniega |
| 5,270,086 A | 12/1993 | Hamlin |
| 5,273,052 A | 12/1993 | Kraus et al. |
| 5,275,593 A | 1/1994 | Easley et al. |
| 5,286,254 A | 2/1994 | Shapland et al. |
| 5,290,310 A | 3/1994 | Makower et al. |
| 5,295,694 A | 3/1994 | Levin |
| 5,300,085 A | 4/1994 | Yock |
| 5,304,123 A | 4/1994 | Atala et al. |
| 5,308,326 A | 5/1994 | Zimmon |
| 5,313,967 A | 5/1994 | Lieber et al. |
| 5,314,417 A | 5/1994 | Stephens et al. |
| 5,315,618 A | 5/1994 | Yoshida |
| 5,324,306 A | 6/1994 | Makower et al. |
| 5,333,620 A | 8/1994 | Moutafis et al. |
| 5,334,167 A | 8/1994 | Cocanower |
| 5,336,163 A | 8/1994 | DeMane et al. |
| 5,341,818 A | 8/1994 | Abrams et al. |
| 5,342,296 A | 8/1994 | Persson et al. |
| 5,343,865 A | 9/1994 | Gardineer et al. |
| 5,345,945 A | 9/1994 | Hodgson et al. |
| 5,346,075 A | 9/1994 | Nichols et al. |
| 5,346,508 A | 9/1994 | Hastings |
| 5,348,537 A | 9/1994 | Wiesner et al. |
| 5,350,396 A | 9/1994 | Eliachar |
| 5,356,418 A | 10/1994 | Shturman |
| 5,368,049 A | 11/1994 | Raman et al. |
| 5,368,558 A | 11/1994 | Nita |
| 5,368,566 A | 11/1994 | Crocker |
| 5,372,138 A | 12/1994 | Crowley et al. |
| 5,372,584 A | 12/1994 | Zink et al. |
| D355,031 S | 1/1995 | Yoshikawa |
| 5,386,817 A | 2/1995 | Jones |
| 5,391,147 A | 2/1995 | Imran et al. |
| 5,391,179 A | 2/1995 | Mezzoli |
| 5,402,799 A | 4/1995 | Colon et al. |
| 5,409,444 A | 4/1995 | Kensey |
| 5,411,475 A | 5/1995 | Atala et al. |
| 5,411,476 A | 5/1995 | Abrams et al. |
| 5,411,477 A | 5/1995 | Saab |
| 5,415,633 A | 5/1995 | Lazarus |
| 5,425,370 A | 6/1995 | Vilkomerson |
| 5,439,446 A | 8/1995 | Barry |
| 5,441,494 A | 8/1995 | Ortiz |
| 5,441,497 A | 8/1995 | Narciso, Jr. |
| 5,450,853 A | 9/1995 | Hastings et al. |
| 5,451,221 A | 9/1995 | Cho et al. |
| 5,454,817 A | 10/1995 | Katz |
| 5,458,572 A | 10/1995 | Campbell et al. |
| 5,465,717 A | 11/1995 | Imran et al. |
| 5,465,733 A | 11/1995 | Hinohara et al. |
| 5,478,565 A | 12/1995 | Geria |
| 5,486,181 A | 1/1996 | Cohen et al. |
| 5,496,338 A | 3/1996 | Miyagi et al. |
| 5,497,783 A | 3/1996 | Urick et al. |
| 5,507,301 A | 4/1996 | Wasicek et al. |
| 5,507,725 A | 4/1996 | Savage et al. |
| 5,507,766 A | 4/1996 | Kugo et al. |
| 5,512,055 A | 4/1996 | Domb et al. |
| 5,514,128 A | 5/1996 | Hillsman et al. |
| 5,519,532 A | 5/1996 | Broome |
| 5,531,676 A | 7/1996 | Edwards et al. |
| 5,533,985 A | 7/1996 | Wong |
| 5,538,008 A | 7/1996 | Crowe |
| 5,546,964 A | 8/1996 | Stangerup |
| 5,549,542 A | 8/1996 | Kovalcheck |
| 5,558,073 A | 9/1996 | Pomeranz et al. |
| 5,558,652 A | 9/1996 | Henke |
| 5,562,619 A | 10/1996 | Mirarchi et al. |
| 5,568,809 A | 10/1996 | Ben-Haim |
| 5,571,086 A | 11/1996 | Kaplan et al. |
| 5,578,007 A | 11/1996 | Imran |
| 5,578,048 A | 11/1996 | Pasqualucci et al. |
| 5,584,827 A | 12/1996 | Korteweg et al. |
| 5,591,194 A | 1/1997 | Berthiaume |
| 5,599,284 A | 2/1997 | Shea |
| 5,599,304 A | 2/1997 | Shaari |
| 5,599,576 A | 2/1997 | Opolski |
| 5,601,087 A | 2/1997 | Gunderson et al. |

(56) References Cited

U.S. PATENT DOCUMENTS

| | | |
|---|---|---|
| 5,601,594 A | 2/1997 | Best |
| 5,607,386 A | 3/1997 | Flam |
| 5,617,870 A | 4/1997 | Hastings et al. |
| 5,626,374 A | 5/1997 | Kim |
| 5,633,000 A | 5/1997 | Grossman et al. |
| 5,634,908 A | 6/1997 | Loomas |
| 5,638,819 A | 6/1997 | Manwaring et al. |
| 5,643,251 A | 7/1997 | Hillsman et al. |
| 5,645,789 A | 7/1997 | Roucher, Jr. |
| 5,647,361 A | 7/1997 | Damadian |
| 5,656,030 A | 8/1997 | Hunjan et al. |
| 5,662,674 A | 9/1997 | Debbas |
| 5,664,567 A | 9/1997 | Linder |
| 5,664,580 A | 9/1997 | Erickson et al. |
| 5,665,052 A | 9/1997 | Bullard |
| 5,669,388 A | 9/1997 | Vilkomerson |
| 5,673,707 A | 10/1997 | Chandrasekaran |
| 5,676,673 A | 10/1997 | Ferre et al. |
| 5,679,400 A | 10/1997 | Tuch |
| 5,682,199 A | 10/1997 | Lankford |
| 5,685,838 A | 11/1997 | Peters et al. |
| 5,685,847 A | 11/1997 | Barry |
| 5,690,373 A | 11/1997 | Luker |
| 5,693,065 A | 12/1997 | Rains, III |
| 5,694,945 A | 12/1997 | Ben-Haim |
| 5,697,159 A | 12/1997 | Linden |
| 5,700,286 A | 12/1997 | Tartaglia et al. |
| 5,707,389 A | 1/1998 | Louw et al. |
| 5,708,175 A | 1/1998 | Loyanagi et al. |
| 5,711,315 A | 1/1998 | Jerusalmy |
| 5,713,839 A | 2/1998 | Shea |
| 5,713,946 A | 2/1998 | Ben-Haim |
| 5,718,702 A | 2/1998 | Edwards |
| 5,720,300 A | 2/1998 | Fagan et al. |
| 5,722,401 A | 3/1998 | Pietroski et al. |
| 5,722,984 A | 3/1998 | Fischell et al. |
| 5,729,129 A | 3/1998 | Acker |
| 5,730,128 A | 3/1998 | Pomeranz et al. |
| 5,733,248 A | 3/1998 | Adams et al. |
| 5,746,755 A * | 5/1998 | Wood ............... A61B 17/00491 606/144 |
| 5,752,513 A | 5/1998 | Acker et al. |
| 5,762,604 A | 6/1998 | Kieturakis |
| 5,766,158 A | 6/1998 | Opolski |
| 5,775,327 A | 7/1998 | Randolph et al. |
| 5,776,158 A | 7/1998 | Chou |
| 5,779,699 A | 7/1998 | Lipson |
| 5,789,391 A | 8/1998 | Jacobus et al. |
| 5,792,100 A | 8/1998 | Shantha |
| 5,797,878 A | 8/1998 | Bleam |
| 5,803,089 A | 9/1998 | Ferre et al. |
| 5,814,016 A | 9/1998 | Valley et al. |
| 5,819,723 A | 10/1998 | Joseph |
| 5,820,568 A | 10/1998 | Willis |
| 5,820,592 A | 10/1998 | Hammerslag |
| 5,824,044 A | 10/1998 | Quiachon et al. |
| 5,824,048 A | 10/1998 | Tuch |
| 5,824,173 A | 10/1998 | Fontirroche et al. |
| 5,826,576 A | 10/1998 | West |
| 5,827,224 A | 10/1998 | Shippert |
| 5,830,188 A | 11/1998 | Abouleish |
| 5,833,608 A | 11/1998 | Acker |
| 5,833,645 A | 11/1998 | Lieber et al. |
| 5,833,650 A | 11/1998 | Imran |
| 5,833,682 A | 11/1998 | Amplatz et al. |
| 5,836,638 A | 11/1998 | Slocum |
| 5,836,935 A | 11/1998 | Ashton et al. |
| 5,837,313 A | 11/1998 | Ding et al. |
| 5,843,089 A | 12/1998 | Shatjian et al. |
| 5,843,113 A | 12/1998 | High |
| 5,846,259 A | 12/1998 | Berthiaume |
| 5,857,998 A | 1/1999 | Barry |
| 5,862,693 A | 1/1999 | Myers et al. |
| 5,865,767 A | 2/1999 | Frechette et al. |
| 5,872,879 A | 2/1999 | Hamm |
| 5,873,835 A | 2/1999 | Hastings |
| 5,882,333 A | 3/1999 | Schaer et al. |
| 5,887,467 A | 3/1999 | Butterweck et al. |
| 5,902,247 A | 5/1999 | Coe et al. |
| 5,902,333 A | 5/1999 | Roberts et al. |
| 5,904,701 A | 5/1999 | Daneshvar |
| 5,908,407 A | 6/1999 | Frazee et al. |
| 5,916,193 A | 6/1999 | Stevens et al. |
| 5,928,192 A | 7/1999 | Maahs |
| 5,931,811 A | 8/1999 | Haissaguerre et al. |
| 5,931,818 A | 8/1999 | Werp et al. |
| 5,932,035 A | 8/1999 | Koger et al. |
| 5,935,061 A | 8/1999 | Acker et al. |
| 5,941,816 A | 8/1999 | Barthel et al. |
| D413,629 S | 9/1999 | Wolff et al. |
| 5,947,988 A | 9/1999 | Smith |
| 5,949,929 A | 9/1999 | Hamm |
| 5,954,693 A | 9/1999 | Barry |
| 5,954,694 A | 9/1999 | Sunseri |
| 5,957,842 A | 9/1999 | Littmann et al. |
| 5,968,085 A | 10/1999 | Morris et al. |
| 5,971,975 A | 10/1999 | Mills et al. |
| 5,979,290 A | 11/1999 | Simeone |
| 5,980,503 A | 11/1999 | Chin |
| 5,980,551 A | 11/1999 | Summers et al. |
| 5,984,945 A | 11/1999 | Sirhan |
| 5,985,307 A | 11/1999 | Hanson et al. |
| 5,987,344 A | 11/1999 | West |
| 5,997,562 A | 12/1999 | Zadno-Azizi et al. |
| 6,006,126 A | 12/1999 | Cosman |
| 6,006,130 A | 12/1999 | Higo et al. |
| 6,007,516 A | 12/1999 | Burbank et al. |
| 6,007,991 A | 12/1999 | Sivaraman et al. |
| 6,010,511 A | 1/2000 | Murphy |
| 6,013,019 A | 1/2000 | Fischell et al. |
| 6,015,414 A | 1/2000 | Werp et al. |
| 6,016,429 A | 1/2000 | Khafizov et al. |
| 6,016,439 A | 1/2000 | Acker |
| 6,019,736 A | 2/2000 | Avellanet et al. |
| 6,019,777 A | 2/2000 | Mackenzie |
| 6,021,340 A | 2/2000 | Randolph et al. |
| 6,022,313 A | 2/2000 | Ginn et al. |
| 6,027,461 A | 2/2000 | Walker et al. |
| 6,027,478 A | 2/2000 | Katz |
| 6,039,699 A | 3/2000 | Viera |
| 6,042,561 A | 3/2000 | Ash et al. |
| 6,048,299 A | 4/2000 | von Hoffmann |
| 6,048,358 A | 4/2000 | Barak |
| 6,053,172 A | 4/2000 | Hovda et al. |
| 6,056,702 A | 5/2000 | Lorenzo |
| 6,059,752 A | 5/2000 | Segal |
| 6,071,233 A | 6/2000 | Ishikawa et al. |
| 6,079,755 A | 6/2000 | Chang |
| 6,080,190 A | 6/2000 | Schwartz |
| 6,083,148 A | 7/2000 | Williams |
| 6,083,188 A | 7/2000 | Becker et al. |
| 6,086,585 A | 7/2000 | Hovda et al. |
| 6,092,846 A | 7/2000 | Fuss et al. |
| 6,093,150 A | 7/2000 | Chandler et al. |
| 6,093,195 A | 7/2000 | Ouchi |
| 6,109,268 A | 8/2000 | Thapliyal et al. |
| 6,113,567 A | 9/2000 | becker |
| 6,117,105 A | 9/2000 | Bresnaham et al. |
| 6,122,541 A | 9/2000 | Cosman et al. |
| 6,123,697 A | 9/2000 | Shippert |
| 6,136,006 A | 10/2000 | Johnson et al. |
| 6,139,510 A | 10/2000 | Palermo |
| 6,142,957 A | 11/2000 | Diamond et al. |
| 6,148,823 A | 11/2000 | Hastings |
| 6,149,213 A | 11/2000 | Sokurenko et al. |
| 6,159,170 A | 12/2000 | Borodulin et al. |
| 6,171,298 B1 | 1/2001 | Matsuura et al. |
| 6,171,303 B1 | 1/2001 | Ben-Haim |
| 6,174,280 B1 | 1/2001 | Oneda et al. |
| 6,176,829 B1 | 1/2001 | Vilkomerson |
| 6,179,788 B1 | 1/2001 | Sullivan |
| 6,179,811 B1 | 1/2001 | Fugoso et al. |
| 6,183,461 B1 | 2/2001 | Matsuura et al. |
| 6,183,464 B1 | 2/2001 | Sharp et al. |

(56) References Cited

U.S. PATENT DOCUMENTS

| | | |
|---|---|---|
| 6,190,353 B1 | 2/2001 | Makower et al. |
| 6,190,381 B1 | 2/2001 | Olsen et al. |
| 6,193,650 B1 | 2/2001 | Ryan, Jr. |
| 6,195,225 B1 | 2/2001 | Komatsu et al. |
| 6,200,257 B1 | 3/2001 | Winkler |
| 6,206,870 B1 | 3/2001 | Kanner |
| 6,213,975 B1 | 4/2001 | Laksin |
| 6,221,042 B1 | 4/2001 | Adams |
| 6,231,543 B1 | 5/2001 | Hedge et al. |
| 6,234,958 B1 | 5/2001 | Snoke et al. |
| 6,238,364 B1 | 5/2001 | Becker |
| 6,238,391 B1 | 5/2001 | Olsen et al. |
| 6,241,519 B1 | 6/2001 | Sedleemayer |
| 6,249,180 B1 | 6/2001 | Maalej et al. |
| 6,254,550 B1 | 7/2001 | McNamara et al. |
| 6,268,574 B1 | 7/2001 | Edens |
| 6,293,957 B1 | 9/2001 | Peters et al. |
| 6,302,875 B1 | 10/2001 | Makower et al. |
| 6,306,105 B1 | 10/2001 | Rooney et al. |
| 6,306,124 B1 | 10/2001 | Jones et al. |
| D450,382 S | 11/2001 | Nestenborg |
| 6,322,495 B1 | 11/2001 | Snow et al. |
| 6,328,564 B1 | 12/2001 | Thurow |
| 6,332,089 B1 | 12/2001 | Acker et al. |
| 6,332,891 B1 | 12/2001 | Himes |
| 6,340,360 B1 | 1/2002 | Lyles et al. |
| 6,348,041 B1 | 2/2002 | Klint |
| 6,352,503 B1 | 3/2002 | Matsui et al. |
| 6,375,615 B1 | 4/2002 | Flaherty et al. |
| 6,375,629 B1 | 4/2002 | Muni et al. |
| 6,383,146 B1 | 5/2002 | Klint |
| 6,386,197 B1 | 5/2002 | Miller |
| 6,389,313 B1 | 5/2002 | Marchitto et al. |
| 6,390,993 B1 | 5/2002 | Cornish et al. |
| 6,394,093 B1 | 5/2002 | Lethi |
| 6,398,758 B1 | 6/2002 | Jacobsen et al. |
| 6,409,863 B1 | 6/2002 | Williams et al. |
| 6,423,012 B1 | 7/2002 | Kato et al. |
| 6,425,877 B1 | 7/2002 | Edwards |
| 6,432,986 B2 | 8/2002 | Levin |
| 6,440,061 B1 | 8/2002 | Wenner et al. |
| 6,443,947 B1 | 9/2002 | Marko et al. |
| 6,445,939 B1 | 9/2002 | Swanson et al. |
| 6,450,975 B1 | 9/2002 | Brennan et al. |
| 6,450,989 B2 | 9/2002 | Dubrul et al. |
| 6,464,650 B2 | 10/2002 | Jafari et al. |
| 6,468,202 B1 | 10/2002 | Irion et al. |
| 6,468,297 B1 | 10/2002 | Williams et al. |
| 6,485,475 B1 | 11/2002 | Chelly |
| 6,491,940 B1 | 12/2002 | Levin |
| 6,494,894 B2 | 12/2002 | Mirarchi |
| 6,500,130 B2 | 12/2002 | Kinsella et al. |
| 6,500,189 B1 | 12/2002 | Lang et al. |
| 6,503,087 B1 | 1/2003 | Eggert et al. |
| 6,503,185 B1 | 1/2003 | Waksman et al. |
| 6,503,263 B2 | 1/2003 | Adams |
| 6,511,418 B2 | 1/2003 | Shahidi et al. |
| 6,511,471 B2 | 1/2003 | Rosenman et al. |
| 6,514,249 B1 | 2/2003 | Maguire et al. |
| 6,517,478 B2 | 2/2003 | Khadem |
| 6,524,129 B2 | 2/2003 | Cote et al. |
| 6,524,299 B1 | 2/2003 | Tran et al. |
| 6,526,302 B2 | 2/2003 | Hassett |
| 6,527,753 B2 | 3/2003 | Sekine et al. |
| 6,529,756 B1 | 3/2003 | Phan et al. |
| 6,533,754 B1 | 3/2003 | Hisamatsu et al. |
| 6,536,437 B1 | 3/2003 | Dragisic |
| 6,537,294 B1 | 3/2003 | Boyle et al. |
| 6,543,452 B1 | 4/2003 | Lavigne |
| 6,544,230 B1 | 4/2003 | Flaherty et al. |
| 6,549,800 B1 | 4/2003 | Atalar et al. |
| 6,551,239 B2 | 4/2003 | Renner et al. |
| 6,569,146 B1 | 5/2003 | Werner et al. |
| 6,569,147 B1 | 5/2003 | Evans et al. |
| 6,571,131 B1 | 5/2003 | Nguyen |
| 6,572,538 B2 | 6/2003 | Takase |
| 6,572,590 B1 | 6/2003 | Stevens et al. |
| 6,579,285 B2 | 6/2003 | Sinofsky |
| 6,585,639 B1 | 7/2003 | Kotmel et al. |
| 6,585,717 B1 | 7/2003 | Wittenberger et al. |
| 6,585,794 B2 | 7/2003 | Shimoda et al. |
| 6,589,237 B2 | 7/2003 | Woloszko et al. |
| 6,591,130 B2 | 7/2003 | Shahidi |
| 6,596,009 B1 | 7/2003 | Jelic |
| 6,607,546 B1 | 8/2003 | Murken |
| 6,612,999 B2 | 9/2003 | Brennan et al. |
| 6,613,066 B1 | 9/2003 | Fukaya et al. |
| 6,616,601 B2 | 9/2003 | Hayakawa |
| 6,616,659 B1 | 9/2003 | de la Torre et al. |
| 6,616,678 B2 | 9/2003 | Nishtala et al. |
| 6,616,913 B1 | 9/2003 | Mautone |
| 6,619,085 B1 | 9/2003 | Hsieh |
| 6,634,684 B2 | 10/2003 | Spiessl |
| 6,638,233 B2 | 10/2003 | Corvi et al. |
| 6,638,268 B2 | 10/2003 | Niazi |
| 6,638,291 B1 | 10/2003 | Ferrera et al. |
| 6,645,193 B2 | 11/2003 | Mangosong |
| 6,652,472 B2 | 11/2003 | Jafari et al. |
| 6,652,480 B1 | 11/2003 | Imran et al. |
| 6,656,166 B2 | 12/2003 | Lurie et al. |
| 6,663,589 B1 | 12/2003 | Halevy |
| 6,669,689 B2 | 12/2003 | Lehmann et al. |
| 6,669,711 B1 | 12/2003 | Noda |
| 6,672,773 B1 | 1/2004 | Glenn et al. |
| 6,673,025 B1 | 1/2004 | Richardson et al. |
| 6,679,871 B2 | 1/2004 | Hahnen |
| 6,685,648 B2 | 2/2004 | Flaherty et al. |
| 6,689,096 B1 | 2/2004 | Loubens et al. |
| 6,689,146 B1 | 2/2004 | Himes |
| 6,702,735 B2 | 3/2004 | Kelly |
| 6,712,757 B2 | 3/2004 | Becker et al. |
| 6,714,809 B2 | 3/2004 | Lee et al. |
| 6,716,183 B2 | 4/2004 | Clayman et al. |
| 6,716,216 B1 | 4/2004 | Boucher et al. |
| 6,716,813 B2 | 4/2004 | Lim et al. |
| 6,719,749 B1 | 4/2004 | Schweikert et al. |
| 6,719,763 B2 | 4/2004 | Chung et al. |
| 6,726,701 B2 | 4/2004 | Gilson et al. |
| 6,755,812 B2 | 6/2004 | Peterson et al. |
| 6,776,772 B1 | 8/2004 | de Vrijer et al. |
| 6,780,168 B2 | 8/2004 | Jellie |
| 6,783,522 B2 | 8/2004 | Fischell |
| 6,783,536 B2 | 8/2004 | Vilsmeier et al. |
| 6,786,864 B2 | 9/2004 | Matsuura et al. |
| 6,796,960 B2 | 9/2004 | Cioanta et al. |
| 6,811,544 B2 | 11/2004 | Schaer |
| 6,817,364 B2 | 11/2004 | Garibaldi et al. |
| 6,817,976 B2 | 11/2004 | Rovegno |
| 6,827,683 B2 | 12/2004 | Otawara |
| 6,827,701 B2 | 12/2004 | MacMahon et al. |
| 6,832,715 B2 | 12/2004 | Eungard et al. |
| D501,677 S | 2/2005 | Becker |
| 6,849,062 B2 | 2/2005 | Kantor |
| 6,851,290 B1 | 2/2005 | Meier et al. |
| 6,860,264 B2 | 3/2005 | Christopher |
| 6,860,849 B2 | 3/2005 | Matsushita et al. |
| 6,878,106 B1 | 4/2005 | Herrmann |
| 6,890,329 B2 | 5/2005 | Carroll et al. |
| 6,899,672 B2 | 5/2005 | Chin et al. |
| 6,902,556 B2 | 6/2005 | Grimes et al. |
| 6,913,763 B2 | 7/2005 | Lerner |
| 6,927,478 B2 | 8/2005 | Paek |
| 6,939,361 B1 | 9/2005 | Kleshinski |
| 6,939,374 B2 | 9/2005 | Banik et al. |
| 6,955,657 B1 | 10/2005 | Webler |
| 6,966,906 B2 | 11/2005 | Brown |
| 6,971,998 B2 | 12/2005 | Rosenman et al. |
| 6,979,290 B2 | 12/2005 | Mourlas et al. |
| 6,984,203 B2 | 1/2006 | Tartaglia et al. |
| 6,991,597 B2 | 1/2006 | Gellman et al. |
| 6,997,931 B2 | 2/2006 | Sauer et al. |
| 6,997,941 B2 | 2/2006 | Sharkey et al. |
| 7,004,173 B2 | 2/2006 | Sparks et al. |
| 7,008,412 B2 | 3/2006 | Maginot |

(56) References Cited

U.S. PATENT DOCUMENTS

| | | |
|---|---|---|
| 7,011,654 B2 | 3/2006 | Dubrul et al. |
| 7,022,105 B1 | 4/2006 | Edwards |
| 7,043,961 B2 | 5/2006 | Pandey |
| 7,048,711 B2 | 5/2006 | Rosenmann et al. |
| 7,052,474 B2 | 5/2006 | Castell et al. |
| 7,056,284 B2 | 6/2006 | Martone et al. |
| 7,056,303 B2 | 6/2006 | Dennis et al. |
| 7,056,314 B1 | 6/2006 | Florio et al. |
| 7,074,197 B2 | 7/2006 | Reynolds et al. |
| 7,074,426 B2 | 7/2006 | Kochinke |
| 7,097,612 B2 | 8/2006 | Bertolero et al. |
| 7,108,677 B2 | 9/2006 | Courtney et al. |
| 7,108,706 B2 | 9/2006 | Hogle |
| 7,117,039 B2 | 10/2006 | Manning et al. |
| 7,128,718 B2 | 10/2006 | Hojeibane et al. |
| 7,131,969 B1 | 11/2006 | Hovda et al. |
| 7,140,480 B2 | 11/2006 | Drussel et al. |
| D534,216 S | 12/2006 | Makower et al. |
| 7,160,255 B2 | 1/2007 | Saadat |
| 7,169,140 B1 | 1/2007 | Kume |
| 7,169,163 B2 | 1/2007 | Becker |
| 7,172,562 B2 | 2/2007 | McKinley |
| 7,174,774 B2 | 2/2007 | Pawar et al. |
| 7,182,735 B2 | 2/2007 | Shireman et al. |
| 7,184,827 B1 | 2/2007 | Edwards |
| 7,214,201 B2 | 5/2007 | Burmeister et al. |
| 7,233,820 B2 | 6/2007 | Gilboa |
| 7,235,099 B1 | 6/2007 | Duncavage et al. |
| 7,237,313 B2 | 7/2007 | Skujins et al. |
| 7,252,677 B2 | 8/2007 | Burwell et al. |
| 7,282,057 B2 | 10/2007 | Surti et al. |
| 7,294,345 B2 | 11/2007 | Haapakumpu et al. |
| 7,294,365 B2 | 11/2007 | Hayakawa et al. |
| 7,313,430 B2 | 12/2007 | Urquhart et al. |
| 7,316,168 B2 | 1/2008 | van der Knokke et al. |
| 7,316,656 B2 | 1/2008 | Shireman et al. |
| 7,318,831 B2 | 1/2008 | Alvarez et al. |
| 7,322,934 B2 | 1/2008 | Miyake et al. |
| 7,326,235 B2 | 2/2008 | Edwards |
| 7,338,467 B2 | 3/2008 | Lutter |
| 7,343,920 B2 | 3/2008 | Toby et al. |
| 7,359,755 B2 | 4/2008 | Jones et al. |
| 7,361,168 B2 | 4/2008 | Makower et al. |
| 7,366,562 B2 | 4/2008 | Dukesherer et al. |
| 7,371,210 B2 | 5/2008 | Brock et al. |
| 7,381,205 B2 | 6/2008 | Thommen |
| 7,410,480 B2 | 8/2008 | Muni et al. |
| 7,419,497 B2 | 9/2008 | Muni et al. |
| 7,438,701 B2 | 10/2008 | Theeuwes et al. |
| 7,442,191 B2 | 10/2008 | Hovda et al. |
| 7,452,351 B2 | 11/2008 | Miller et al. |
| 7,454,244 B2 | 11/2008 | Kassab et al. |
| 7,462,175 B2 | 12/2008 | Chang et al. |
| 7,471,994 B2 | 12/2008 | Ford et al. |
| 7,481,218 B2 | 1/2009 | Djupesland |
| 7,481,800 B2 | 1/2009 | Jacques |
| D586,465 S | 2/2009 | Faulkner et al. |
| D586,916 S | 2/2009 | Faulkner et al. |
| 7,488,313 B2 | 2/2009 | Segal et al. |
| 7,488,337 B2 | 2/2009 | Saab et al. |
| 7,493,156 B2 | 2/2009 | Manning et al. |
| 7,500,971 B2 | 3/2009 | Chang et al. |
| D590,502 S | 4/2009 | Geisser et al. |
| 7,520,876 B2 | 4/2009 | Ressemann et al. |
| 7,532,920 B1 | 5/2009 | Ainsworth et al. |
| 7,544,192 B2 | 6/2009 | Eaton et al. |
| 7,559,925 B2 | 7/2009 | Goldfarb et al. |
| 7,610,104 B2 | 10/2009 | Kaplan et al. |
| 7,615,005 B2 | 11/2009 | Stefanchik et al. |
| 7,618,450 B2 | 11/2009 | Zarowski et al. |
| 7,625,335 B2 | 12/2009 | Deichmann et al. |
| 7,632,291 B2 | 12/2009 | Stephens et al. |
| 7,634,233 B2 | 12/2009 | Deng et al. |
| 7,641,644 B2 | 1/2010 | Chang et al. |
| 7,641,668 B2 | 1/2010 | Perry et al. |
| 7,645,272 B2 | 1/2010 | Chang et al. |
| 7,648,367 B1 | 1/2010 | Makower et al. |
| 7,654,997 B2 | 2/2010 | Makower et al. |
| 7,680,244 B2 | 3/2010 | Gertner et al. |
| 7,686,798 B2 | 3/2010 | Eaton et al. |
| 7,691,120 B2 | 4/2010 | Shluzas et al. |
| 7,717,933 B2 | 5/2010 | Becker |
| 7,720,521 B2 | 5/2010 | Chang et al. |
| 7,727,186 B2 | 6/2010 | Makower et al. |
| 7,736,301 B1 | 6/2010 | Webler et al. |
| 7,740,642 B2 | 6/2010 | Becker |
| 7,753,929 B2 | 7/2010 | Becker |
| 7,753,930 B2 | 7/2010 | Becker |
| 7,771,409 B2 | 8/2010 | Chang et al. |
| 7,775,968 B2 | 8/2010 | Mathis |
| 7,799,048 B2 | 9/2010 | Hudson et al. |
| 7,803,150 B2 | 9/2010 | Chang et al. |
| 7,833,282 B2 | 11/2010 | Mandpe |
| 7,837,672 B2 | 11/2010 | Intoccia |
| 7,840,254 B2 | 11/2010 | Glossop |
| 7,854,744 B2 | 12/2010 | Becker |
| D630,321 S | 1/2011 | Hamilton, Jr. |
| 7,875,050 B2 | 1/2011 | Samson et al. |
| D632,791 S | 2/2011 | Murner |
| 7,883,717 B2 | 2/2011 | Varner et al. |
| 7,896,891 B2 | 3/2011 | Catanese, III et al. |
| 7,951,132 B2 | 5/2011 | Eaton et al. |
| 7,988,705 B2 | 8/2011 | Galdonik et al. |
| 7,993,353 B2 | 8/2011 | Roβner et al. |
| 8,002,740 B2 | 8/2011 | Willink et al. |
| 8,014,849 B2 | 9/2011 | Peckham |
| 8,016,752 B2 | 9/2011 | Armstrong et al. |
| 8,025,635 B2 | 9/2011 | Eaton et al. |
| 8,080,000 B2 | 12/2011 | Makower et al. |
| 8,088,063 B2 | 1/2012 | Fujikura et al. |
| 8,088,101 B2 | 1/2012 | Chang et al. |
| 8,090,433 B2 | 1/2012 | Makower et al. |
| 8,100,933 B2 | 1/2012 | Becker |
| 8,104,483 B2 | 1/2012 | Taylor |
| 8,114,062 B2 | 2/2012 | Muni et al. |
| 8,114,113 B2 | 2/2012 | Becker |
| 8,123,722 B2 | 2/2012 | Chang et al. |
| 8,142,422 B2 | 3/2012 | Makower et al. |
| 8,147,545 B2 | 4/2012 | Avior |
| 8,167,821 B2 | 5/2012 | Sharrow |
| 8,190,389 B2 | 5/2012 | Kim et al. |
| 8,197,433 B2 | 6/2012 | Cohen |
| 8,197,552 B2 | 6/2012 | Mandpe |
| 8,249,700 B2 | 8/2012 | Clifford et al. |
| 8,277,386 B2 | 10/2012 | Ahmed et al. |
| 8,282,667 B2 | 10/2012 | Drontle et al. |
| 8,317,816 B2 | 11/2012 | Becker |
| 8,337,454 B2 | 12/2012 | Eaton et al. |
| 8,388,642 B2 | 3/2013 | Muni et al. |
| 8,403,954 B2 | 3/2013 | Santin et al. |
| 8,439,687 B1 | 5/2013 | Morriss et al. |
| 8,535,707 B2 | 9/2013 | Arensdorf et al. |
| 8,864,778 B2 * | 10/2014 | Fortson ............. A61B 17/0057 606/139 |
| 2001/0004644 A1 | 6/2001 | Levin |
| 2001/0034530 A1 | 10/2001 | Malackowski et al. |
| 2002/0006961 A1 | 1/2002 | Katz et al. |
| 2002/0055746 A1 | 5/2002 | Burke et al. |
| 2002/0090388 A1 | 7/2002 | Humes et al. |
| 2003/0013985 A1 | 1/2003 | Saadat |
| 2003/0017111 A1 | 1/2003 | Rabito |
| 2003/0018291 A1 | 1/2003 | Hill et al. |
| 2003/0040697 A1 | 2/2003 | Pass et al. |
| 2003/0083608 A1 | 5/2003 | Evans et al. |
| 2003/0114732 A1 | 6/2003 | Webler et al. |
| 2003/0163154 A1 | 8/2003 | Miyata et al. |
| 2004/0015150 A1 | 1/2004 | Zadno-Azizi |
| 2004/0018980 A1 | 1/2004 | Gurney et al. |
| 2004/0034311 A1 | 2/2004 | Mihakcik |
| 2004/0043052 A1 | 3/2004 | Hunter et al. |
| 2004/0058992 A1 | 3/2004 | Marinello et al. |
| 2004/0064105 A1 | 4/2004 | Capes et al. |
| 2004/0116958 A1 | 6/2004 | Gopferich et al. |
| 2004/0127820 A1 | 7/2004 | Clayman et al. |

(56) References Cited

U.S. PATENT DOCUMENTS

| | | |
|---|---|---|
| 2004/0158229 A1 | 8/2004 | Quinn |
| 2004/0181175 A1 | 9/2004 | Clayman et al. |
| 2004/0193073 A1 | 9/2004 | DeMello et al. |
| 2004/0230156 A1 | 11/2004 | Schreck et al. |
| 2004/0236231 A1 | 11/2004 | Knighton et al. |
| 2004/0249243 A1 | 12/2004 | Kleiner |
| 2004/0267347 A1 | 12/2004 | Cervantes |
| 2005/0027249 A1 | 2/2005 | Reifart et al. |
| 2005/0055077 A1 | 3/2005 | Marco |
| 2005/0059931 A1 | 3/2005 | Garrison et al. |
| 2005/0089670 A1 | 4/2005 | Large |
| 2005/0107738 A1 | 5/2005 | Slater et al. |
| 2005/0113687 A1 | 5/2005 | Herweck et al. |
| 2005/0113850 A1 | 5/2005 | Tagge |
| 2005/0119590 A1 | 6/2005 | Burmeister et al. |
| 2005/0131316 A1 | 6/2005 | Flagle et al. |
| 2005/0143687 A1 | 6/2005 | Rosenblatt et al. |
| 2005/0182319 A1 | 8/2005 | Glossop |
| 2005/0234507 A1 | 10/2005 | Geske et al. |
| 2005/0244472 A1 | 11/2005 | Hughes et al. |
| 2005/0283221 A1 | 12/2005 | Mann et al. |
| 2006/0004323 A1 | 1/2006 | Chang et al. |
| 2006/0063973 A1 | 3/2006 | Makower et al. |
| 2006/0173382 A1 | 8/2006 | Schreiner |
| 2006/0190022 A1 | 8/2006 | Beyar et al. |
| 2006/0211752 A1 | 9/2006 | Kohn et al. |
| 2006/0271024 A1 | 11/2006 | Gertner et al. |
| 2007/0020196 A1 | 1/2007 | Pipkin et al. |
| 2007/0112358 A1 | 5/2007 | Abbott et al. |
| 2007/0129751 A1 | 6/2007 | Muni et al. |
| 2007/0135789 A1 | 6/2007 | Chang et al. |
| 2007/0167682 A1 | 7/2007 | Goldfarb et al. |
| 2007/0207186 A1 | 9/2007 | Scanlon et al. |
| 2007/0208252 A1 | 9/2007 | Makower |
| 2007/0208301 A1 | 9/2007 | Evard et al. |
| 2007/0249896 A1 | 10/2007 | Goldfarb et al. |
| 2007/0269385 A1 | 11/2007 | Yun et al. |
| 2007/0282305 A1 | 12/2007 | Goldfarb et al. |
| 2007/0293727 A1 | 12/2007 | Goldfarb et al. |
| 2007/0293946 A1 | 12/2007 | Gonzales et al. |
| 2008/0015544 A1 | 1/2008 | Keith et al. |
| 2008/0033519 A1 | 2/2008 | Burwell et al. |
| 2008/0051804 A1 | 2/2008 | Cottler et al. |
| 2008/0097516 A1 | 4/2008 | Chang et al. |
| 2008/0103521 A1 | 5/2008 | Makower et al. |
| 2008/0119693 A1 | 5/2008 | Makower et al. |
| 2008/0125626 A1 | 5/2008 | Chang et al. |
| 2008/0132938 A1 | 6/2008 | Chang et al. |
| 2008/0183128 A1 | 7/2008 | Morriss et al. |
| 2008/0188870 A1 | 8/2008 | Andre et al. |
| 2008/0195041 A1 | 8/2008 | Goldfarb et al. |
| 2008/0228085 A1 | 9/2008 | Jenkins et al. |
| 2008/0262508 A1 | 10/2008 | Clifford et al. |
| 2008/0275483 A1 | 11/2008 | Makower et al. |
| 2008/0281156 A1 | 11/2008 | Makower et al. |
| 2008/0287908 A1 | 11/2008 | Muni et al. |
| 2008/0319424 A1 | 12/2008 | Muni et al. |
| 2009/0030274 A1 | 1/2009 | Goldfarb et al. |
| 2009/0088728 A1 | 4/2009 | Dollar et al. |
| 2009/0156980 A1 | 6/2009 | Eaton et al. |
| 2009/0163890 A1 | 6/2009 | Clifford et al. |
| 2009/0187089 A1 | 7/2009 | Say et al. |
| 2009/0187098 A1 | 7/2009 | Makower et al. |
| 2009/0198216 A1 | 8/2009 | Muni et al. |
| 2009/0240112 A1 | 9/2009 | Goldfarb et al. |
| 2009/0240237 A1 | 9/2009 | Goldfarb et al. |
| 2009/0312745 A1 | 12/2009 | Goldfarb et al. |
| 2010/0030031 A1 | 2/2010 | Goldfarb et al. |
| 2010/0087811 A1 | 4/2010 | Herrin et al. |
| 2010/0114066 A1 | 5/2010 | Makower et al. |
| 2010/0174308 A1 | 7/2010 | Chang et al. |
| 2010/0198191 A1 | 8/2010 | Clifford et al. |
| 2010/0198302 A1 | 8/2010 | Shalev |
| 2010/0274188 A1 | 10/2010 | Chang et al. |
| 2010/0290244 A1 | 11/2010 | Nath |
| 2011/0166190 A1 | 7/2011 | Anderson et al. |

FOREIGN PATENT DOCUMENTS

| | | |
|---|---|---|
| CN | 2352818 | 12/1999 |
| DE | 3202878 | 8/1983 |
| DE | 4032096 | 4/1992 |
| DE | 4406077 | 9/1994 |
| DE | 8810044 | 11/1998 |
| DE | 29923582 | 12/2000 |
| DE | 10104663 | 8/2002 |
| DE | 10105592 | 8/2002 |
| EP | 129634 | 1/1985 |
| EP | 257605 | 3/1988 |
| EP | 355996 | 2/1990 |
| EP | 418391 | 3/1991 |
| EP | 427852 | 5/1991 |
| EP | 623582 | 11/1994 |
| EP | 624349 | 11/1994 |
| EP | 744400 | 11/1996 |
| EP | 585757 | 6/1997 |
| EP | 893426 | 1/1999 |
| EP | 1042998 | 10/2000 |
| EP | 1166710 | 1/2002 |
| EP | 1413258 | 4/2004 |
| EP | 1944053 | 7/2008 |
| FR | 2859377 | 3/2005 |
| FR | 2916144 | 11/2008 |
| GB | 2125874 | 3/1984 |
| GB | 2305174 | 4/1997 |
| JP | 53-67935 | 6/1978 |
| JP | 10-24098 | 1/1989 |
| JP | 10-34376 | 2/1989 |
| JP | 3-503011 | 7/1991 |
| JP | 3-504935 | 10/1991 |
| JP | 4-221313 | 8/1992 |
| JP | 5-211985 | 8/1993 |
| JP | 6-017751 | 3/1994 |
| JP | 6-277296 | 10/1994 |
| JP | 7-327916 | 12/1995 |
| JP | 8-317989 | 12/1996 |
| JP | 11-507251 | 6/1999 |
| JP | 2000-501634 | 2/2000 |
| JP | 2000-126303 | 5/2000 |
| JP | 2001-501846 | 2/2001 |
| JP | 2001-095815 | 4/2001 |
| JP | 2001-526077 | 12/2001 |
| JP | 2002-028166 | 1/2002 |
| JP | 2002-508214 | 3/2002 |
| JP | 2002-537908 | 11/2002 |
| JP | 2002-538850 | 11/2002 |
| JP | 2003-507140 | 2/2003 |
| JP | 2003-062080 | 3/2003 |
| JP | 2003-521327 | 7/2003 |
| JP | 2004-049583 | 2/2004 |
| JP | 2004-357728 | 12/2004 |
| JP | 2005-323702 | 11/2005 |
| JP | 2005-532869 | 11/2005 |
| RU | 2213530 | 10/2003 |
| SU | 1662571 | 7/1991 |
| WO | WO 90/011053 | 10/1990 |
| WO | WO 90/014865 | 12/1990 |
| WO | WO 91/017787 | 11/1991 |
| WO | WO 92/015286 | 9/1992 |
| WO | WO 92/022350 | 12/1992 |
| WO | WO 94/012095 | 6/1994 |
| WO | WO 96/029071 | 9/1996 |
| WO | WO 97/021461 | 6/1997 |
| WO | WO 99/024106 | 5/1999 |
| WO | WO 99/030655 | 6/1999 |
| WO | WO 99/032041 | 7/1999 |
| WO | WO 00/009192 | 2/2000 |
| WO | WO 00/023009 | 4/2000 |
| WO | WO 00/051672 | 9/2000 |
| WO | WO 00/053252 | 9/2000 |
| WO | WO 00/067834 | 11/2000 |
| WO | WO 01/045572 | 6/2001 |

(56) References Cited

FOREIGN PATENT DOCUMENTS

| WO | WO 01/054558 | 8/2001 |
|---|---|---|
| WO | WO 01/056481 | 8/2001 |
| WO | WO 01/068178 | 9/2001 |
| WO | WO 01/070325 | 9/2001 |
| WO | WO 01/074266 | 10/2001 |
| WO | WO 01/097895 | 12/2001 |
| WO | WO 02/062269 | 8/2002 |
| WO | WO 03/049603 | 6/2003 |
| WO | WO 03/063703 | 8/2003 |
| WO | WO 03/105657 | 12/2003 |
| WO | WO 04/006788 | 1/2004 |
| WO | WO 04/018980 | 3/2004 |
| WO | WO 04/026391 | 4/2004 |
| WO | WO 04/082525 A2 | 9/2004 |
| WO | WO 04/082525 A3 | 9/2004 |
| WO | WO 05/018730 | 3/2005 |
| WO | WO 05/077450 | 8/2005 |
| WO | WO 05/089670 | 9/2005 |
| WO | WO 05/117755 | 12/2005 |
| WO | WO 06/034008 | 3/2006 |
| WO | WO 06/078884 | 7/2006 |
| WO | WO 06/107957 | 10/2006 |
| WO | WO 06/116597 | 11/2006 |
| WO | WO 06/118737 | 11/2006 |
| WO | WO 06/135853 | 12/2006 |
| WO | WO 07/035204 | 3/2007 |
| WO | WO 07/111636 | 10/2007 |
| WO | WO 07/124260 | 11/2007 |
| WO | WO 08/036149 | 3/2008 |
| WO | WO 08/045242 | 4/2008 |
| WO | WO 08/051918 | 5/2008 |
| WO | WO 08/134382 | 11/2008 |

OTHER PUBLICATIONS

Aust, R., et al. 'The Functional Size of the Human Maxillary Ostium in Vivo' Acta. Otolaryn(9178) vol. 78 pp. 423-435.
Baim, D.S., MD 'Grossman's Cardiac Catheterization, Angiography, and Intervention' (2000) Lippincott Williams & Wilkins pp. 76, 84 & 214.
Barrett, S. 'Be Wary of Neurocranial Restructuring (NCR)' Chirobase; Jul. 2003; www.chirobase.org/06DD/ncr.html.
Bartal, N. 'An Improved stent for Use in the Surgical Management of Congenital Posterior Choanal Atresia' J. Laryngol. Otol (1988) vol. 102 pp. 146-147.
Becker, A.E. 'Resetnosis After Angioplasty' The Lancet (1988) vol. 331, No. 8584 p. 352.
Bellis, M. History of the Catheter-Balloon Catheter-Thomas Fogarty. www.inventors.about.com/library/inventors/blcatheter.htm?p=1.
Benninger et al.; Adult Chronic Rhinosinusitis: Definitions, Diagnosis, Epidemiology, and Pathophysilogy Arch Otolarygol Head and Neck Surg. vol. 129 (Sep. 2003) pp. A1-S32.
Bent et al. 'The Frontal Cell as a Cause of Frontal Sinus Obstruction' American Journal of Rhinology, vol. 8, No. 4 (1994) pp. 185-191.
Binner et al. 'Fibre-Optic Transillunination of the Sinuses: A Comparison of the Value of Radiography and Transillumination in Antral Disease' Clinical Otolaryngology. vol. 3 (1978) pp. 1-11.
Brown, C.L. et al., 'Safety and Feasibility of Balloon Catheter Dilation of Paranasal Sinus Ostia: A Preliminary Investigation' Annals of Otology, Rhinology & Laryngology (2006) vol. 115, No. 4 pp. 293-299.
Cakmak, 0., et al., "Effects of paranasal sinus ostia and volume on acoustic rhinometry measurements: a model study," J Appl Physiol, 2003, 94: 1527-1535, XP055155532, 9 pgs.
Casiano et al. 'Endoscopic Lothrop Procedure: The University of Miami Experience' American Journal of Rhinology, vol. 12, No. 5 (1998) pp. 335-339.
Casserly, I.P. et al., Chapter 7. 'Guides and Wires in Percutaneous Coronary Intervention' Strategic Approaches in Coronary Intervention (2006) Lippincott Williams & Wilkins pp. 91-99.

Chien, Y.W. et al. 'Nasal Systemic Drug Delivery' Drugs and Pharmaceutical Sciences, vol. 39, pp. 60-63.
Cohen et al. 'Endoscopic Sinus Surgery: Where we are and where we're going' Current Opinion in Otolaryngology & Head and Neck Surgery, vol. 13 (2005) pp. 32-38.
Colla, A. et al., 'Trihaloacetylated Enol Ethers—General Synthetic Procedure and Heterocyclic Ring Closure Reactions with Hydroxylamine' Synthesis, (Jun. 1991) pp. 483-486.
Costa, M.N. et al. 'Endoscopic Study of the Intranasal Ostium in External Dacryocystorhinostomy Postoperative. Influence of Saline Solution and 5-Flurorouracil' Clinics (2007) vol. 62, Issue 1, pp. 41-46.
Cussler, E.L. 'Diffusion: Mass transfer in Fluid Systems' Cambridge University Press (1996).
Davis, G.E. et al. 'A Complication from Neurocranial Restructuring' Arch Otolaryngol Head Neck Surg. vol. 129 (Apr. 2003) pp. 472-474.
Deutschmann, R. et al. 'A Contribution to the Topical Treatment of [Maxillary] Sinusitis Preliminary Communication' Stomat DDR 26, (1976) pp. 585-592.
Domb, A. et al. 'Handbook of Biodegradable Polymers' Harwood Academic Publishers (1997).
Doyle Nasal Splints, Jan. 25, 2007; www.doylemedical.com/nasalsplints.htm.
Draf, W. 'Endonasal Micro-Endoscopic Frontal Sinus Surgery: the Fulda Concept' Op Tech Otolaryngol Head Neck Surg. vol. 2 (1991) pp. 234-240.
Edmond, C. et al. 'ENT Surgical Stimulator' Nov. 1989.
ENT Checklist; Physical Examinations Performance Checklist [date of publication unknown].
Eremychev, V.A. 'Needles for Puncture and Drainage of the Maxillary Sinus' Meditsinskaya Tekhnika, No. 5 (1974) pp. 54.55.
Feldman, R.L. et al., 'New Steerable, Ultra-Low-Profile, Fixed Wire Angioplasty Catheter: Initial Experience with the Cordis OrionTM Steerable PTCA Balloon Catheter' Cathet. Cardiovasc. Diagn. (1990) vol. 19, No. 2 pp. 142-145.
Ford, C.N. 'A Multipurpose Laryngeal Injector Device' Otolaryngol. Head Neck Surg. (1990) vol. 103, No. 1 pp. 135-137.
Friedman, M., M.D., et al. 'Frontal Sinus Surgery: Endoscopic Technique' Operative Techniques in Otolaryngology—Head and Neck Surgery. vol. 12, No. 2 (Jun. 2001) pp. 60-65.
Friedman, et al. 'Intraoperative and Postoperative Assessment of Frontal Sinus Patency by Transillumination' Laryngoscope. vol. 110 (Apr. 2000) pp. 683-684.
Friedman, et al 'Middle Turbinate Medialization and Preservation in Endoscopic Surgery' Otolaryngology—Head and Neck Surgery. (2000) vol. 123, No. 1, part 1, pp. 76-80.
Fung, M.K.T. 'Template for Frontal Osteoplastic Flap' Laryngoscope. vol. 96 (1986) pp. 578-579.
Gatot, A. et al. 'Early treatment of Orbital Floor Fractures with Catheter Balloon in Children' Int J. Pediatric Otorhinolaryngol (1991) vol. 21 pp. 97-101.
Gerus, I.I. et al. 'β-Ethoxyvinyl Polyfluroroalkyl Ketones—Versatile Synthones in Fluoroorganic Chemistry' Journal of Fluorine Chemistry. vol. 69 (1994) pp. 195-198. Elsevier Science S.A.
Good, R.H. 'An Intranasal Method for Opening the Frontal Sinus Establishing the Largest Possible Drainage' Laryngoscope. vol. 18 (1908) pp. 266-274.
Gopferich 'Polymer Degradation and Erosion: Mechanisms and Application' Eur. J. Parm. Biophar. vol. 42 (1996) pp. 1-11.
Gorlov, D.V. et al 'Acylation of 2-Methoxypropene with Anhydrides and Halides of Perflurocarboxylic Acids in the Presence of Tertiary Amines' Russian Chemical Bulletin. vol. 48 No. 9 (Sep. 1999) pp. 1791-1792. Kluwer Academic/Plenum Publishers.
Gottmann, et al. 'Balloon Dilatation in the Nasal Cavity and Paranasal Sinuses' CIRSE. (Sep. 25, 2004) pp. 1-27.
Gottmann, et al. 'Balloon Dilatation of Recurrent Ostial Occlusion of the Frontal Sinus' CIRSE Abstract (Mar. 2001) B-04353.
Gottman, et al., Balloon Dilatation of Recurrent Ostial Occlusion of the Front Sinus OASIS-Online Abstract Submission and Invitation System, 1996-2006, Coe Truman Technologies, Inc.

(56) References Cited

OTHER PUBLICATIONS

Gottmann, et al. 'Successful Treatment of Recurrent Post-Operative Frontal Sinus Stenoses by Balloon Dilatation' CIRSE. (Oct. 5, 2002)
Gupta, D. et al., 'Dacrystitis Secondary to an Iatrogenic Foreign Body in the Lacrimal Apparatus' Ear, Nose & Throat Journal (2009) www.findarticles.com/p/articles/mi_m0BUM/is_7_88/ai_n32428620/.
Hashim, et al. 'Balloon Compression of the Intermaxillary Sinus for Intractable Post Traumatic Bleeding from the Maxillary Artery' Scandinavian Journal of Plastic and Reconstruction Surgery and Hand Surgery (1999) vol. 33 pp. 321-324.
Hojo, M. et al, 'Electrophilic Substitutions of Olefinic Hydrogens II. Acylation of Vinyle Ethers and N Vinyl Amides Chemistry Letters' (1976) pp. 499-502. Chemical Society of Japan.
Hopf, J.U.G. et al. 'Minatare Endoscopes in Otorhinolaryngologic Applications' Min Invas Ther & Allied Technol. (1998) vol. 7, No. 3 pp. 209-218.
Hosemann, W. et al. A Dissection Course on Endoscopic Endonasal Sinus Surgery (2005) Endo-Press, Tuttlingen pp. 4-37.
Hosemann, W. et al. 'Endonasal Frontal Sinusotomy in Surgical Management of Chronic Sinusitis: A Critical Evaluation' American Journal of Rhinology. vol. 11, No. 1 (1997) pp. 1-9.
Hosemann, M.E. et al. 'Experimentelle Untersuchungen sur Wundheilung in den Nasennebenholhlen. II. Spontaner Wundschluss und medikamentose Effekte im standardisierten Wundmodell.' HNO 39 (1991) pp. 48-54. 'Experimental investigations on wound healing of the paranasal sinuses. II. Spontaneous wound closure and pharmacological effects in a standardized animal model.' HNO 39 (1991) pp. 48-54.
Hosemann, W.G. et al. 'Minimally Invasive Endonasal Sinus Surgery' Thieme, Stuttgart, New York (2000).
Hosemann, M.E. et al. 'Normal Wound Healing of the Paranasal Sinuses—Clinical and Experimental Investigations' Eur Arch Otorhinolarygol. vol. 248, (1991) pp. 390-394.
Hosemann, W. et al. 'Behandlung nach Nasennebenhohleneingriffen, part 2: Theapeutische Maßnahem' HNO akutell 7 (1999) pp. 291-302.
Hospital Corpsman Sickcall Screener's Handbook. Naval Hospital Great Lakes (Apr. 1999) www.brooksidepress.org/Products/Operationa. Medicine/DATA. 2001 pp. 1-6.
Hybels, R.L. 'Transillumination During Osteoplastic Frontal Sinusotomy' The Laryngoscope. vol. 91 (Sep. 1981) pp. 1560.
Ijaduola, T.G.A. 'Use of a Foley Catheter for Short-Term Drainage in Frontal Sinus Surgery' The Journal of Laryngology and Otology. (1989) vol. 103. pp. 375.378.
Ingals, E.F. 'New Operation and Instruments for Draining the Frontal Sinus' Ann. Otol. Rhinol. Layyngol. vol. 14 (1905) pp. 644-649.
Iro, H. et al., 'A New Device for Frontal Sinus Endoscopy: First Clinical Report' Otolaryngol. Head Neck Surg. (2001) vol. 125 No. 6 pp. 613-616.
Jacobs, J.B. '100 Years of Frontal Sinus Surgery' Laryngoscope. vol. 107 (1997) pp. 1-36.
K-Splint Internal Nasal Splints; Jan. 25, 2007; www.invotec.net. rhinology/ksplint.html.
Kaiser, H. et al 'Cortizontherapie, Corticoide in Klinik und Praxis' Thieme, Stuggart (1992) pp. 390-401.
Kennedy, D.W., M.D. et al. 'Diseases of the Sinuses: Diagnosis and Management' (Copyright 2001) by B.C. Decker Inc.
Khomutov, S.M. et al. 'Dissolution of a Mixture of Steroids in Cyclodextrin Solutions: A Model Description' Pharmaceutical Chemistry Journal. vol. 35, No. 11 (Nov. 2001) pp. 627-629.
Kingdom, T.T. et al. 'Image-Guided Surgery of the Sinuses: Current Technology and Applications' Otolaryngol. Clin. North Am. vol. 37, No. 2 (Apr. 2004) pp. 381-400.
Klossek, J.M. et al. 'Local Safety of Intranasal Trimcinolone Acentonide: Clinical and Histological Aspects of Nasal Mucosa in the Long-Term Treatment of Perennial Allergic Rhinitis' Rhinology. vol. 39, No. 1 (2001) pp. 17-22.

Kozlov et al. 'Diagnosis and Treatment of Sinusitis by YAMIK Sinus Catheters' Rhinology (1996) vol. 34, pp. 123-124.
Kuhn, et al. 'The Agger Nasi Cell in Frontal Recess Obstruction: An Anatomic, Radiology and Clinical Correlation' Operative Techniques in Otolaryngology-Head and Neck Surgery. vol. 2, No. 4 (1991) pp. 226-231.
Laliberte, F. et al. 'Clinical and Pathologic Methods to Assess the Long-Term Safety of Nasal Corticosteroids' Allergy. vol. 55, No. 8 (2000) pp. 718-722.
Lang, E.V., et al., 'Access Systems for Puncture at an Acute Angle' J. Vasc. Interv. Radiol. (1995) vol. 6, No. 5 pp. 711-713.
Lanza, D.C. 'Postoperative Care and Avoiding Frontal Recess Stenosis' International Advanced Sinus Symposium (Jul. 21-24, 1993).
Large, G.C. 'Crystalline Tetracycline Hydrochloride in the Treatment of Acute and Chronic Maxillary Sinusitis' Canada. M.A.J. (1958) vol. 79 pp. 15-16.
Lund, V.J. 'Maximal Medical Therapy for Chronic Rhinosinusitis' Otolaryngol Clin N. Am. vol. 38 (2005) pp. 1301-1310.
Maran, A.G.D. et al. 'The Use of the Foley Balloon Catheter in the Tripod Fracture' J. Laryngol. Otol. (1971) vol. 85, Issue 9, pp. 897-902.
May, M. et al. 'Frontal Sinus Surgery: Endonasal Drainage Instead of an External Osteopolstic Approach' Op Tech Otolaryngo Head Neck Surgery. 6 (1995) pp. 184-192.
Medtronic, xomed.com—MicroFrance Catalog Browser. www.xomcat.com/xomfrance/index.php?zone=both&cat=18&sub=58&prodline=1272 (Dec. 31, 2003) pp. 1-2.
Mehan, V.K. et al., 'Coronary Angioplasty through 4 French Diagnostic Catheters' Cathet. Cardiovasc. Diagn. (1993) vol. 30, No. 1 pp. 22-26.
Mellor, J.M. et al 'Synthesis of Trifluromethylnaphthalenes' Tetrahedron. vol. 56 (2000) pp. 10067-10074. Elsevier Science Ltd.
Metson, R., et al., 'Endoscopic Treatment of Sphenoid Sinusitis' Otolaryngol. Head Neck Surg. (1996) vol. 114, No. 6 pp. 736-744.
Metson, R. 'Holmium: YAG Laser Endoscopic Sinus Surgery: A Randomized Controlled Study' Laryngoscope. vol. 106, Issue 1, Supplement 77 (Jan. 1996) pp. 1-18.
Miller, et al. 'Management of Fractures of the Supraorbital Rim' Journal of Trauma. vol. 18, No. 7 (Jul. 1978) pp. 507-512.
Min, Y-G et al. 'Mucociliary Activity and Histopathology of Sinus Mucosa in Experimental Maxillary Sinusitis: A Comparison of Systemic Administration of Antibiotic and Antibiotic Delivery by Polylactic Acid Polymer' Laryngoscope. vol. 105 (Aug. 1995) pp. 835-842.
Mols, B. 'Movable Tool Tip for Keyhole Surgery' Delft Outlook, vol. 3 (2005) pp. 13-17.
Mooney, M.R., et al., 'Monorail™ Piccolino Catheter: A New Rapid Exchange/Ultralow Profile Coronary Angioplasty System' Cathet. Cardiovasc. Diagn. (1990) vol. 20, No. 2 pp. 114-119.
Moriguchi, T. et al. 'Additional-Elimination Reaction in the Trifluoroacetylation of Electron-Rich Olefins' J. Org. Chem. vol. 60, No. 11 (1995) pp. 3523.3528. Ameiican Chemical Society.
Nsal Surgery and Accessories, Jan. 25, 2007; www.technologyforlife.com/au/ent/nasal.html.
Park, K. et al. 'Biodegradable Hydrogels for Drug Delivery' (1993) Technomic Publishing Inc. Lancaster.
Piccirillo, J.F. et al. 'Physchometric and Clinimetric Validity of the 20-Item Sino-Nasal Outcome test (SNOT-20)' Copyright 1996 Washington University, St. Louis, MO.
Piers, et al. 'A Flexible Distal Tip with Two Degrees of Freedom for Enhanced Dexterity in Endoscopic Robot Surgery' Proceedings 13th Micromechanics Europe Workshop (2002) pp. 271-274.
Podoshin, L et al. 'Balloon Technique for Treatment of Frontal Sinus Fractures' The journal of Laryngology & Otology (1967), vol. 81. pp. 1157-1161.
Pownell, P.H. et al., 'Diagnostic Nasal Endoscopy' plastic & Reconstructive Surgery (1997) vol. 99, Iss5 pp. 1451-1458.
Prince, et al. 'Analysis of the Intranasal Distribution of Ointment' J Otolaryngol. vol. 26 (1997) pp. 357-360.
Ramsdale, D.R., Illustrated Coronary Intervention: A case-oriented approach, (2001) Martin Dunitz Ltd. pp. 1-5.

(56) References Cited

OTHER PUBLICATIONS

Ritter, F.N. et al., Atlas of Paranasal Sinus Surgery (1991) Igaku-Shoin Medical Pub. pp. 1-81.
Robison, J. Mathews, M.D. 'Pressure Treatment of Maxillary Sinusitis' J.A.M.A. (May 31, 1952) pp. 436-440.
Robison, J. Mathews, M.D. 'Pressure Treatment of Purulent Maxillary Sinusitis' Texas State Journal of Medicine (May 1952) pp. 281-288.
St. Croix et al. 'Genes Expressed in Human Tumor Endothelium' Science, vol. 289 (May 15, 2000) pp. 1197-1202.
Sama, A., et al., 'Current Opinions on the Surgical Management of Frontal Sinus Disease' ENT News. Www.pinpointmedical.com/ent-news (2009) vol. 17, No. 6 pp. 60-63.
Sanborn, T.A. et al., 'Percutaneous Endocardial Transfer and Expression of Genes to the Myocardium Utilizing Fluropscopic Guidance' Catheter Cardiovasc. Interv. (2001) vol. 52, No. 2 pp. 260-266.
Sawbones Catalog 2001, Pacific Research Laboratories, Inc., Vashon Washington 98070 USA.
Saxon, R.R. et al., 'Technical Aspects of Accessing the Portal Vein During the TIPS Procedure' J. Vasc. Interv. Radiol. (1997) vol. 8, No. 5 pp. 733-744.
Schaefer, S.D., M.D. 'Rhinology and Sinus Disease: A Problem-Oriented Approach' (Copyright 1988) by Mosby, Inc.
Schneider. Pfizer Ad for Softip [date of publication unknown].
Shah, N.J. et al., 'Endoscopic Pituitary Surgery—A Beginner's Guide' Indian Journal of Otolaryngology and Head and Neck Surgery (2004) vol. 56, No. 1 pp. 71-78.
Shah, N.J. 'Functional Endoscopic Sinus Surgery' (1999); found at bhj.org/journal/1999_4104_oct99/sp_659.htm.
Single-Pole and Multi-Pole Lightguides for UV Spot Light Curing Systems.
Sobol, et al. 'Sinusitis, Maxillary, Acute Surgical Treatment.' eMedicine. Retrieved from the Internet: <<http://emedicine.medscape.com/article/862030-print>> (Nov. 16, 2010) pp. 1-11.
Stammberger, H. 'Komplikationen entzundlicher Nasen-nebenhohlenerkrankungen eischließ iatrogen bedingter Komplikationen' Eur Arch Oti-Rhino-Laryngol Supple. (Jan. 1993) pp. 61-102.
Stammberger, et al. Chapter 3 'Special Endoscopic Anatomy of the Lateral Nasal Wall and Ethmoidal Sinuses' Functional Endoscopic Sinus Surgery. (1991) Ch. 3, pp. 49-87.
Strohm, et al. Die Behandlung von Stenosen der oberen Luftwege mittels rontgenologisch gesteuerter Ballondilation (Sep. 25, 1999) pp. 1-4.
Strohm, et al 'Le Traitement des Stenoses Voies Aeriennes Superieures Par Dilation Ay Balloon' Sep. 25, 1999.
Strohm, et al. 'Treatment of Stenoses of the Upper Airways by Balloon Dilation' Sudwestdeutscher Abstract 45 (Sep. 25, 1999) pp. 1-3.
SurgTrainer Product Information 'Incisive Human Nasal Model for ESS Training' Surg Trainer, Ltd. Ibaraki, Japan (2004) www1.accsnet.ne.jp/~juliy/st/en/partslist.html.
Tabor, M.H. et al., 'Symptomatic Bilateral Duct Cysts in a Newborn-Rhinoscopic Clinic' Ear, Nose & Throat Journal (2003) www.findarticles.com/p/articles/mi_m0BUM/is_2_82/ai_98248244 pp. 1-3.
Tarasov, D.I. et al. 'Application of Drugs Based on Polymers in the Treatment of Acute and Chronic Maxillary Sinusitis' Vestn Otorinoloaringol. vol. 6 (1978) pp. 45-47.
Terumo. Medi-Tech. Boston Scientific. (1993) Ad of Glidewire.
The Operating Theatre Journal (www.otjonline.com) 'Disposable Medical Device for Wound Disclosure/The Tristel Purple Promotion—A Collaboration between Tristel PLC and Karl Storz Ednoscopy (UK) Ltd.' p. 4.
Weber, R. et al. 'Endonasale Stirnhohlenchirugie mit Langzeiteinlage eines Platzhalters' Laryngol. Rhinol. Otol. vol. 76 (1997) pp. 728-734. (English Abstract).
Weber, R. et al., 'Videoendoscopic Analysis of Nasal Steroid Distribution' Rhinology. vol. 37 (1999) pp. 69-73.
Weiner, R.I., D.O., et al., 'Development and Application of Transseptal Left Heart Catheterization' Cathet. Cardiovasc. Diagn. (1988) vol. 15, No. 2, pp. 112-120.
Wiatrak, B.J., et al., 'Unilateral Choanal Atresia: Initial Presentation and Endoscopic Repair' International Journal of Pediatric Otorhinolaryngology (1998) vol. 46, pp. 27-35.
Woog, et al. 'Paranasal Sinus Endoscopy and Orbital Fracture Repair' Arch Ophthalmol. vol. 116 (May 1998) pp. 688-691.
Wormald, P.J., et al., 'The 'Swing-Door' Technique for Uncinectomy in Endoscopic Sinus Surgery' The Journal of Laryngology and Otology (1998) vol. 112, pp. 547-551.
Xomed-Treace. Bristol-Myers Squibb. Ad for Laser Shield II. Setting the Standards for Tomorrow. [date of publication unknown].
Yamauchi, Y. et al., 'Development of a Silicone Model for Endoscopic Sinus Surgery' Proc International Journal of Computer Assisted Radiology and Surgery vol. 99 (1999) p. 1039.
Yamauchi, Y., et al., 'A Training System for Endoscopic Sinus Surgery with Skill Evaluation' Computer Assisted Radiology and Surgery (2001) with accompanying poster presentation.
Yanagisawa et al. 'Anterior and Posterior Fontanelles.' Ear, Nose & Throat Journal (2001) vol. 80. pp. 10-12.
Zimarino, M., M.D., et al., 'Initial Experience with the EuropassTM: A new Ultra-Low-Profile Monorail Balloon Catheter' Cathet. Cardiovasc. Diagn. (1994) vol. 33, No. 1. pp. 76-79.
Australian Office Action, Examiners First Report dated Apr. 8, 2010 for Application No. AU 2005274794.
Australian Office Action, First Examination Report, dated Apr. 11, 2014 for Application No. 2009276553.
Canadian Office Action dated Jun. 18, 2015 for Application No. 2,732,769.
Chinese Office Action, First Office Action, dated Nov. 21, 2012 for Application No. 200980130717.5.
Chinese Office Action, Second Office Action, dated Jul. 22, 2013 for Application No. 200980130717.5.
Chinese Office Action, Third Office Action, dated Jan. 17, 2014 for Application No. 200980130717.5.
Chinese Search Report dated Nov. 9, 2012 for Application No. 200980130717.5.
European Written Opinion dated Jul. 7, 2014 for Application No. EP 13180296.9.
European Written Opinion dated Dec. 5, 2014 for Application No. EP 13180296.9.
European Written Opinion dated Oct. 29, 2015 for Application No. EP 13180296.9.
European Written Opinion dated Aug. 22, 2016 for Application No. EP 13180296.9.
European Communication dated Sep. 4, 2008 for Application No. EP 05773189.
European Communication dated Jun. 19, 2009 for Application No. EP 05773189.
European Exam Report dated Feb. 22, 2006 for Application No. EP 02716734.5.
European Exam Report dated Feb. 8, 2007 for Application No. EP 02716734.5.
European Search Report and Written Opinion dated Sep. 11, 2009 for Application No. EP 06815174.
European Search Report dated Sep. 27, 2011 for Application No. EP 10182961.
European Search Report dated Sep. 29, 2011 for Application No. EP 10182893.
Partial European Search Report dated Sep. 20, 2007 for Application No. EP 07252018.
Partial European Search Report dated Mar. 25, 2008 for Application No. EP 07252018.
Supplemental Partial European Search Report dated Jun. 2, 2008 for Application No. EP 05773189.
Supplemental Partial European Search Report dated Jul. 1, 2009 for Application No. EP 06815285.
Supplemental Partial European Search Report dated Nov. 19, 2010 for Application No. EP 06751637.
Supplemental European Search Report dated Jan. 29, 2010 for Application No. EP 07836108.
Supplemental European Search Report dated Feb. 2, 2010 for Application No. EP 07836109.
Supplemental European Search Report dated Feb. 17, 2010 for Application No. EP 07836110.

(56) References Cited

OTHER PUBLICATIONS

Supplemental European Search Report dated Mar. 1, 2010 for Application No. EP 05778834.
Supplemental European Search Report dated Mar. 16, 2010 for Application No. EP 06718986.
Supplemental European Search Report dated Jun. 22, 2010 for Application No. EP 06784759.
Supplemental European Search Report dated Sep. 23, 2010 for Application No. EP 08746715.
Supplemental European Search Report dated Jan. 28, 2011 for Application No. EP 07777004.
Supplemental European Search Report dated Mar. 31, 2011 for Application No. EP 05798331.
Supplemental European Search Report dated Aug. 30, 2011 for Application No. EP 06800540.
Supplemental European Search Report dated Sep. 29, 2011 for Application No. EP 07750248.
Extended European Search Report dated Oct. 10, 2013 for Application No. 13180296.9.
PCT Search Report dated Nov. 30, 2009 for Application No. UPCT/US2009/057203.
International Preliminary Report on Patentability dated Aug. 7, 2006 for Application No. PCT/US05/25371.
International Preliminary Report on Patentability and Written Opinion dated Sep. 25, 2007 for Application No. PCT/US06/002004.
International Preliminary Report on Patentability dated Feb. 15, 2008 for Application No. PCT/US05/13617.
International Preliminary Report on Patentability and Written Opinion dated Nov. 18, 2008 for Application No. PCT/US07/11449.
International Preliminary Report on Patentability and Written Opinion dated Apr. 7, 2009 for Application No. PCT/US07/021170.
International Preliminary Report on Patentability and Written Opinion dated May 5, 2009 for Application No. PCT/US06/036960.
International Preliminary Report on Patentability and Written Opinion dated Oct. 13, 2009 for Application No. PCT/US08/059786.
International Preliminary Report on Patentability and Written Opinion dated Oct. 27, 2009 for Application No. PCT/US08/061343.
International Preliminary Report on Patentability and Written Opinion dated Feb. 1, 2011 for Application No. PCT/US2009/052236.
International Search Report dated Jun. 3, 2002 for Application No. PCT/EP02/01228.
International Search Report and Written Opinion dated Apr. 10, 2006 for Application No. PCT/US05/25371.
International Search Report dated May 8, 2007 for Application No. PCT/US2006/16026.
International Search Report and Written Opinion dated Jul. 21, 2008 for Application No. PCT/US05/033090.
International Search Report dated Aug. 25, 2008 for Application No. PCT/US2008/000911.
International Search Report dated Sep. 10, 2008 for Application No. PCT/US07/016212.
International Search Report and Written Opinion dated Sep. 12, 2008 for Application No. PCT/US07/16214.
International Search Report and Written Opinion dated Sep. 17, 2008 for Application No. PCT/US08/059786.
International Search Report and Written Opinion dated Sep. 17, 2008 for Application No. PCT/US08/061343.
International Search Report and Written Opinion dated Oct. 1, 2008 for Application No. PCT/US07/011449.
International Search Report dated Oct. 15, 2008 for Application No. PCT/US2008/061048.
International Search Report dated Nov. 30, 2009 for Application No. PCT/US2009/057203.
International Search Report dated Dec. 10, 2009 for Application No. PCT/US2009/052236.
International Search Report dated Dec. 16, 2009 for Application No. PCT/US2009/050800.
International Search Report dated Mar. 31, 2010 for Application No. PCT/US2009/069143.
International Search Report dated Jul. 8, 2010 for Application No. PCT/US2010/027837.
International Search Report and Written Opinion dated Oct. 6, 2010 for Application No. PCT/US2010/040548.
International Search Report dated Mar. 25, 2011 for Application No. PCT/US2010/062161.
International Search Report dated Mar. 28, 2011 for Application No. PCT/US2010/061850.
International Search Report dated Mar. 31, 2011 for Application No. PCT/US2010/060898.
International Search Report dated Aug. 9, 2011 for Application No. PCT/US2011/038751.
International Search Report dated May 18, 2012 for Application No. PCT/US2011/052321.
Partial International Search Report dated Feb. 7, 2012 for Application No. PCT/US2011/052321.
Japanese Office Action, Notification of Reasons for Refusal, dated Jul. 2, 2013 for Application No. 2011-521316.
Mexican Examination Report dated Aug. 15, 2013 for Application No. MX/a/2011/001099.
Mexican Examination Report dated Nov. 15, 2013 for Application No. MX/a/2011/001099.
USPTO Office Action dated Sep. 16, 2005 for U.S. Appl. No. 10/259,300.
USPTO Office Action dated Jul. 7, 2006 for U.S. Appl. No. 10/259,300.
USPTO Office Action dated Feb. 13, 2007 for U.S. Appl. No. 10/259,300.
USPTO Office Action dated Oct. 9, 2007 for U.S. Appl. No. 10/259,300.
USPTO Office Action dated Jan. 24, 2008 for U.S. Appl. No. 10/259,300.
USPTO Office Action dated Oct. 6, 2008 for U.S. Appl. No. 10/259,300.
USPTO Office Action dated May 29, 2007 for U.S. Appl. No. 10/912,578.
USPTO Office Action dated Nov. 14, 2007 for U.S. Appl. No. 10/912,578.
USPTO Office Action dated Dec. 10, 2007 for U.S. Appl. No. 10/912,578.
USPTO Office Action dated Oct. 18, 2007 for U.S. Appl. No. 11/037,548.
USPTO Office Action dated Dec. 6, 2007 for U.S. Appl. No. 11/037,548.
USPTO Office Action dated Apr. 9, 2008 for U.S. Appl. No. 11/037,548.
USPTO Office Action dated Nov. 28, 2007 for U.S. Appl. No. 11/234,395.
USPTO Office Action dated Sep. 12, 2008 for U.S. Appl. No. 10/829,917.
USPTO Office Action dated Nov. 17, 2008 for U.S. Appl. No. 10/829,917.
USPTO Office Action dated Mar. 18, 2009 for U.S. Appl. No. 10/829,917.
USPTO Office Action dated Nov. 9, 2009 for U.S. Appl. No. 10/829,917.
USPTO Office Action dated Oct. 29, 2008 for U.S. Appl. No. 11/347,147.
USPTO Office Action dated Feb. 4, 2009 for U.S. Appl. No. 11/347,147.
USPTO Office Action dated Aug. 6, 2009 for U.S. Appl. No. 11/347,147.
USPTO Office Action dated Nov. 7, 2008 for U.S. Appl. No. 10/944,270.
USPTO Office Action dated Jan. 28, 2009 for U.S. Appl. No. 10/944,270.
USPTO Office Action dated Apr. 21, 2009 for U.S. Appl. No. 10/944,270.
USPTO Office Action dated Nov. 17, 2008 for U.S. Appl. No. 12/117,582.
USPTO Office Action dated Mar. 3, 2009 for U.S. Appl. No. 12/117,582.

(56) References Cited

OTHER PUBLICATIONS

USPTO Office Action dated Aug. 6, 2009 for U.S. Appl. No. 12/117,582.
USPTO Office Action dated Nov. 17, 2008 for U.S. Appl. No. 12/118,931.
USPTO Office Action dated Mar. 4, 2009 for U.S. Appl. No. 12/118,931.
USPTO Office Action dated Jul. 30, 2009 for U.S. Appl. No. 12/118,931.
USPTO Office Action dated Nov. 25, 2008 for U.S. Appl. No. 12/117,961.
USPTO Office Action dated Aug. 6, 2009 for U.S. Appl. No. 12/117,961.
USPTO Office Action dated Dec. 5, 2008 for U.S. Appl. No. 12/120,902.
USPTO Office Action dated Oct. 21, 2009 for U.S. Appl. No. 12/120,902.
USPTO Office Action dated Mar. 17, 2009 for U.S. Appl. No. 11/690,127.
USPTO Office Action dated Mar. 23, 2009 for U.S. Appl. No. 11/804,309.
USPTO Office Action dated Mar. 23, 2009 for U.S. Appl. No. 11/926,326.
USPTO Office Action dated Aug. 28, 2009 for U.S. Appl. No. 11/150,847.
U.S. Appl. No. 60/844,874, filed Sep. 15, 2006.
U.S. Appl. No. 60/922,730, filed Apr. 9, 2007.
U.S. Appl. No. 61/052,413, filed May 12, 2008.
U.S. Appl. No. 61/084,949, filed Jul. 30, 2008.
U.S. Appl. No. 11/789,705, filed Apr. 24, 2007.
U.S. Appl. No. 12/512,420, filed Jul. 30, 2009.
U.S. Appl. No. 14/446,537, filed Jul. 30, 2014.
European Examination Report dated Aug. 3, 2011 for Application No. 09790994.9, 4 pages.
European Examination Report dated Jan. 26, 2015 for Application No. 09790994.9, 4 pages.
European Examination Report dated Nov. 25, 2015 for application No. 09790994.9, 4 pages.
European Examination Report dated Nov. 3, 2016 for Application No. 09790994.9, 5 pages.
European Examination Report dated May 23, 2017 for Application No. 13180296.9, 4 pages.
Korean Notice of Preliminary Rejection dated Oct. 19, 2015 for Application No. 10-2011-7004167, 5 pages.
Mexican Examination Report dated Mar. 14, 2014 for Application No. MX/A/2011001099, 4 pages.
Russian Examination Report dated unknown for Application No. 201107229, 4 pages.

\* cited by examiner

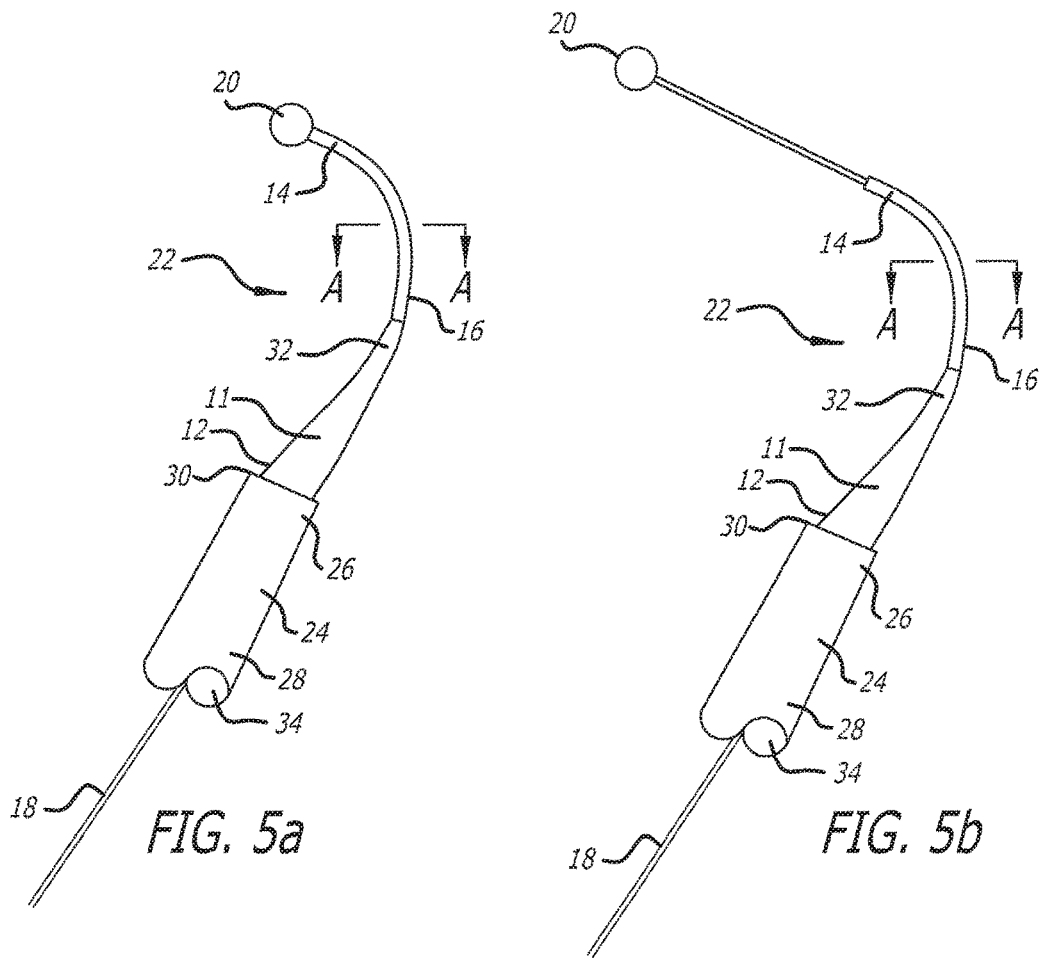
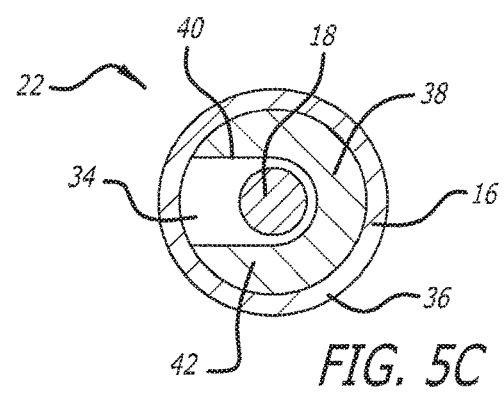

PARANASAL OSTIUM FINDER DEVICES AND METHODS

CROSS-REFERENCES TO RELATED APPLICATIONS

This application is a continuation of patent application Ser. No. 14/446,537, filed Jul. 30, 2014, issued as U.S. Pat. No. 9,750,401 on Sep. 5, 2017, which is a continuation of patent application Ser. No. 12/512,420, filed Jul. 30, 2009, issued as U.S. Pat. No. 8,979,888 on Mar. 17, 2015, which claims the benefit of Provisional Application Ser. No. 61/084,965, filed Jul. 30, 2008, the contents of which are incorporated by reference.

FIELD OF THE INVENTION

The present invention relates generally to medical devices, systems and methods and more particularly to methods and devices for locating and dilating paranasal sinus ostia.

BACKGROUND OF THE INVENTION

The skull contains a series of cavities known as paranasal sinuses that are connected by passageways. The paranasal sinuses include frontal sinuses, ethmoid sinuses, sphenoid sinuses and maxillary sinuses. The paranasal sinuses are lined with mucous-producing mucosal tissue and ultimately open into the nasal cavity. Normally, mucous produced by the mucosal tissue slowly drains out of each sinus through an opening known as an ostium. If the mucosal tissue of one of these passageways becomes inflamed for any reason, the cavities which drain through that passageway can become blocked. This blockage can be periodic (resulting in episodes of pain) or chronic. This interference with drainage of mucous (e.g., occlusion of a sinus ostium) can result in mucosal congestion within the paranasal sinuses. Chronic mucosal congestion of the sinuses can cause damage to the epithelium that lines the sinus with subsequent decreased oxygen tension and microbial growth (e.g., a sinus infection).

The term "sinusitis" refers generally to any inflammation or infection of the paranasal sinuses caused by bacteria, viruses, fungi (molds), allergies or combinations thereof. It has been estimated that chronic sinusitis (e.g., lasting more than 3 months or so) results in 18 million to 22 million physician office visits per year in the United States. Patients who suffer from sinusitis typically experience at least some of the following symptoms: headaches or facial pain; nasal congestion or post-nasal drainage; difficulty breathing through one or both nostrils; bad breath; and/or pain in the upper teeth.

One of the ways to treat sinusitis is by restoring the lost mucous flow. The initial therapy is typically drug therapy using anti-inflammatory agents to reduce the inflammation and antibiotics to treat the infection. A large number of patients do not respond to drug therapy. Currently, the gold standard for patients with chronic sinusitis that do not respond to drug therapy is a corrective surgery called Functional Endoscopic Sinus Surgery (FESS).

During FESS, an endoscope is inserted into the nose and, under visualization through the endoscope, the surgeon may remove diseased or hypertrophic tissue or bone and may enlarge the ostia of the sinuses to restore normal drainage of the sinuses. FESS procedures are typically performed with the patient under general anesthesia.

Although FESS continues to be the gold standard therapy for surgical treatment of severe sinus disease, FESS does have several shortcomings. For example, FESS can cause significant post-operative pain. Also, some FESS procedures are associated with significant post-operative bleeding and, as a result, nasal packing is frequently placed in the patient's nose for some period of time following the surgery. Such nasal packing can be uncomfortable and can interfere with normal breathing, eating, drinking etc. Also, some patients remain symptomatic even after multiple FESS surgeries. Additionally, some FESS procedures are associated with risks of iatrogenic orbital, intracranial and sino-nasal injury. Many otolaryngologists consider FESS an option only for patients who suffer from severe sinus disease (e.g., those showing significant abnormalities under CT scan). Thus, patients with less severe disease may not be considered candidates for FESS. One of the reasons why FESS procedures can be bloody and painful relates to the fact that instruments having straight, rigid shafts are used. In order to target deep areas of the anatomy with such straight rigid instrumentation, the physician needs to resect and remove or otherwise manipulate any anatomical structures that may lie in the direct path of the instruments, regardless of whether those anatomical structures are part of the pathology.

New devices, systems and techniques are being developed for the treatment of sinusitis and other disorders of the ear, nose, throat and paranasal sinuses. For example, various catheters, guide wires and other devices useable to perform minimally invasive, minimally traumatic ear, nose and throat surgery have been described in U.S. patent application Ser. No. 10/829,917 entitled "Devices, Systems and Methods for Diagnosing and Treating Sinusitis and Other Disorders of the Ears, Nose and/or Throat," issued as U.S. Pat. No. 7,654,997 on Feb. 2, 2010, Ser. No. 10/912,578 entitled "Implantable Device and Methods for Delivering Drugs and Other Substances to Treat Sinusitis and Other Disorders," issued as U.S. Pat. No. 7,361,168 on Apr. 22, 2008, Ser. No. 10/944,270 entitled "Apparatus and Methods for Dilating and Modifying Ostia of Paranasal Sinuses and Other Intranasal or Paranasal Structures," published as U.S. Pub. No. 2006/0004321 on Jan. 5, 2006, now abandoned, Ser. No. 11/037,548 entitled "Devices, Systems and Methods For Treating Disorders of the Ear, Nose and Throat," issued as U.S. Pat. No. 7,462,175 on Dec. 9, 2008 and Ser. No. 11/116,118 entitled "Methods and Devices For Performing Procedures Within the Ear, Nose, Throat and Paranasal Sinuses," issued as U.S. Pat. No. 7,720,521 on May 18, 2010. Each of these applications is hereby incorporated herein, in its entirety, by reference thereto. Many of these new devices, systems and techniques are useable in conjunction with endoscopic, radiographic and/or electronic/electromagnetic visualization assistance to facilitate precise positioning and movement of catheters, guide wires and other devices within the ear, nose, throat and paranasal sinuses and to avoid undesirable trauma or damage to critical anatomical structures such as the eyes, facial nerves and brain.

In one new procedure (referred to herein as a "Flexible Transnasal Sinus Intervention" or FTSI, or the Balloon Sinuplasty™ procedure), a dilatation catheter (e.g., a balloon catheter or other type of dilator) is advanced through the nose or some other entry path into the patient's head to a position within the ostium of a paranasal sinus or other location, without requiring removal or surgical alteration of other intranasal anatomical structures. The dilatation catheter is then used to dilate the ostium or other anatomical structures (such as man-made openings into a paranasal sinus and/or spaces within the nasal cavity) to facilitate natural drainage from the sinus cavity. In some cases, a tubular guide may be initially inserted through the nose and advanced to a position near the sinus ostium, and a guide wire may then be advanced through the tubular guide and into the affected paranasal sinus. The dilatation catheter may then be advanced over the guide wire and through the tubular guide to a position where its dilator (e.g., balloon) is positioned within the sinus ostium. The dilator (e.g., balloon) is then expanded, causing the ostium to dilate. In some cases, such dilatation of the ostium may fracture, move or remodel bony structures that surround or are adjacent to the ostium. Optionally, in some procedures, irrigation solution and/or therapeutic agents may be infused through a lumen of the dilatation catheter and/or other working devices (e.g., guide wires, catheters, cannula, tubes, dilators, balloons, substance injectors, needles, penetrators, cutters, debriders, microdebriders, hemostatic devices, cautery devices, cryosurgical devices, heaters, coolers, scopes, endoscopes, light guides, phototherapy devices, drills, rasps, saws, etc.) may be advanced through the tubular guide and/or over the guide wire to deliver other therapy to the sinus or adjacent tissues during the same procedure in which the FTSI is carried out. In FTSI procedures, structures and passageways other than sinus ostia may be dilated using the tools described above, tissue may be resected or ablated, bone may be restructured, drugs or drug delivery systems may be deployed, etc., as described in the documents incorporated herein by reference.

In FTSI procedures that include positioning of a guide wire into a paranasal sinus, the placement of the guide wire through a sinus ostium is typically preceded by the user finding the target ostium with a sinus seeker. The user or surgeon places a sinus seeker into the nasal passageway, and then by tactile feedback (i.e., by "feel") finds the target ostium by contacting the distal end of the sinus seeker with the target sinus ostium. Use of more than one sinus seeker device may be required to locate the target ostium. The surgeon then removes the sinus seeker from the patient and introduces a guide catheter into the nasal passage. The guide wire is introduced into the nasal passageway through the guide catheter and, by tactile memory, the surgeon directs or positions the guide wire to the target ostium. When fluoroscopy or other x-ray visualization techniques are available, the physician may still utilize a sinus seeker prior to inserting the guide wire into a patient due to the physician's familiarity with using a sinus seeker to find the target ostium.

The insertion and removal of the ostium locating device, followed by introduction of a guide catheter and guide wire, results in repeated intrusion of devices into the patient's paranasal cavity and may correspondingly result in increased tissue trauma, increased post-operative recovery time, and/or increased surgery time (and thus cost) involved in the procedure. Presently, no single device is capable of both finding a target ostium and introducing a guide wire into the paranasal cavity to the target ostia, thus allowing the completion of two tasks in one step. There is a need for such methods and devices that can accurately determine the position of a target paranasal sinus ostium and also feed or position a guide wire into the target ostium during sinus procedures.

A need also exists for simplified devices and methods for accessing and dilating a maxillary sinus ostium. The maxillary sinus ostium can often be difficult to locate and treat, and in many cases it may be advantageous to dilate the maxillary ostium and also dilate an area or move an anatomical structure outside of the sinus (in the paranasal cavity) to help treat sinusitis. For example, it may be desirable in some case to dilate the middle meatus or infundibulum or move the middle meatus, anterior ethmoid air cell or uncinate process. It would be ideal if a physician could do so without removing tissue and with a relatively convenient tool or set of tools. The present invention will address at least some of these needs.

The present disclosure addresses these and other needs.

SUMMARY

The invention provides sinus seeker or sinus ostium finder or seeker devices and methods for introducing a guide wire into a target sinus ostium using the sinus seeker device itself. The present disclosure also provides a probe with a dilator for locating and dilating the maxillary sinus and for dilating a space outside the maxillary sinus.

The sinus ostium finder of the invention comprises, in general terms: a shaft having a distal end, a proximal end, a curved region located between the distal and proximal ends, and an interior channel; an extensible and retractable guide wire movably mounted within the interior channel; and a probe tip joined to the guide wire. The guide wire is reversibly movable between a retracted position wherein the probe tip is adjacent to the distal end, and an extended position wherein the probe tip is separated from the distal end.

The probe with dilator device includes a shaft with a rigid proximal end and a less rigid, curved distal end with an atraumatic, probe-like distal tip. The device can further include one or more expandable dilators attached along the shaft such as to the curved distal portion or which is advanceable along the shaft.

In certain embodiments the probe tip is detachable and interchangeable.

In certain embodiments the sinus ostium finder further comprises a handle joined to the proximal end.

In certain embodiments the shaft further comprises an exterior sheath and an interior element, the interior channel extending through the interior element.

In certain embodiments the interior element comprises a rigid material and the exterior sheath comprises a resilient material.

In certain embodiments the interior element is removable and interchangeable.

In certain embodiments the sinus ostium finder further comprises an actuator element mechanically coupled to the guide wire. The actuator element may be located on the handle and mechanically coupled to the guide wire. The actuator element may be slidably mounted within a slot on the handle.

In certain embodiments the shaft further comprises a tubular inner sheath and a tubular outer sheath, the inner sheath positioned within the outer sheath, the interior channel extending through the inner sheath.

In certain embodiments the interior sheath may be extensible and retractable with respect to the outer sheath.

In certain embodiments the shaft further comprises a slot communicating with the interior channel, the slot structured and configured to allow the guide wire to be inserted into and removed from the interior channel through the slot.

In certain embodiments the outer sheath includes a first slot and the inner sheath includes a second slot, the first and second slots structured and configured to allow the guide wire to be inserted into and removed from the interior channel through the first and second slots when the first and second slots are aligned with each other.

In certain embodiments the shaft further comprises a front portion and a back portion joined to the front portion, the front and back portions defining a tubular shape, the interior channel located between the front and back portions.

In certain embodiments the front portion further comprises a slot, the slot communicating with the interior channel, the slot structured and configured to allow the guide wire to be inserted into and removed from the interior channel through the slot.

In many embodiments the sinus ostium finder of the invention may comprise:
an elongated shaft having a distal end and a proximal end, and a curved region between the proximal and distal ends; a handle joined to the proximal end; a longitudinal interior channel extending through the shaft and the handle; an extensible and retractable guide wire movably mounted within the interior channel; a probe tip joined to an end of the guide wire; and an actuator element associated with the handle and mechanically coupled to the guide wire, the guide wire extensible and retractable according to adjustment of the actuator element.

The invention also provides methods for locating a target ostium. The subject methods comprise, in general terms: providing a sinus ostium finder having a shaft with a distal end, a proximal end, a curved region located between the distal and proximal ends, and an interior channel, with an extensible and retractable guide wire movably mounted within the interior channel, and a probe tip joined to the guide wire; inserting the shaft of the sinus ostium finder into a patient's paranasal cavity; adjusting the position of the distal end of the shaft; and adjusting the position of the guide wire and the probe tip until the target ostium is located.

In certain embodiments the methods further comprise withdrawing the shaft from the paranasal cavity while leaving the guide wire and the probe tip in the adjusted position.

In certain embodiments the methods further comprise introducing a surgical device along the guide wire to the target ostium.

In certain embodiments, the probe can embody a device for locating and dilating a natural ostium of a maxillary sinus, the device comprising an elongate shaft, comprising a substantially rigid proximal portion, a curved distal portion, an atraumatic distal tip at the end of the curved distal portion, wherein the curved distal portion has a size and shape to allow passage of the distal portion into a nasal cavity to position the atraumatic distal tip within or near a maxillary sinus ostium and an inflation lumen passing through at least part of the shaft, at least one expandable dilator coupled with the distal portion of the shaft in fluid communication with the inflation lumen.

In other embodiments, the device for locating and dilating a natural ostium of a maxillary sinus can embody an elongate inner shaft, comprising a substantially rigid proximal portion, a curved distal portion, and an atraumatic distal tip at the end of the curved distal portion, wherein the curved distal portion has a size and shape to allow passage of the distal portion into a nasal cavity to position the atraumatic distal tip within or near a maxillary sinus ostium and an outer shaft slidably disposed over the inner shaft and including an inflation lumen, and at least one expandable dilator coupled with the distal portion of the shaft in fluid communication with the inflation lumen.

In a related method, locating and dilating a maxillary sinus ostium can involve a maxillary sinus, the method comprising advancing a curved distal portion of a maxillary sinus device into a nasal cavity, wherein a proximal portion of the maxillary sinus device is substantially rigid, passing an atraumatic distal end of the distal portion through the natural ostium of the maxillary sinus, using tactile feedback to confirm passage of the distal end through the ostium and dilating at least one expandable dilator coupled with the curved distal portion of the maxillary sinus device to dilate the natural maxillary sinus ostium.

Additionally, in certain embodiments, the distal tip of the device can light up to provide transillumination.

In certain embodiments, the device can be coupled or used with a variable degree of view endoscope for viewing the maxillary ostium.

These and other advantages and features of the invention will become apparent to those persons skilled in the art upon reading the details of the devices, methods and systems as more fully described below.

BRIEF DESCRIPTION OF THE DRAWING

FIG. 5a is a perspective view of another embodiment of a sinus ostium finder in accordance with the invention shown with a guide wire in a retracted position.

FIG. 5b is a perspective view of the sinus ostium finder of FIG. 4a shown with the guide wire in an extended position.

FIG. 5c is a cross-section of the sinus ostium finder of FIGS. 4a and 4b taken through line A-A.

DETAILED DESCRIPTION

This invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it should be understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a tube" includes a plurality of such tubes and reference to "the shaft" includes reference to one or more shafts and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Figure 1:
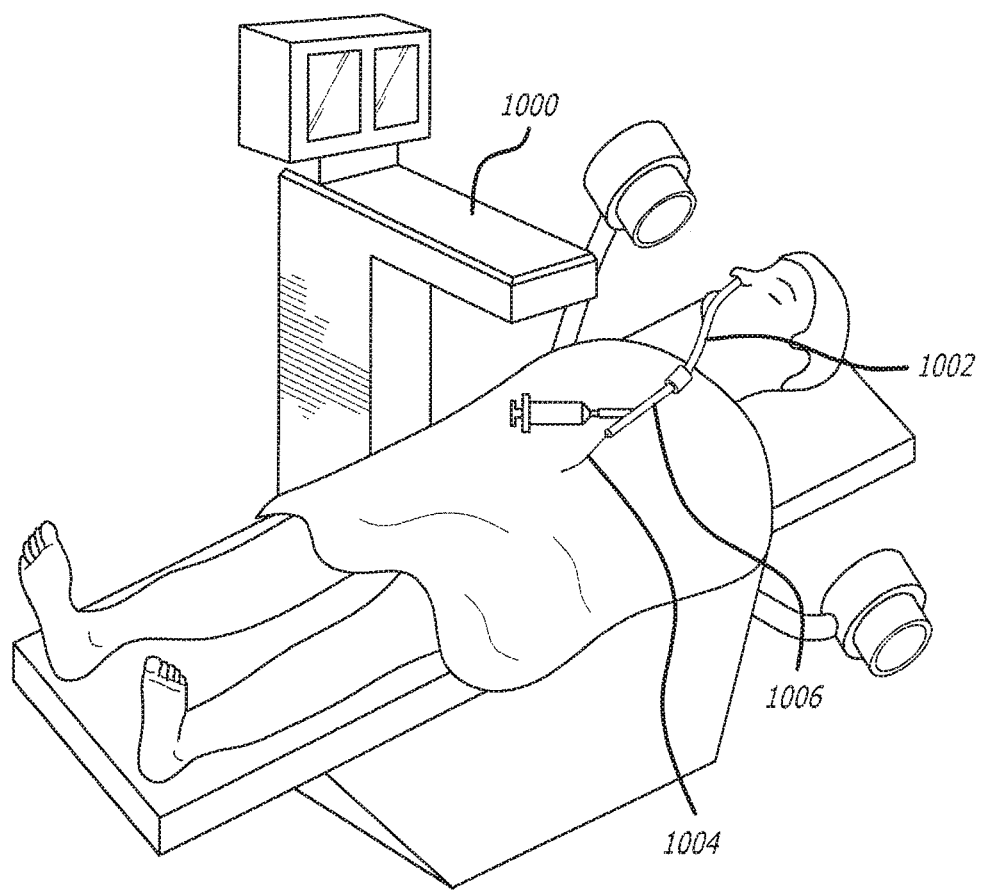
FIG. 1 is an illustration of a patient being treated by a prior art system for catheter-based sinus surgery according to prior art techniques.

Turning now to FIG. 1, an illustration of a patient being treated by a system for catheter-based minimally invasive sinus surgery according to prior art techniques is shown. A C-arm fluoroscope 1000 that is useable to visualize a guide catheter 1002, a guide wire 1002, and a working device 1006 (e.g., a balloon catheter, other dilatation catheter, debrider, cutter, etc.). The guide tube 1002 may be introduced under direct visualization, visualization provided by fluoroscope 1000 and/or from endoscopic visualization, to place the distal end of tube 1002 at a location associated with an ostium of a sinus to be treated. Guide wire 1004 is then inserted through tube 1002 and advanced to extend the distal end of guide wire 1004 to the ostium to be treated. Proper placement often involves advancement and retraction of the distal end of guide wire 1004 until it has been visually confirmed that the guide wire is properly positioned. Working device 1006 is next passed over the guide wire 1004 to the target location where a surgical procedure is to be performed. After performance of the surgical procedure, the working device 1006 is deactivated and withdrawn from the patient, after which the guide wire 1004 and guide catheter 1002 are withdrawn to complete the procedure.

Figure 2A:
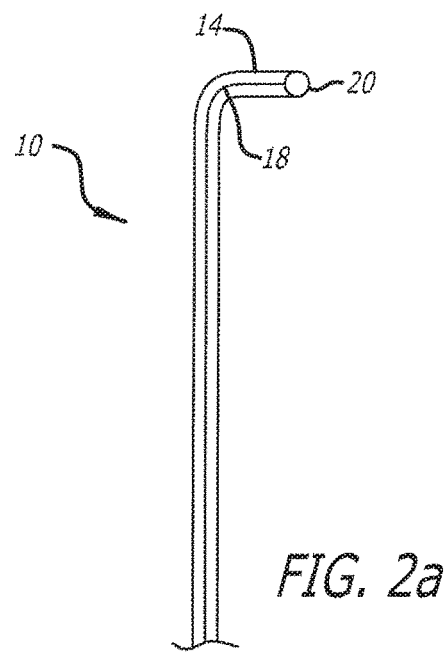
FIG. 2a is a side elevation view of a sinus ostium finder in accordance with the invention shown with a guide wire in a retracted position.
Figure 2B:
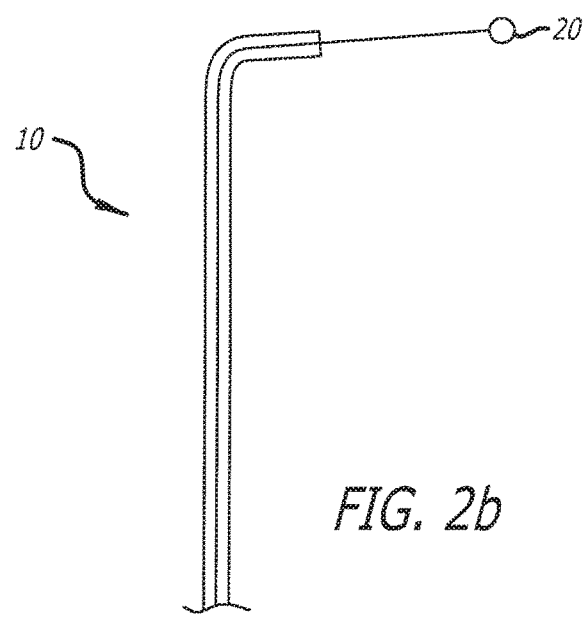
FIG. 2b is a side elevation view of the sinus ostium finder of FIG. 2a shown with a guide wire in an extended position.

Referring now to FIGS. 2a and 2b, a sinus ostium seeker, finder or locator device 10 in accordance with the invention is shown. The sinus finder 10 of the invention comprises a shaft or body 11 having a proximal end 12, a distal end 14, and a curved portion or region 16. Shaft 11 and curved portion 16 define an elongated tubular shape and support a guide wire 18 (FIG. 2b) within an internal channel or cavity (not shown) that extends through shaft 11 and curved region 16 to distal end 14. Curved region 16 may be adjacent to distal end 14 or separated from distal end 14 by a straight or uncurved portion of shaft or body 11. Guide wire 18 is extensible and retractable from shaft 11 through the distal end 14. A probe tip 20 on guide wire 18 is configured for locating a target ostium. Guide wire 18 is shown in a retracted position in FIG. 2a wherein probe tip 20 is adjacent or proximate to distal end 14, and in an extended position in FIG. 2b wherein probe tip 20 is positioned away from distal end 14. Proximal end 12 may be joined to a handle (not shown). The extension and retraction of guide wire 18 may be controlled by application of suitable force to guide wire 18.

Shaft 11 and curved portion 16 are shown as integral portions of a single piece or unit in the embodiment of FIGS. 2a and 2b. In certain embodiments the shaft 11 and curved portion 16 may comprise separate components that are joined together. The curved portion 16 as shown defines an angle of approximately 90 degrees or slightly greater than ninety degrees. This angle may vary as required for different uses of the invention. Preferably, curved portion defines an angle of between about 0 degrees and about 180 degrees, and more preferably between about 0 degrees and about 120 degrees, and providing several iterations at 0 degrees, 30 degrees, 70 degrees, 90 degrees and 110 degrees, or as required to accommodate a particular sinus surgery operation.

Curved portion 16 may be detachable from the remainder of shaft 11 and interchangeable to allow variation of curvature. Curved portion 16 and/or body 11 in many embodiments are resilient to facilitate positioning within a patient's paranasal cavity. In certain embodiments curved portion 16 and shaft 11 are malleable or bendable. In still other embodiments curved portion 16 is resilient or malleable, and shaft 11 is substantially rigid in nature.

Probe tip 20 is structured and configured to facilitate location of a target ostium. In many embodiments probe tip 20 is spherical or oblong in shape, but may be varied in shape as required for different uses of the invention. Probe tip 20 and distal end 14 are structured and configured to provide atraumatic surfaces to minimize trauma or damage to the patient's paranasal cavity. Probe tip 20 may be detachable from guide wire 18 and interchangeable, so that different sized and/or shaped probe tips 20 may be utilized for location of different sinus ostia.

Guide wire 18 may be extended or retracted manually by hand actuated, electric, or air-driven mechanism (not shown), such as a slide, rotatable crank, winch device, reel assembly, or the like. In certain embodiments the extension and retraction of guide wire 18 may be achieved by an electric or air-driven motor (not shown) that is mechanically interfaced with guide wire 18. Guide wire 18 is resilient or flexible in many embodiments to allow the user to easily locate probe tip 20 to a desired location. In certain embodiments guide wire 18 may be bendable or malleable rather than resilient.

Shaft 11, curved portion 16, probe tip 20, guide wire 18, as well as components of the invention in the several embodiments described herein, may be made of various metals or metal alloys, or polymeric materials such as engineering resins, or composite materials thereof, or various combinations of such materials. Preferably biocompatible materials, or coatings of biocompatible materials, are utilized for shaft 11, curved portion 16, probe tip 20 and guide wire 18 to minimize trauma to paranasal cavity tissue that comes in contact with sinus seeker 10. Shaft 11 and curved portion 16 in many embodiments are integral portions of a single component. Shaft 11 and/or curved portion 16 may be malleable, as noted above, such that the angle of curved portion 16 is adjustable by bending to accommodate a particular use. Shaft 11, curved portion 16, probe tip 20 and guide wire 18 and other components of the invention in many embodiments are made of materials that are autoclavable or otherwise sterilizable so that the apparatus 10 or individual components may be re-used. In certain embodiments the shaft 11, curved portion 16, probe tip 20 and guide wire 18 may be made of inexpensive, disposable materials.

Figure 3A:
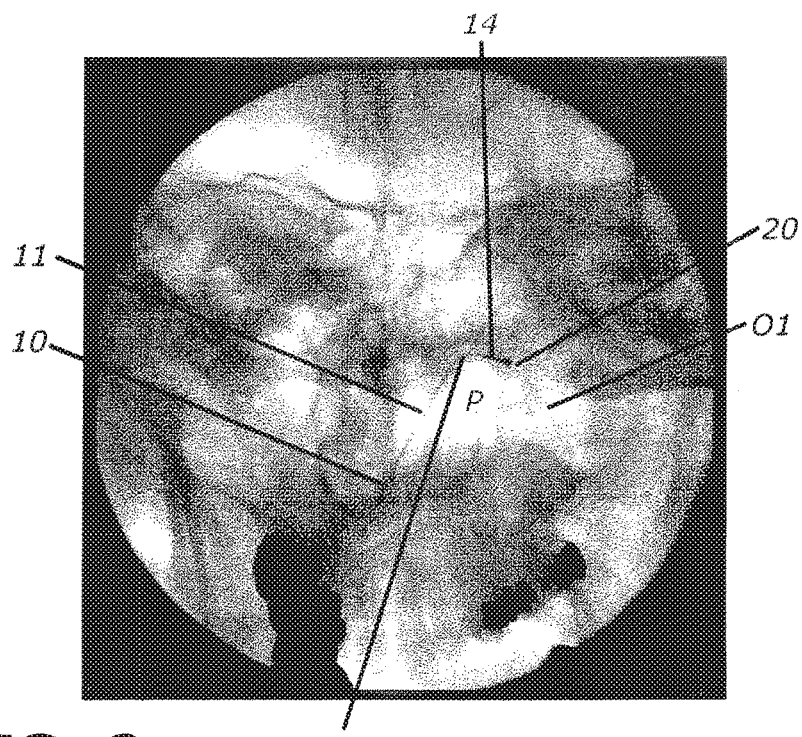
FIGS. 3a and 3b are fluoroscopic images (A-P orientation) showing the sinus ostium finder of FIGS. 2a and 2b locating the left maxillary sinus ostium and deploying a guide wire.
Figure 3B:
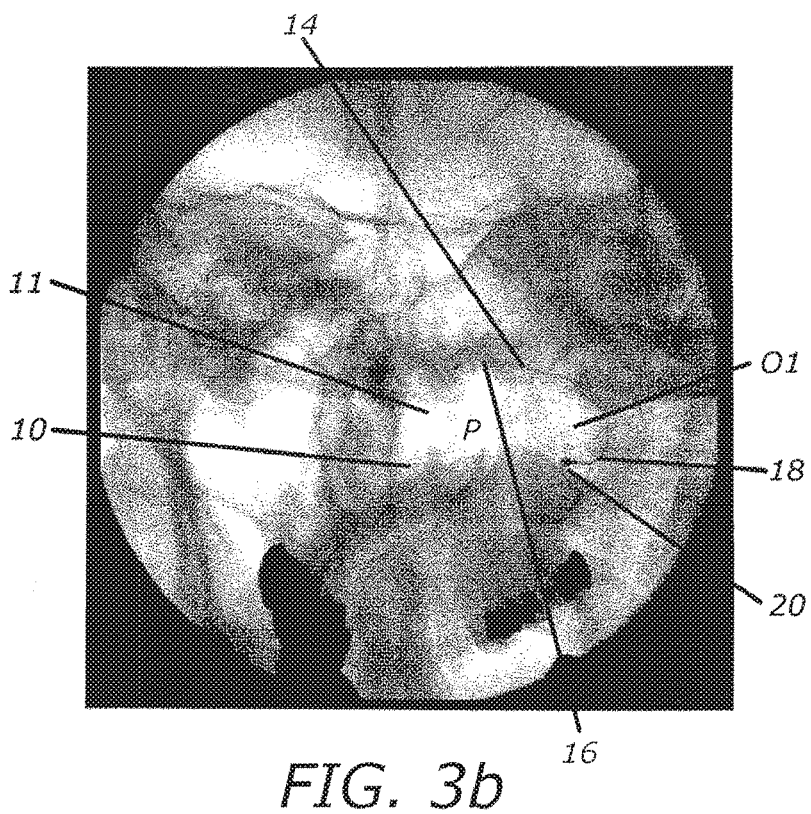

In FIGS. 3a and 3b, the sinus ostium finder 10 is shown fluoroscopically in use to locate the left maxillary sinus ostium O1. The body or shaft 11 of sinus ostium finder is positioned within the patient's paranasal cavity P, and guide wire 18 (FIG. 3b) is extended from body 11 to locate ostium O1. Guide wire 18 is resilient or malleable as noted above, and may undergo flexing or bending over a substantial range of angle. As shown in FIG. 3b, the portion of guide wire 18 adjacent probe tip 20 is approximately parallel with the portion of guide wire 18 adjacent to distal end 14, indicating a flexion angle of approximately 180 degrees in guide wire 18 between distal end 14 and probe tip 20. Once the guide wire 18 has been positioned into the maxillary sinus cavity O1, shaft 11 and curved portion 16 may be removed or withdrawn from the patient's paranasal cavity P while leaving behind the guide wire 18, thus allowing other working devices (not shown) to be introduced over the guide wire 18 and then into the target sinus. In certain embodiments, the sinus ostium finder 10 may include radio-opaque markings (not shown) on shaft 11, curved portion 16, probe tip 20 and/or guide wire 18 to facilitate fluoroscopic visualization of the finder 10 and help in the navigation of finder 11 within the patient's nasal passageway P. The radio-opaque markings may comprise, for example, gradation markings to show dimensions or distances and numerical indicia identifying the gradation markings.

Figure 4A:
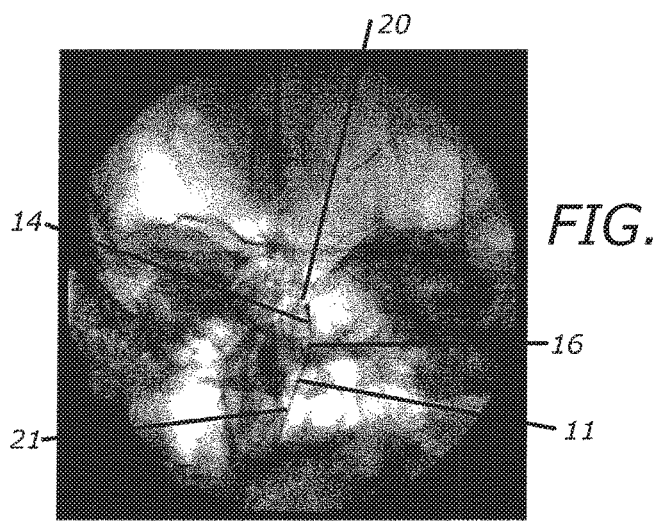
FIG. 4a through FIG. c are fluoroscopic images (A-P orientation) showing another embodiment of a sinus ostium finder locating the left frontal sinus ostium and deploying a guide wire.
Figure 4B:
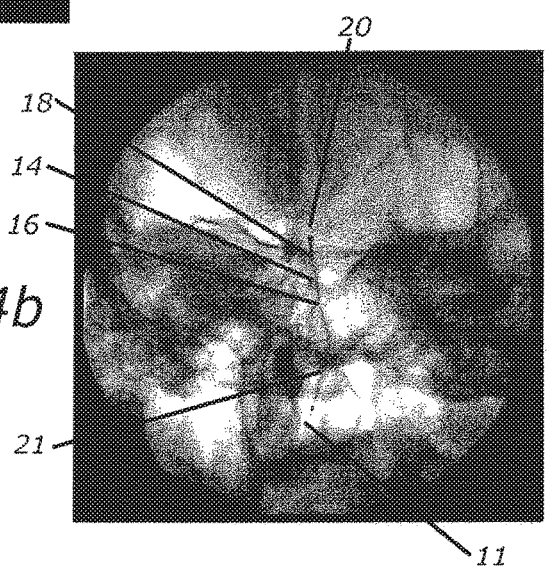
Figure 4C:
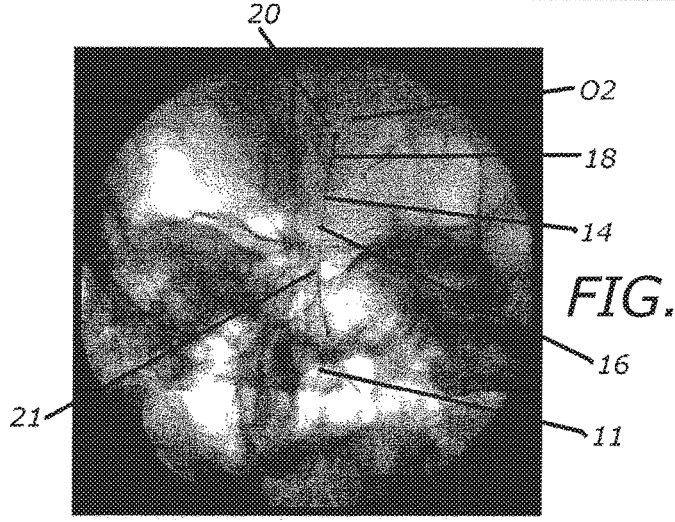

Referring now to FIGS. 4a through 4c, there is shown another embodiment sinus ostium finder 21 in accordance with the invention, with like reference numbers used to denote like parts. The sinus ostium finder 21 is shown fluoroscopically in use to locate the left frontal sinus ostium O2 of a patient. In the embodiment of FIGS. 4a through 4c, the curved region 16 of sinus ostium finder 21 defines an angle of approximately 150 degrees of curvature. The sinus ostium finder 10 of FIGS. 3a and 3b, in comparison, has a curved region 16 that defines an angle of approximately 110 degrees. In other respects the sinus ostium finder 21 is identical to sinus ostium finder 10.

In FIG. 4a, sinus ostium finder 21 is shown inserted into paranasal cavity P, with guide wire (not shown) in a fully retracted position such that probe tip 20 is positioned adjacent distal end 14. In FIG. 4b, guide wire 18 is shown partly extended from distal end 14. In FIG. 4c, guide wire is more fully extended such that probe tip 20 at the end of guide wire 18 is able to locate ostium O2.

FIGS. 5a, 5b and 5c show yet another embodiment of sinus seeker or finder 22 in accordance with the invention, wherein like reference numbers are used to represent like parts. The sinus seeker 22 includes a handle portion 24 having distal and proximal end portions 26, 28 respectively (with only part of the proximal end portion 28 being shown). In the embodiment of FIGS. 5a-5c, handle 24 is of elongated cylindrical configuration and is structured to allow a user to manually adjust the position of shaft 11 and curved portion 16 within a paranasal cavity. Handle 24 is joined to the proximal end 12 of body or shaft 11 at joint 30 by means of internal threading (not shown), snap fitting or other suitable attachment means, and may be detachable from shaft 11 and interchangeable. Alternatively, handle 24 may be made integral with shaft 11. Curved portion 16 is joined to body or shaft 11 at joint 32 by internal threading (not shown), snap fitting or other suitable attachment means, and may be detachable from shaft 11 as noted above. Alternatively, curved portion 16 may be integral with shaft 11.

An interior opening or channel 34 extends longitudinally through handle 24, shaft 11 and curved portion 16, with channel 34 being configured to slidably or movably accommodate guide wire 18. In general, the inner diameter of the longitudinal channel 34 ranges from about 0.5 mm to about 5 mm, and more preferably from about 1 mm to about 3 mm, depending on the size of guide wire 18 utilized with the invention.

Referring more particularly to FIG. 5c, the curved portion 16 of sinus seeker 22 may further comprise a flexible or resilient outer sheath 36 and an internal element 38 within sheath 36. In the embodiment of FIG. 5c, outer sheath 36 is of circular cross-sectional shape, while internal element 38 is of a "U" or "C" cross-sectional shape such that longitudinal channel 34 and guide wire 18 are located between portions or ends 40, 42. Internal element 38 may be removable from sheath 36 and interchangeable. Internal element 38 may be of higher modulus material than sheath 36, such that the curvilinear shape and flexural properties of internal element 38 are imparted to curved portion 16. The material of internal portion 38 may be selected for desired flexural or malleable properties. In many embodiments internal element may also extend through shaft 11, or through shaft 11 and handle. In certain embodiments the outer sheath 36 may comprise a higher modulus material than internal element 38 such that the shape and flexural properties of the curved region are derived from sheath 36 rather than internal element 38. In many embodiments internal element 38 may also extend through shaft 11, or through shaft 11 and handle 24.

Figure 6:
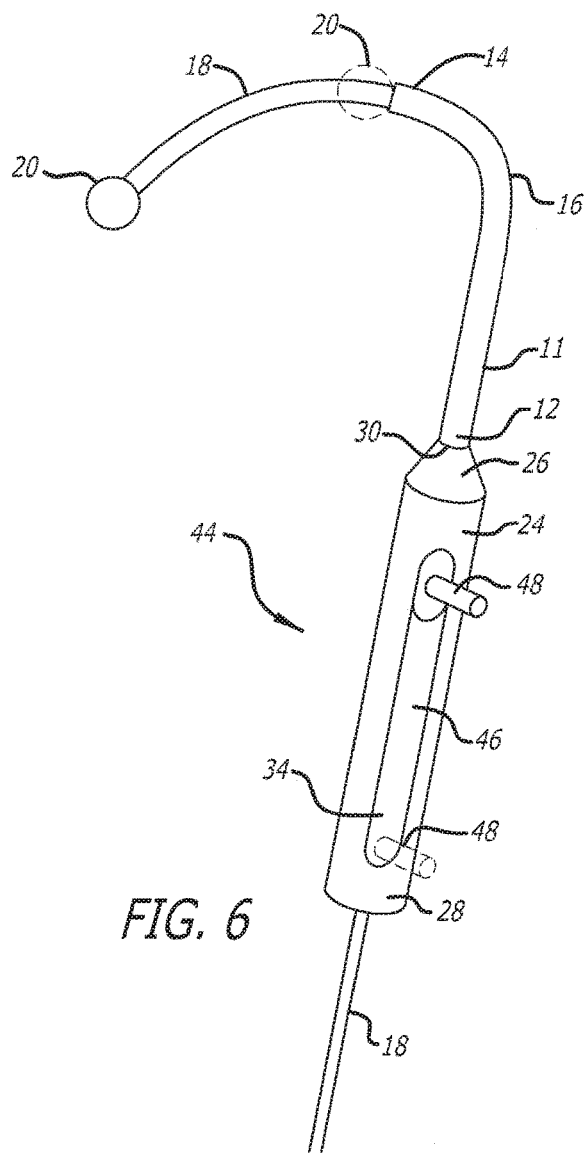
FIG. 6 is a perspective view of another embodiment of a sinus ostium finder in accordance with the invention.

Referring now to FIG. 6, another embodiment of a sinus ostium finder or seeker 44 in accordance with the invention is shown, with like reference numbers used to denote like parts. The handle 24 of sinus seeker 44 is of elongated cylindrical shape and includes a longitudinal slot 46 that communicates with interior channel 34. A knob or actuator element 48 is slidably mounted within slot 46. Knob 48 is mechanically coupled to guide wire 18 such that movement of knob towards distal end 26 of handle 24 advances guide wire 18 and probe tip 20 from distal end 14, as shown in FIG. 6, when actuator 48 is positioned adjacent to distal end of slot 46. Sliding of actuator 48 to the proximal end of slot 46 results in a corresponding retraction of guide wire 18 and probe tip 20, as illustrated in phantom lines.

Figure 7:
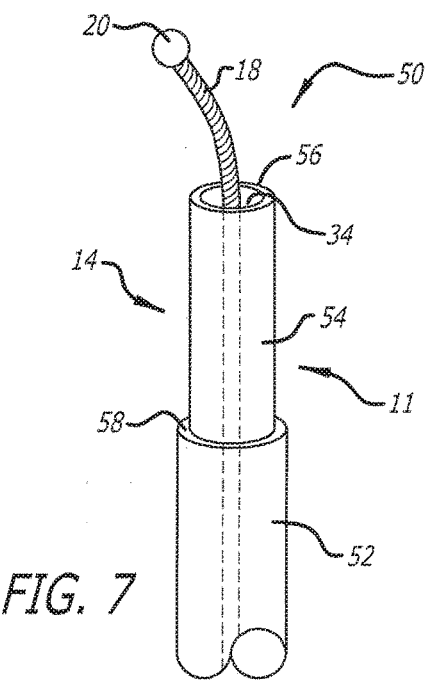
FIG. 7 is a perspective view of the distal end portion of another embodiment of a sinus ostium finder in accordance with the invention.

Referring next to FIG. 7, there is shown a portion of another embodiment of a sinus ostium finder 50 in accordance with the invention. Sinus seeker 50 includes an outer sheath 52 of substantially tubular shape, and an inner sheath 54 positioned within outer sheath 52. Inner sheath 54 is also of substantially tubular shape. A longitudinal channel 34 extends through inner sheath 54 and is structured and configured to slidably accommodate guide wire 18. In the embodiment of FIG. 7, longitudinal channel 34 is of substantially circular cross-sectional shape.

Outer sheath 52 may extend along a portion of, or the entire length of shaft 11, including the curved region (not shown). Inner sheath 54 may likewise extend along a portion of, or the entire length of, the curved portion and shaft. Inner sheath 54 may be slidably extensible and retractable with respect to outer sheath 52, such that during extension the distal end 56 of inner sheath 54 moves away from distal end 58 of outer sheath, and during retraction the distal end 56 of inner sheath 54 approaches distal end 58 of outer sheath 52. The extension and retraction of inner sheath 54 with respect to outer sheath 52 may be controlled by an actuator knob such as knob 48 in FIG. 6.

Inner sheath 54 may be of higher modulus material than outer sheath 52, such that the shape and mechanical properties of inner sheath are imparted to curved portion and/or shaft (not shown) of the sinus seeker 50. In other embodiments the outer sheath 52 may comprise higher modulus material than that of the inner sheath. The material of inner sheath 52 and/or outer sheath may be selected for specific flexural or malleable properties in accordance with the desired use of the invention.

Figure 8:
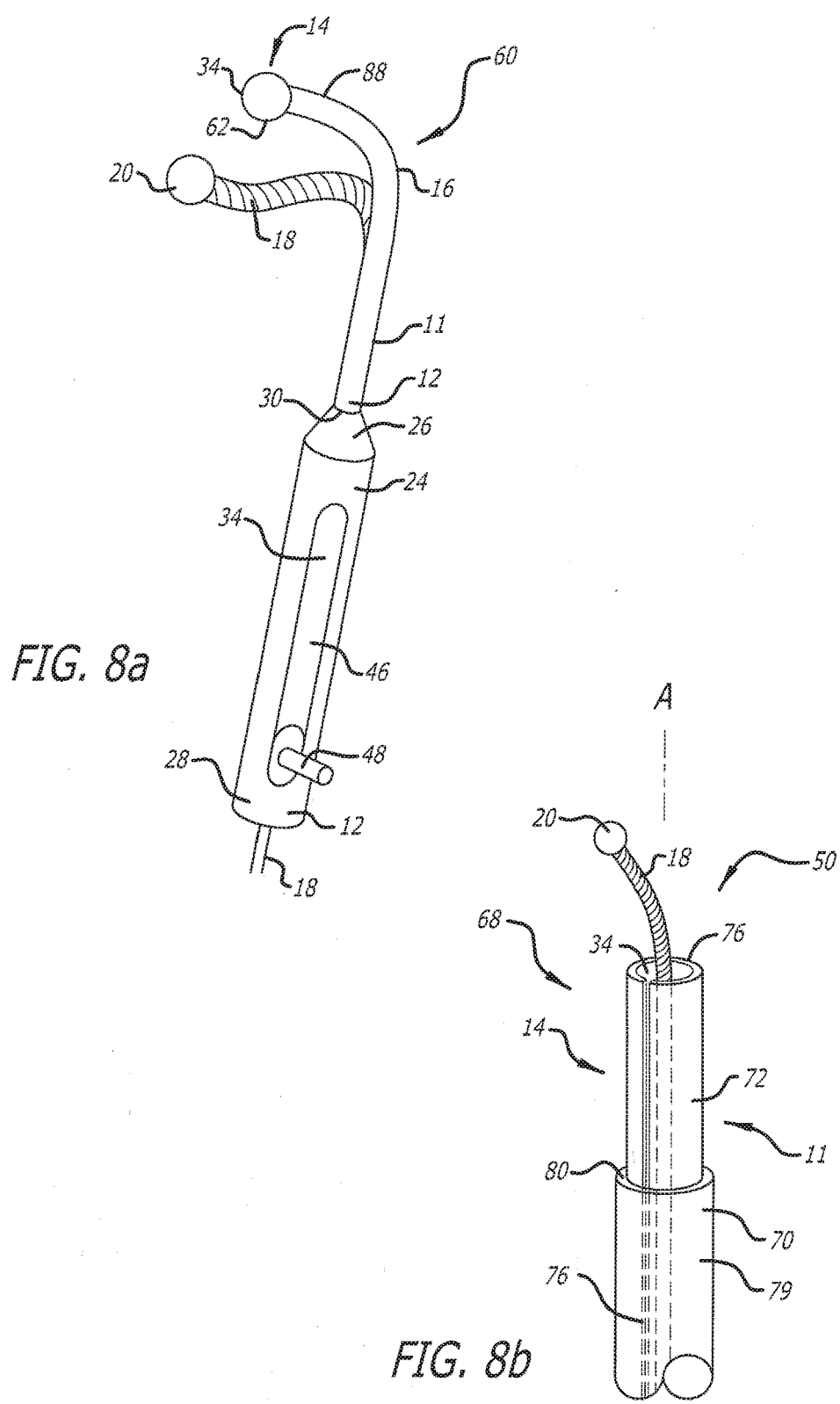
FIG. 8a is a perspective view of another embodiment of a sinus ostium finder in accordance with the invention shown with a guide wire in a partially detached position.
FIG. 8b is a perspective view of a distal end portion of another embodiment of a sinus ostium finder in accordance with the invention.

FIG. 8a shows yet another embodiment of a sinus seeker 60, wherein like reference numbers denote like parts. The distal end 14 of sinus seeker 60 includes a longitudinal slot 62 that communicates with the internal longitudinal channel 34. Slot 62 may extend along the length of all or portion of curved region 16 and shaft 11. Actuation of knob 48 in the manner described above allows guide wire 18 to be advanced or retracted with respect to distal end 14. FIG. 8a shows knob 48 positioned adjacent to proximal end 28 of handle 24, corresponding to a retracted position for guide wire 18.

Slot 62 allows guide wire 18 to be removed from channel 34 through slot 62, as well as by extension from distal end 14. Curvilinear portion 16 in this regard may be made of resilient material such that guide wire 18 is retained within channel 34 under normal conditions, but can "snap" out of slot 62 to disengage from channel 34 upon application of a lateral force to guide wire 18. As shown in FIG. 8a, guide wire 18 is partially disengaged from channel 34 and slot 62. Disengagement of guide wire 18 through slot 62 as provided by sinus seeker 60 facilitates removal and interchanging of guide wire 18 and probe tip 20, and facilitates removal of shaft 11, curved portion 16 and distal end 14 from a target sinus or adjacent regions of the paranasal cavity while leaving guide wire 18 and probe tip 20 in place. A working device (not shown) may then be directed along guide wire 18 to the target sinus to carry out surgical procedures.

In the embodiment of FIG. 8a, shaft 11 is extensible and retractable with respect to handle 24. A sleeve or collar 64 supports shaft 11 and may be tensioned by means of a screw or threaded parts (not shown) to secure shaft in place. Loosening of collar 64 allows shaft 11 to be extended or retracted from collar 64 and handle 24 to provide a different length and configuration to sinus seeker 60. Once shaft 11 has been adjusted to a desired length by extension or retraction from handle 24, collar 64 may be tensioned to retain the adjusted position of shaft 11.

FIG. 8b shows a distal portion of another embodiment of a sinus ostium finder 68 in accordance with the invention. The apparatus 68 includes an outer sheath 70 of substantially cylindrical or tubular shape, and an inner sheath 72 substantially cylindrical or tubular shape positioned within outer sheath 70. A longitudinal channel 34 extends through inner sheath 72 and is structured and configured to slidably accommodate guide wire 18. In the embodiment of FIG. 8b, longitudinal channel 34 is of substantially circular cross-sectional shape.

A longitudinal slot 74 extends through inner sheath 72 and communicates with longitudinal channel 34. Slot 74 permits guide wire 18 to be removed from channel 34 in a lateral direction upon exertion of a lateral force on guide wire 18. Outer sheath 70 may also include a longitudinal slot 76, which extends through outer sheath 72 to communicate with longitudinal slot 74 and hence longitudinal channel 34. Thus, guide wire 18 may be removed laterally from inner and outer sheaths 72, 70 via slots 74, 72 upon application of a suitable lateral force on guide wire 18.

In the embodiment of FIG. 8b longitudinal slots 74, 76 are aligned so that both slots 74, 76 communicate with internal channel 34 to allow insertion and release of guide wire 18 from channel. In certain embodiments one or both of the inner sheath 72 and outer sheath 70 may be rotatable with respect to each other along the longitudinal axis A of the shaft and curved region (not shown) of the apparatus 68. Inner sheath 72, outer sheath 70, or both may be mechanically coupled to a rotational adjustment mechanism on the handle (not shown of the apparatus 68, so that the rotational position of sheath 70 and/or sheath 72 may be rotatably adjusted to control alignment of slots 74, 76. Thus, when one of sheaths 70, 72 is rotated with respect to the other, slots 74, 76 may be moved out of alignment so that guide wire 18 cannot be removed through slots 74, 76, or aligned as shown in FIG. 8b so that guide wire 18 can be removed from channel 34 through slots 74, 76.

Outer sheath 70 may extend along a portion of, or the entire length of, the curved portion and shaft (not shown in FIG. 8b) of the sinus seeker apparatus 68. Inner sheath 72 may similarly extend along a portion of, or the entire length of, the curved portion and shaft. Inner sheath 72 may be slidably extensible and retractable with respect to outer sheath 70, with distal end 78 of inner sheath 72 moving away from distal end 80 of outer sheath 70 during extension, and with distal end 78 moving towards distal end 80 during extension.

Figure 9:
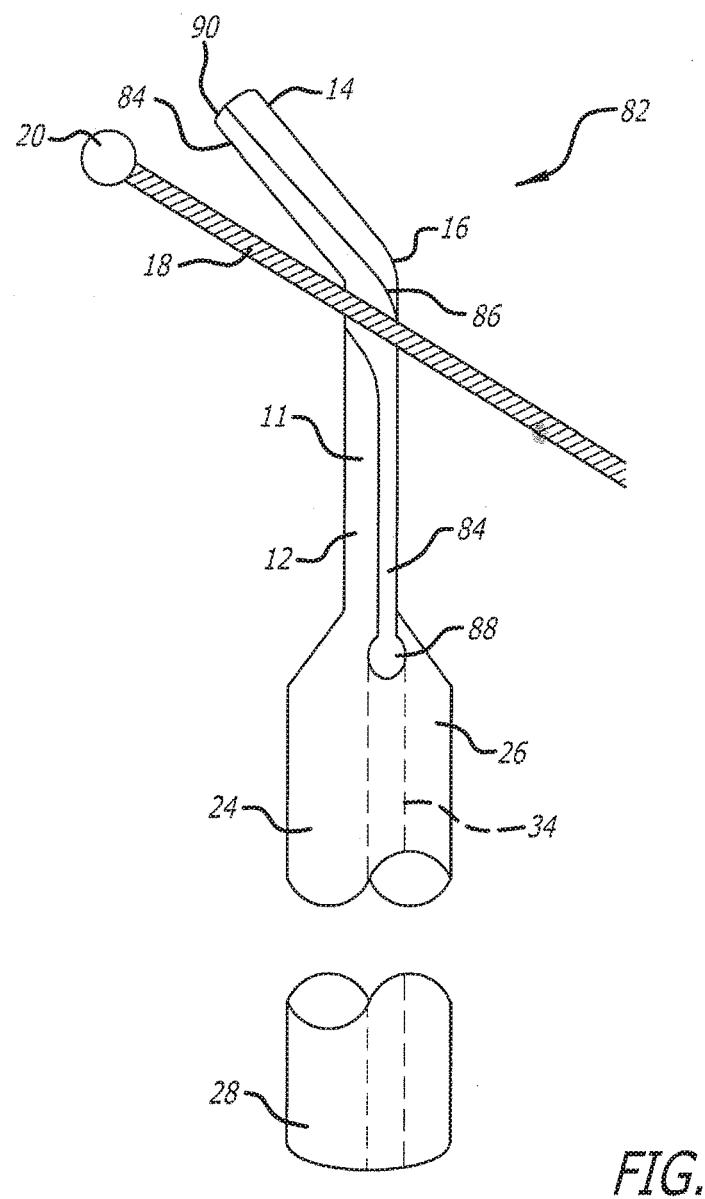
FIG. 9 is a partial perspective view of another embodiment of the sinus ostium finder of the invention.

FIG. 9 illustrates still another embodiment of a sinus ostium seeker 82 in accordance with the invention, wherein like reference numbers denote like parts. The apparatus 82 includes a longitudinal slot 84 that extends from distal end 14 to the distal end 26 of handle 24. Longitudinal slot 84 communicates with longitudinal channel 34, which extends through handle 24, shaft 11 and curved region 16 to distal end 14. Slot 84 includes a laterally curving region 86 such that the end 88 of slot 84 adjacent handle distal end 26 has a different angular orientation (relative to a central axis passing through the shaft 11) than the end 90 of slot 84 adjacent distal end 14 with respect to shaft 11 and curved region 16, such that slot 84 "twists" relative to shaft 11 as it traverses from its distal end to its proximal end. Thus, in FIG. 9, the portion of slot 84 adjacent slot end 88 is rotated from the portion of slot 84 adjacent end 90 with respect to the longitudinal axis (not shown) defined by shaft 11 and curved portion 16. The laterally curving region 86 of slot 84 facilitates the insertion and removal of guide wire 18 into or out of interior longitudinal channel 34.

Figure 10A:
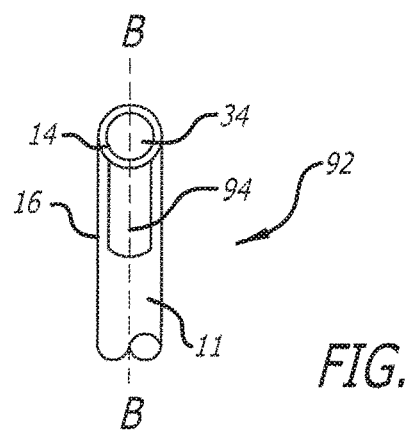
FIG. 10a is a front elevation view of a distal end portion of another embodiment of the invention, shown without the guide wire.
Figure 10B:
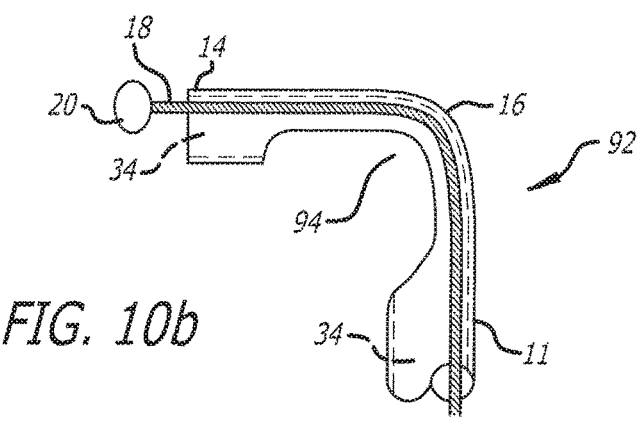
FIG. 10b is a longitudinal sectional view taken through line B-B of the distal end portion of FIG. 10a shown with a guide wire positioned within the internal longitudinal channel.
Figure 10C:
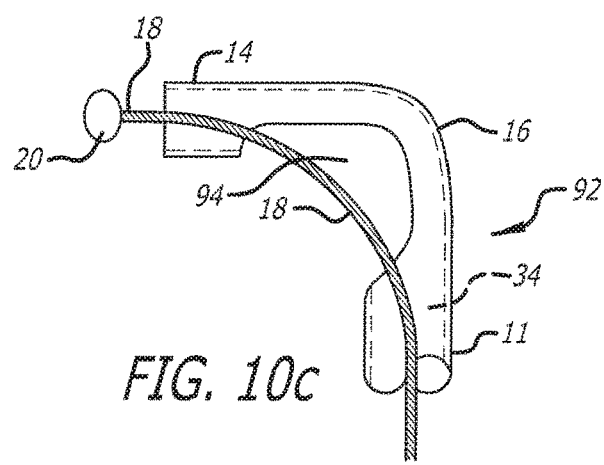
FIG. 10c shows the distal end portion of FIG. 10b with the guide wire partially removed from the internal longitudinal channel.

Referring now to FIG. 10a through 10c, a distal portion of another embodiment of a sinus ostium finder 92 in accordance with the invention is shown, with like numbers used to denote like parts. The apparatus 92 includes an opening 94 that extends longitudinally from distal end 14 across curved portion 16 to shaft 11. Opening 94 communicates with internal longitudinal channel 34. Opening 94 is structured and configured to allow a user to grasp guide wire 18 through opening 94, using fingers, forceps or other grasping tool (not shown). Opening 94 facilitates the removal of guide wire 18 from the channel 34 and the apparatus 92. In this way, the proximal end (not shown) of the guide wire can be loaded into the distal end 14 of the shaft 11 where the cutout 94 in the bend helps pass a stiff proximal end of the guidewire into the body of the guide catheter despite the sharp bend angle of the curved tip. Thus, the guidewire can take a less severe bend during loading. Once loaded, the system is configured as shown in FIG. 10B. After the system is used to place the tip of the guide wire into the sinus, the guide catheter can be pulled back off the proximal end of the guide wire.

Figure 11A:
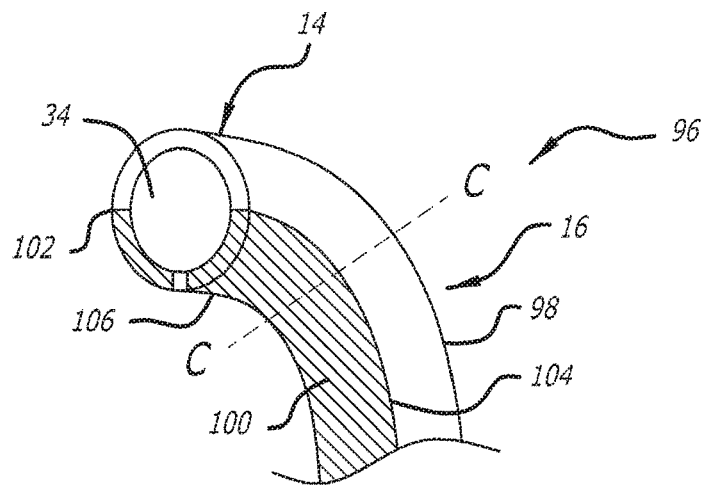
FIG. 11a is a perspective view of the distal end portion of another embodiment of a sinus ostium seeker in accordance with the invention shown without a guide wire.
Figure 11B:
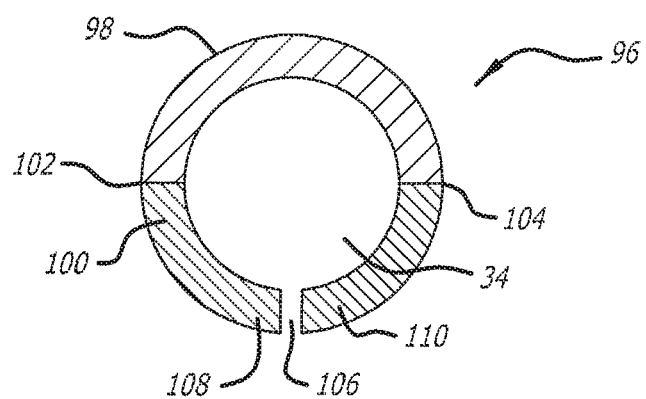
FIG. 11b is a cross-sectional view of the distal end portion of FIG. 11a taken through line C-C.

FIGS. 11a and 11b show a distal portion of another embodiment of a sinus ostium finder 96 in accordance with the invention, with like reference numbers used to denote like parts. The apparatus 96 includes an elongated back portion 98 and an elongated front portion 100 that are joined together along seams 102, 104 by adhesive, heat welding or other bonding means. Back and front portions 98, 100 together define a tubular shape, with an interior channel 34 of circular cross-sectional shape between the front and back portions 98, 100. Front and back portions 98, 100 extend from distal end 14 along curved region 16 and shaft (not shown), and together define the curved region 16 and shaft (not shown) of the apparatus 96. A longitudinal slot 106 in front portion 100 communicates with interior channel 34. In the embodiment of FIGS. 11a and 11b, front and back portions 100, 98 each are semicircular in cross-sectional shape and impart a circular cross-sectional shape to interior channel 34.

In many embodiments back portion 98 is made of a rigid or substantially rigid higher modulus material, while front portion 100 comprises a resilient lower modulus material. The resilient nature of front portion 100 allows a guide wire (not shown) to "snap fit" through slot 106 between ends 108, 110 (FIG. 11b). The guide wire thus can be easily inserted into and removed from channel 34 by application of a suitable force against front portion 100 to force or move the guide wire through slot 106. In certain embodiments both front and back portions may comprise flexible materials.

Figure 12A:
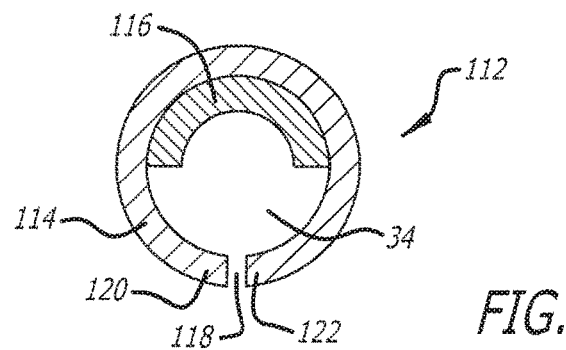
FIG. 12a is a cross-sectional view of a distal end portion of another embodiment of a sinus seeker apparatus in accordance with the invention shown without a guide wire.
Figure 12B:
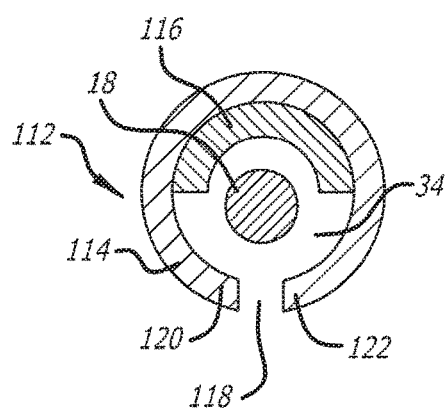
FIG. 12b shows the distal end portion of FIG. 12a with a guide wire.
Figure 12C:
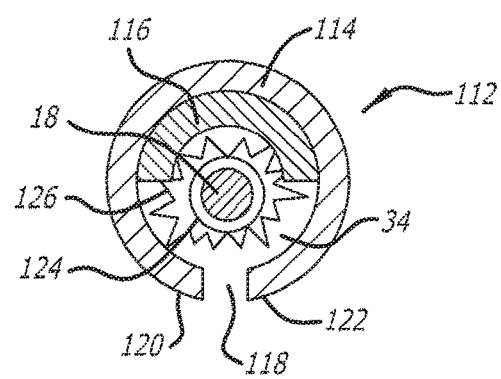
FIG. 12c shows the distal end portion of FIG. 12b including a lubricant.

FIGS. 12a through 12c provide cross-sectional views of a portion of yet another sinus ostium finder 112 in accordance with the invention, with like numbers used to denote like parts. The apparatus 112 includes an outer sheath 114 and an inner section or portion 116 positioned within sheath 114. Sheath 114 is of elongated tubular configuration and defines an interior channel 34 that extends longitudinally through the curved region and shaft (not shown) of the apparatus 112. Inner section 116 fits within channel 34 and extends along all or a portion of the shaft and curved region. A slot 118 extends longitudinally along sheath 114 and communicates with interior channel 34. In the embodiment shown in FIGS. 12a through 12c, sheath 114 is of circular cross-sectional shape and inner section 116 is of arcuate or semicircular cross-sectional shape such that the cross-sectional shape of inner section 116 conforms to the cross-sectional shape of sheath 114. A guide wire 18 (FIGS. 12b and 12c) fits within channel 34.

Sheath 114 is made of resilient material such that guide wire 18 can be forced between ends or portions 120, 122 through slot 188 and into channel 34. Guide wire 18 then is retained within channel 34 until a suitable force is applied to wire to bring wire through slot 118 between ends 120, 122 and out of channel 34. Inner section 116 in many embodiments is made of a rigid or substantially rigid material, or a material of higher modulus than that of sheath 114.

A coating 124 (FIG. 12c) of biocompatible low friction coefficient material such as TEFLON™ may be included on guide wire 18 to facilitate sliding motion of guide wire 18 within channel 34 and to reduce or minimize possible trauma to a patient's paranasal cavity. A lubricating oil or gel 126 (FIG. 12c) may be included within channel 34 to facilitate movement of guide wire 34 within channel 34.

Figure 13:
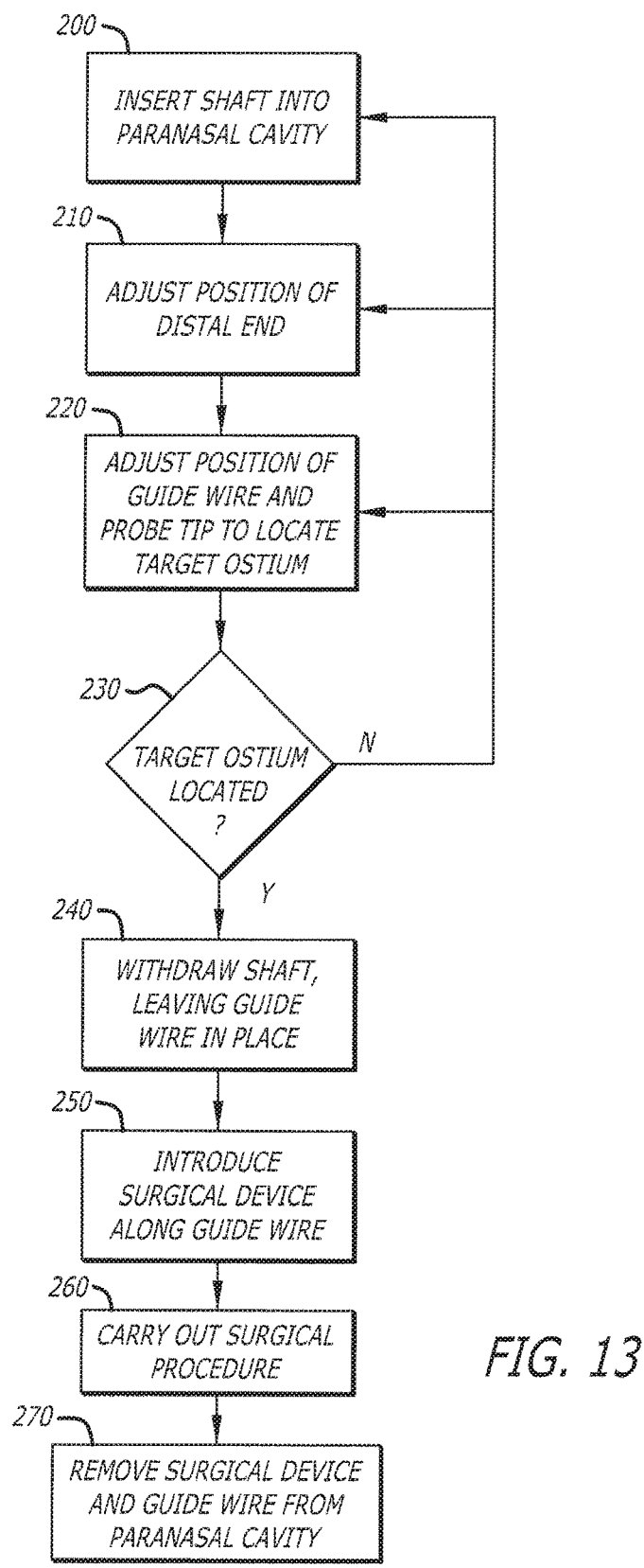
FIG. 13 is a flow chart illustrating one embodiment of the methods of the invention.

The methods of the invention will be more fully understood by reference to the flow chart of FIG. 13, as well as FIGS. 2-12. The sequence of the events described below may vary and should not be considered limiting. Not all events described may occur in a particular use of the invention, and in certain embodiments additional events not shown in FIG. 13 may be carried out.

In event 200, the shaft 11 of the sinus ostium finder of the invention is inserted into a patient's paranasal cavity. As shown in FIGS. 3 and 4, this event is carried out by inserting distal end 14, followed by curved region 16 and shaft 11 into paranasal cavity P. The insertion may be carried out by a surgeon or other medical personnel, and may be monitored fluoroscopically and/or endoscopically, or may be carried out without visualization tools.

In event 210, the position of distal end 14 is adjusted. In many embodiments the adjustment is carried out manually, positioning distal end 14 by suitable manual positioning of handle 24. The positioning of distal end 14 in many embodiments is monitored fluoroscopically, so that the distal end 14, as well as shaft 11 and curved region 14 may be visualized. It is to be recognized that alternatively, such positioning can be visualized solely by endoscopic visualization. The adjustment of the position of distal end 14 is carried out with the goal of locating a target sinus ostium in the event(s) below. In certain embodiments radio-opaque markings or markings provided by visually contrasting colors may be included on distal end 14, shaft 11 and/or curved region 16 to assist in locating the target ostium.

In event 220, the position of guide wire 18 and probe tip 11 is adjusted by extension of guide wire 18 from distal end 14 until probe tip 20 approaches or reaches the target ostium. The positioning of guide wire 18 and probe tip 20 is generally monitored fluoroscopically, so that the position of probe tip 20 with respect to the target ostium may be visualized. In certain embodiments radio-opaque and radio-transparent markings may be included on probe tip 20 and/or guide wire 20 to assist in locating the target ostium.

In event 230, a determination is made whether or not the target ostium has been located. The determination is made by visually such as endoscopically, fluoroscopically or using light-emitting transillumination to observe the location or position of probe tip 20 with respect to the target ostium. In many embodiments the probe tip 20 is selected to have a diameter that matches that of the target ostium, and location of the target ostium is determined by exactly fitting the probe tip 20 into the target ostium. If the target ostium has been located, event 240 is carried out.

If it is determined in event 230 that the target ostium has not been located, event 220 may be repeated by again adjusting the position of guide wire 18 and probe tip 20. This may be carried out by retracting guide wire 18 towards distal end 14, and then re-extending guide wire 18 from distal end 14 to adjust the position of guide wire 18 and probe tip 20 and direct probe tip 20 towards the target ostium.

In certain instances where it is determined in event 230 that the target ostium has not been located, both events 210 and 220 are repeated. Thus, guide wire 18 is retracted, the position or orientation of distal end 14 is adjusted by manually positioning the sinus ostium finder apparatus, and then guide wire 18 is again advanced to adjust the position of guide wire 18 and probe tip 20.

In still further instances where it is determined in event 230 that the target ostium has not been located, events 200 through 220 may be repeated. In such instances guide wire 18 would be retracted, and the sinus ostium finder withdrawn from the paranasal cavity. Then, a different, more suitably configured sinus ostium finder would be re-inserted into the paranasal cavity and events 210 through 230 are repeated. Alternatively, the probe tip 20 may be removed from guide wire and a differently sized or shaped probe tip 20 may be introduced to guide wire, after which events 210 through 230 are repeated.

At event 240, shaft 11 (including curved region 16 and distal end 14) is removed from the paranasal cavity while leaving guide wire 18 and probe tip 20 in place in their adjusted position. In embodiments of the invention wherein the shaft 11 includes a slot, guide wire 18 may be disengaged from the slot prior to removal of the shaft 11.

In event 250, a surgical or working device or devices are introduced along the guide wire 18 and directed along the guide wire 18 to the target ostium. Such devices may comprise, for example, catheters, cannula, tubes, dilators, balloons, substance injectors, needles, penetrators, cutters, debriders, microdebriders, hemostatic devices, cautery devices, cryosurgical devices, heaters, coolers, scopes, endoscopes, light guides, phototherapy devices, drills, rasps, saws, and the like.

In event 260 a surgical or other procedure is carried out using the working device introduced in event 250.

In event 270, the working device and guide wire are withdrawn from the paranasal cavity.

Figure 14:
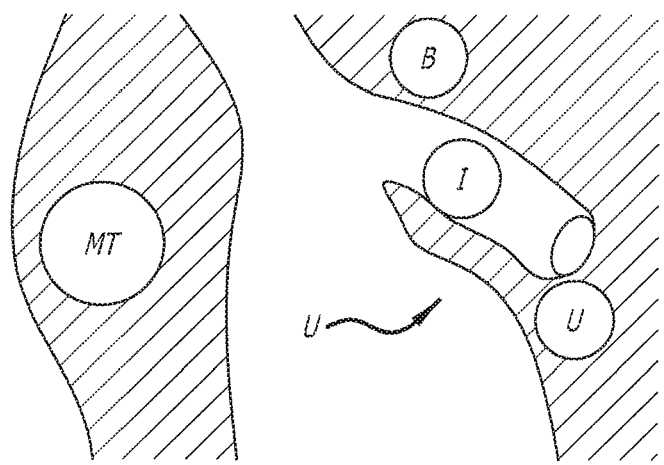
FIG. 14 is a cross-sectional view of anatomy proximate a maxillary sinus.
Figure 15:
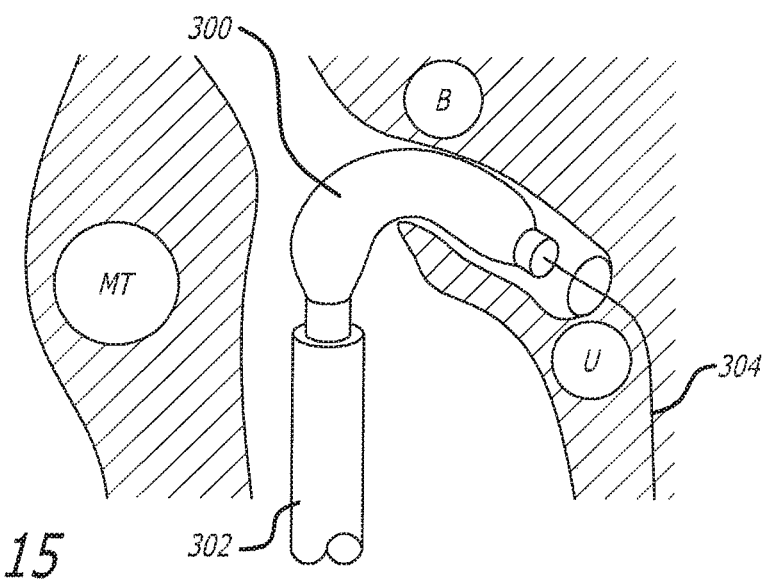
FIG. 15 is a cross-sectional view depicting use of a guide, guide wire and balloon catheter for treating a maxillary sinus.

Referring now to FIGS. 14 and 15, in a related approach, various embodiments may provide for dilating and/or remodeling a sinus ostium and/or a transitional space leading to an ostia. In particular, the devices, systems and methods described below are directed to remodeling a maxillary sinus ostium and/or a transitional space leading to a maxillary ostium. In alternative embodiments, ostia and/or transitional spaces of other paranasal sinuses may be dilated. Dilating or remodelling a transitional space may mean dilating a general anatomical area in the vicinity of an ostium and/or moving one or more anatomical structures in that general anatomical area. Such dilation or remodelling may in some cases facilitate or enhance flow of air, mucus and/or other substances into and/or out of a maxillary sinus.

With reference to FIG. 14, the nasal/paranasal cavity outside the maxillary sinus has a transitional space formed by and including the anatomical structures and spaces called the infundibulum I, the uncinate process U, the ethmoid bulla B, the middle turbinate MT and the middle meatus. In various embodiments, any of these structures may be moved and/or any of these areas may be dilated.

Referring now to FIG. 15, the anatomy of the maxillary sinus transitional space, like that of the paranasal cavity and the sinuses themselves, consists of bone and mucosa. Flexible and rigid instruments may be conceived to remove obstruction in the transitional space. As shown in FIG. 15, one flexible embodiment may involve a balloon catheter 300. The area may be accessed using a guide 302 and guidewire 304 and the balloon catheter 300 may be positioned in the transitional space and inflated. However, this approach requires the coordinated use of several devices. The approach may further require multiple guides 302 to position the balloon 300 appropriately.

Figure 16:
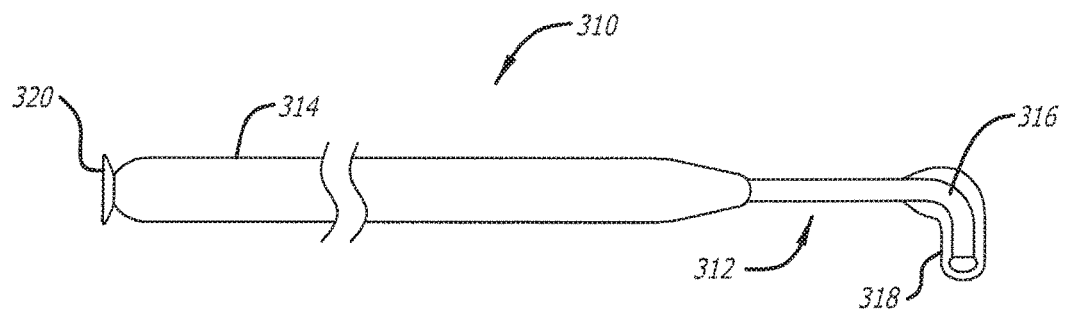
FIG. 16 is a side view of one embodiment of a probe device with a dilator.
Figure 17A:
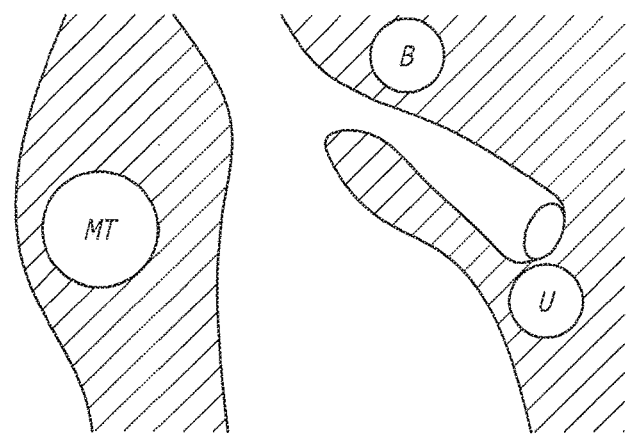
FIGS. 17a-d are cross-sectional views depicting treating a maxillary sinus with the device of FIG. 16.
Figure 17B:
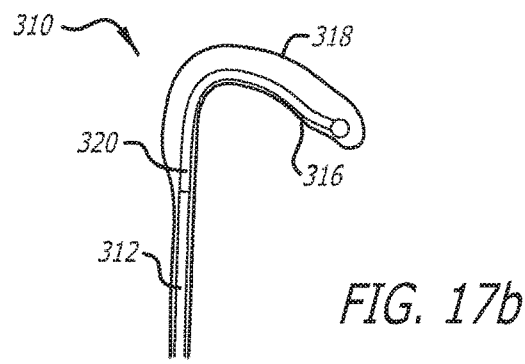
Figure 17C:
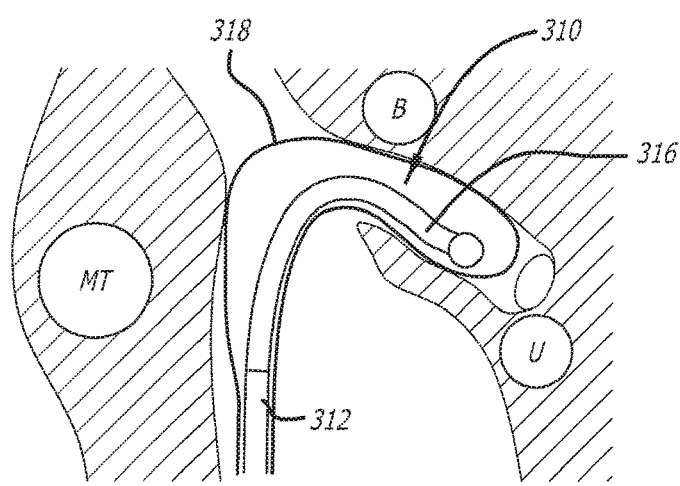
Figure 17D:
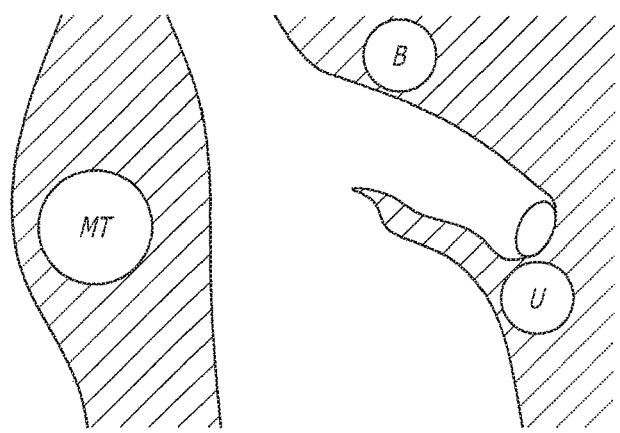

Referring now to FIG. 16, a simplified probe device 310 can include a malleable or semi-rigid region 312 extending from a handle 314. The probe tip 316 can be curved and is contemplated to embody a dilator 318 such as a balloon. A proximal end of the handle 314 is equipped with a luer 320 for accepting an inflation device operable to expand the dilator 318. In this configuration, the curve of the probe tip 316 may be adjusted to optimize access behind the uncinate and in the transitional space leading to the maxillary sinus. When an inflation device (not shown) is attached the balloon can be inflated, creating space in the transitional area as well as dilating the maxillary sinus ostium. This device may be used as a single hand instrument under direct vision, fluoroscopy, and/or image guidance. Guides and guidewires may be adapted for use therewith but may not be necessary.

The balloon dilator 318 of the probe device 310 may have various attributes and configurations. For example, the balloon 318 may be non-compliant, semi-compliant, or compliant. Further there may be one or several balloons, and the balloons may be concentric or non-concentric. Moreover, the contemplated balloon 318 may have multiple diameters and lengths, multiple taper geometries, and it may end at or before the distal tip of the probe, or extend beyond the probe. The balloon 318 may also have modified frictional properties to release or gain traction on anatomy, such as a non-slip surface. In various embodiments, the balloon 318 may have round or non-round cross-sectional geometries to assist re-wrap and profile.

In one contemplated approach, as shown in FIGS. 17a-d, the balloon 318 may be non-concentric and may be oriented to inflate on the outside of the curve 316 of the probe 310. The balloon 318 may relatively long, extending from the medial shaft 320 to beyond the probe tip 316. When inflated, the balloon 318 does not push the uncinate U. However, the balloon is configurable to push medially on the middle turbinate MT and posteriorly on the bulla B, thereby opening the transitional space (See FIGS. 17c and d). The balloon 318 may also extend beyond the probe tip 316 to ensure that the infundibulum has been remodeled and to exert medial force on the middle turbinate MT.

In another example, a concentric and relatively short balloon (not shown) may push the uncinate U anteriorly and may have some posterior impact on the bulla B. There would not necessarily be an impact on the middle turbinate MT. In alternative embodiments, the same or similar devices may be used to remove or reduce obstruction in the frontal and sphenoid transitional spaces. When used in conjunction with a viewing device, the physician may be able to open the transitional space for the maxillary sinus and visually confirm if the ostium is open or closed. If the ostium is closed, the surgeon may opt to use traditional sinuplasty devices or other methods. If the ostium is open, then removal of obstructions in the transitional space may be a sufficient treatment.

Figure 18A:
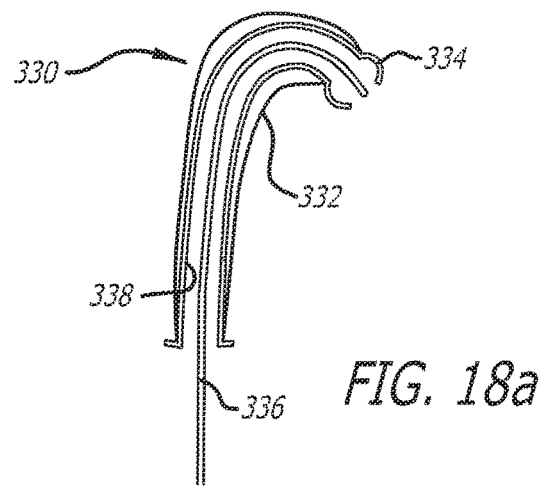
FIGS. 18a-c are partial cross-sectional views depicting use of a probe over a shaped mandrel.
Figure 18B:
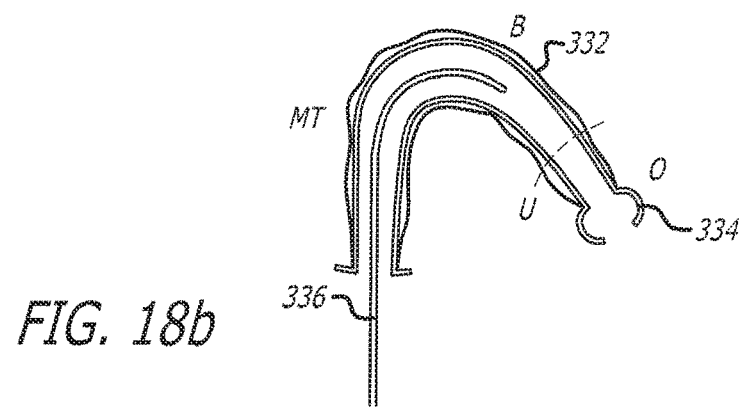
Figure 18C:
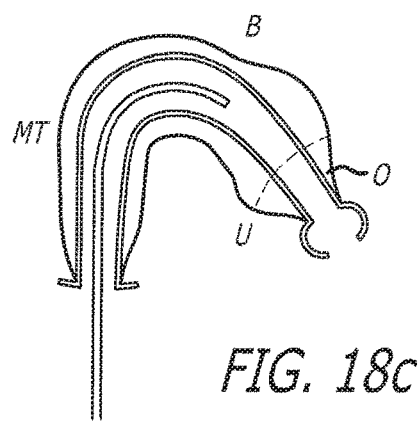

As shown in FIGS. 18a-c, another probe device 330 for dilating the infundibulum, bulla, and/or middle turbinate, as well as the maxillary ostium, is shown. In particular, probe device 330 is configured to first access the maxillary ostium by tactile feel. Next, a member is advanced through the maxillary ostium and then employed to dilate the anatomical structures in the area. Here, the probe device 300 includes a balloon 332 configured with a ball tip 334. The device 330 is further configured to receive a shaped mandrel 336 within an interior lumen 338.

As shown in FIG. 18b, the balloon portion 332 is advanced over the mandrel 336, the mandrel 336 directing the balloon 332 transversely. By using this structure, the balloon 332 passes through the maxillary ostium O. Next, the balloon 332 is dilated, which consequently pushes the middle turbinate MT medially and the bulla B posteriorly. The dilation also opens the ostium O and infundibulum, whereas the uncinate is pushed anteriorly. The mandrel 336 enables the probe device 330 to tolerate the dilation pressure used to expand the balloon 332 without using a guidewire.

The interior lumen 338 or the probe device 330 is constructed to allow retraction over the mandrel 336 without kinking. The mandrel 336 itself could be spring tempered or malleable. The mandrel 336 may also have a short coil or soft tip to reduce kinking of the inner member during balloon retraction. The mandrel 336 may further be constructed of a shape memory alloy which would conform to the balloon 336 geometry when inflated. This may also help in reducing stress on the interior lumen 338 and kinking during balloon retraction.

In an alternative embodiment, the probe device 320 may be modified to address the sphenoid or frontal paranasal sinuses by using a substantially straight or less severely curved mandrel, respectively. In some embodiments, an optional sheath (not shown) may be integrated onto a shaft of the probe to help re-wrap the balloon and thus reduce the overall profile of the balloon after dilation and deflation.

In some embodiments, the probe device 320 facilitates the use of tactile feel and balloon advancement to confirm ostial access. This is generally desirable when using the device in the maxillary and sphenoid sinuses and/or their transitional areas, but it may not work as well in the frontal sinus. Several additional means of confirmation may also be adapted. For example, a fluid may be flushed through a lumen of the probe device 336. If the fluid is seen endoscopically in the nasal cavity, it can be assumed that the device has not entered the sinus. Alternatively, light fibers may be added to the tip of the device to transilluminate a sinus. This addition of light fibers and transillumination may be used in the maxillary, sphenoid or frontal sinus.

In another embodiment, an image guidance sensor may be fixed to the tip of the probe device 320 and tracked with an electro-magnetic system. This would provide confirmation for each of the sinuses. Fluoroscopy could also be used to confirm access. Likewise, a flexible fiber scope could be passed down the center of the probe device 320 to visualize the area if the tip of the device 320 has entered the target sinus.

Figure 19A:
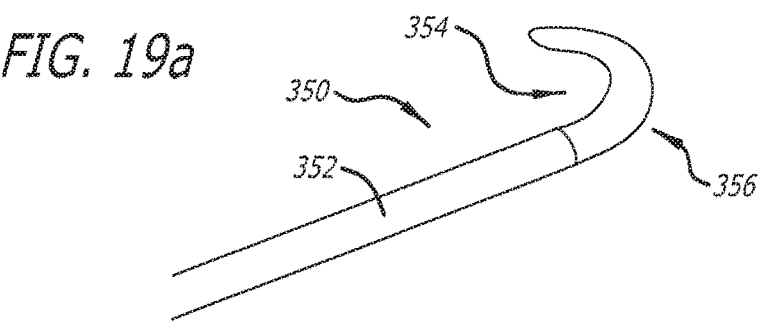
FIGS. 19a-b are perspective views of another approach to a probe device with a dilator.
Figure 19B:
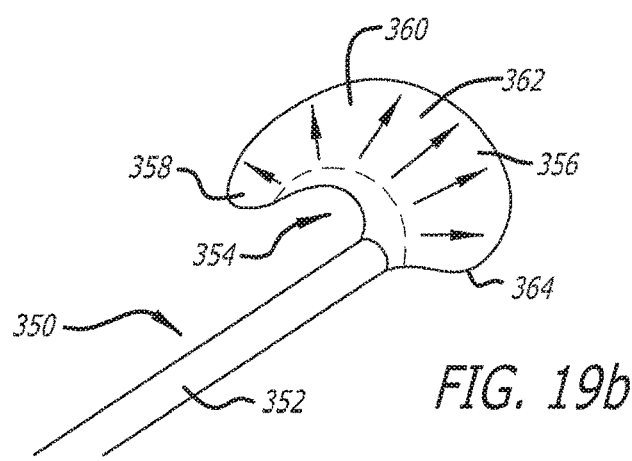

Turning now to FIGS. 19a and b, an alternative approach to a probe device 350 is shown. The device 350 includes a rigid or malleable shaft member 352 that terminates with an uncinate hook 354. A balloon 356 is configured about the hook 354 to provide a supported shape intended to maintain an access turn about an uncinate. Upon dilation, the balloon 356 forms a C-like shape, and anatomy at the interventional site is moved. For example, when placed into the sinuses, a terminal end 358 of the device 350 opens an infundibulum, an area 360 proximal the end 358 opens a supra-balloon space, a middle section 362 opens the middle meatus and a most proximal portion 364 of the balloon moves the middle turbinate. Thus, the device 350 can greatly and uniformly open the meatus and infundibulum to make easier the subsequent access the to the frontal, maxillary or ethmoid sinuses.

Figure 20:
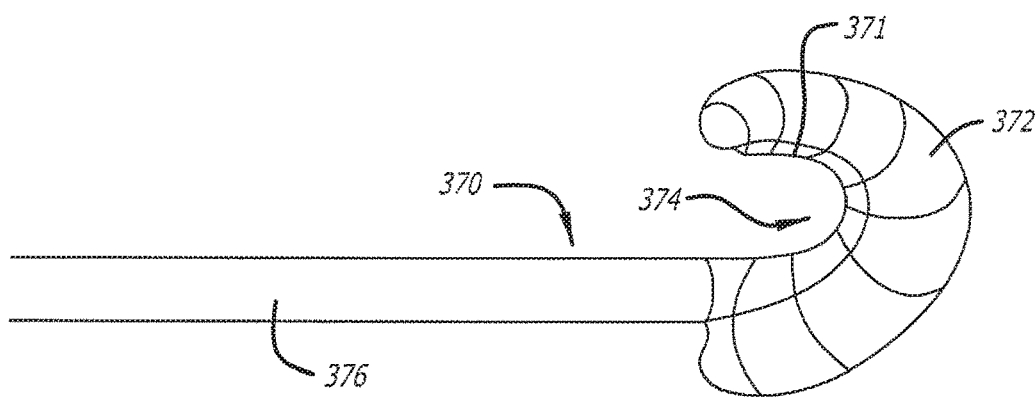
FIG. 20 is a side view of yet another embodiment of a probe device.

In a related device 370, and with reference now to FIG. 20, a balloon portion 372 is eccentrically located on a hook portion 374. The hook portion 374 can be either rigid or malleable. A shaft 376 is configured proximal to the balloon portion 372, and the device 370 can further include a tube 376 extending to a terminal end of the device, the tube 376 including an exit for a guidewire (not shown).

Figure 21:
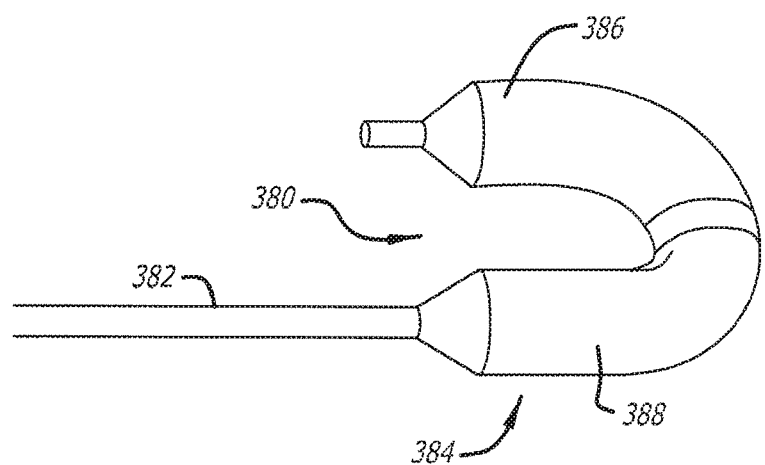
FIG. 21 is a perspective view of another approach to a probe device.
Figure 22:
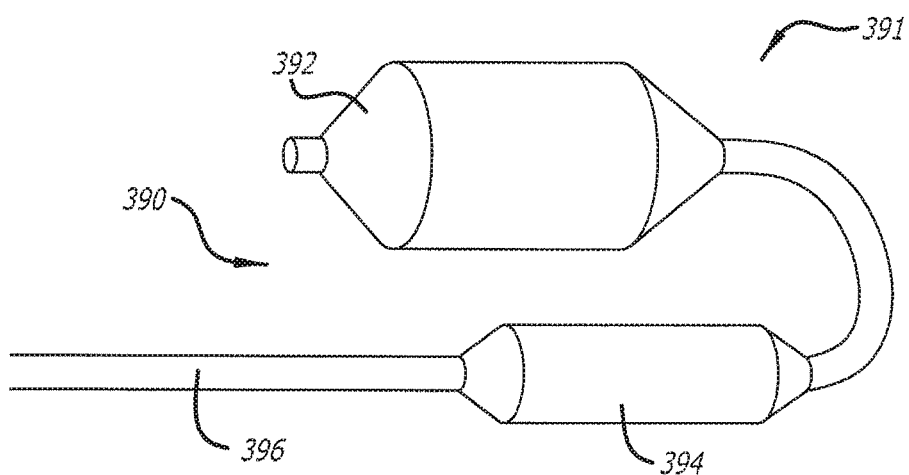
FIG. 22 is a perspective view of yet another approach to a probe device.

Yet further approaches to probe devices are depicted in FIGS. 21 and 22. In one embodiment, as shown in FIG. 21, a probe device 380 can embody a shaft 382 with a curved middle meatus/maxillary balloon 384 attached thereto. The balloon 384 includes a distal portion forming a maxillary region 386 and a proximal portion defining a middle meatus region 388. The balloon 384 is configured to have a built-in curve to turn about a patient's uncinate process.

In another embodiment, as shown in FIG. 22, a probe device 390 may include a shaft 396 and a balloon 391 having a maxillary region 392 embodying an increased diameter configured distally and about a curve from a meatus region 394. In either this or the previous embodiment, the maxillary region 392 and meatus region 394 of the balloon 391 may be formed from different balloon materials, with for example, the maxillary region 392 being more compliant. The two regions 392, 394 can further embody different shapes such as the maxillary side defining a dog-bone configuration. In this way, use of the probe devices 380, 390 accomplishes simultaneous dilation of both the maxillary and middle meatus regions, while protecting the uncinate from trauma. Also, the meatus balloon region 388, 394 of these devices can function to anchor the maxillary balloon region 386, 392 against sudden movement.

Figure 23:
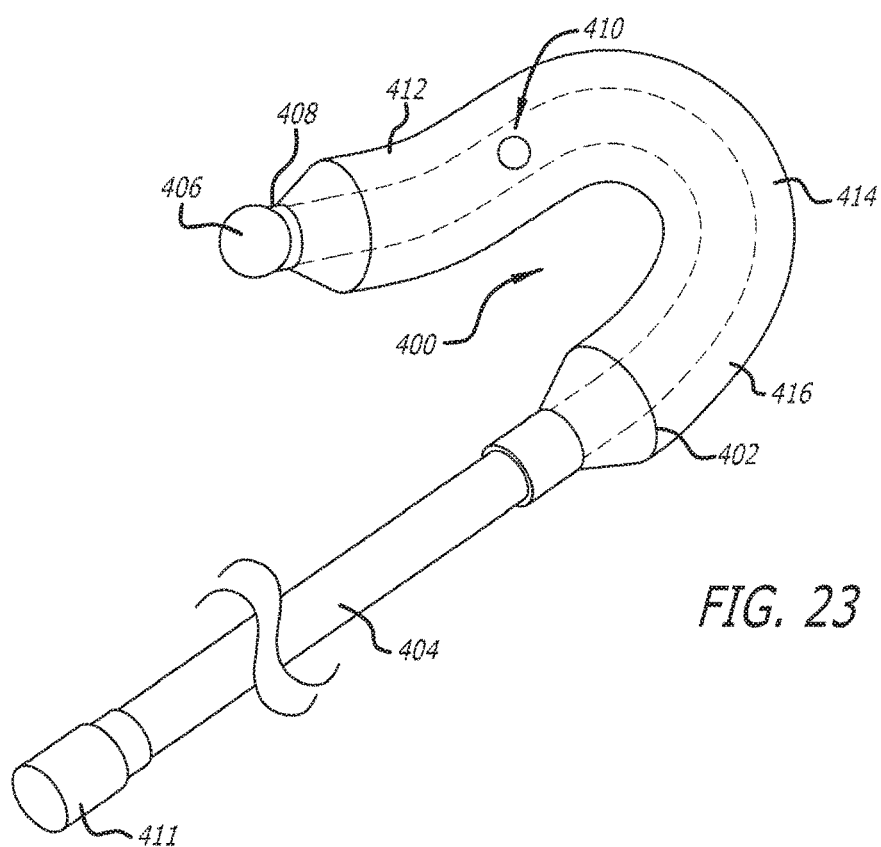
FIG. 23 is a partial cross-sectional view depicting another embodiment of a probe device.

Referring now to FIG. 23, in another embodiment, a transition space dilation tool 400 may include a balloon 402 attached about a distal portion of a semi rigid, rigid or malleable shaft 404. A distal end of the shaft 404 can be equipped with a ball-like atraumatic tip 406. The balloon 402 can be mechanically captured by a ball-shaft interface 408 to thereby minimize a neck region of the balloon 402. Moreover, the shaft 404 may include an inflatable lumen exit 410 for expanding the balloon 402, which may be pre-shaped into a hook. An inflation hub 411 may further be included to provide a dilation means.

The balloon 402 of this probe device 400 generally includes three regions: an infundibulum balloon region 412; a bullar balloon region 414; and a middle meatal balloon region 416. The infundibulum region 412 is configured to dilate infundibulum transitional space, the bullar region 414 compresses bulla to make room for scopes or other devices and the middle meatal region 416 opens meatal space to reduce potential trauma from subsequent device insertion. Each region may have different diameters or thicknesses and can define a myriad of shapes, angles and curves. Further, the shaft 404 can be single or multi-lumened, and the balloon can be compliant, semi-compliant or non-compliant.

Figure 24:
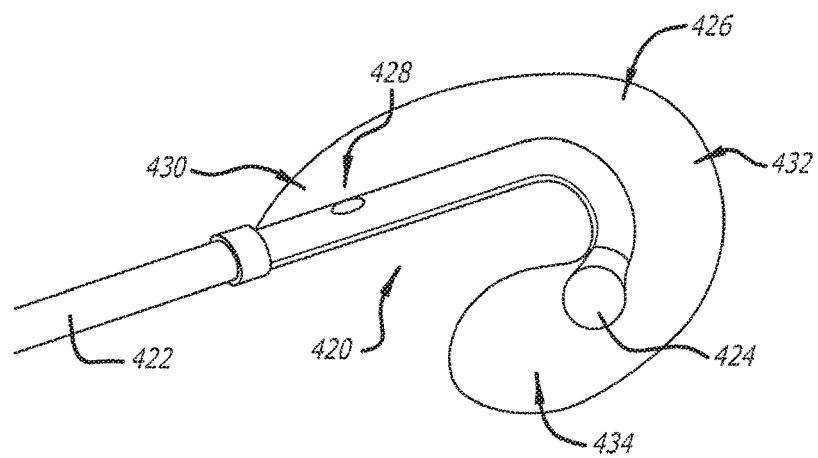
FIG. 24 is a partial cross-sectional view depicting another alternate embodiment of a probe device.

With reference now to FIG. 24, an infundibular meatal or recess-transition space dilator 420 may include a shaft 422 having a ball tip 424 and a curved distal portion surrounded by a balloon 426. An inflation opening 428 is provided in the shaft 422 region surrounded by the balloon 426 and notably, the ball tip 424 is encapsulated by the balloon 426. The balloon 426 further includes a middle turbinate region 430, a bullar region 432 and an infundibular region 434. The balloon can be molded with a closed end or can be traditionally molded and then the tip molded over and closed. As before, the balloon material can be non-elastic, partially elastic, compliant, non-compliant or partially compliant.

Figure 25:
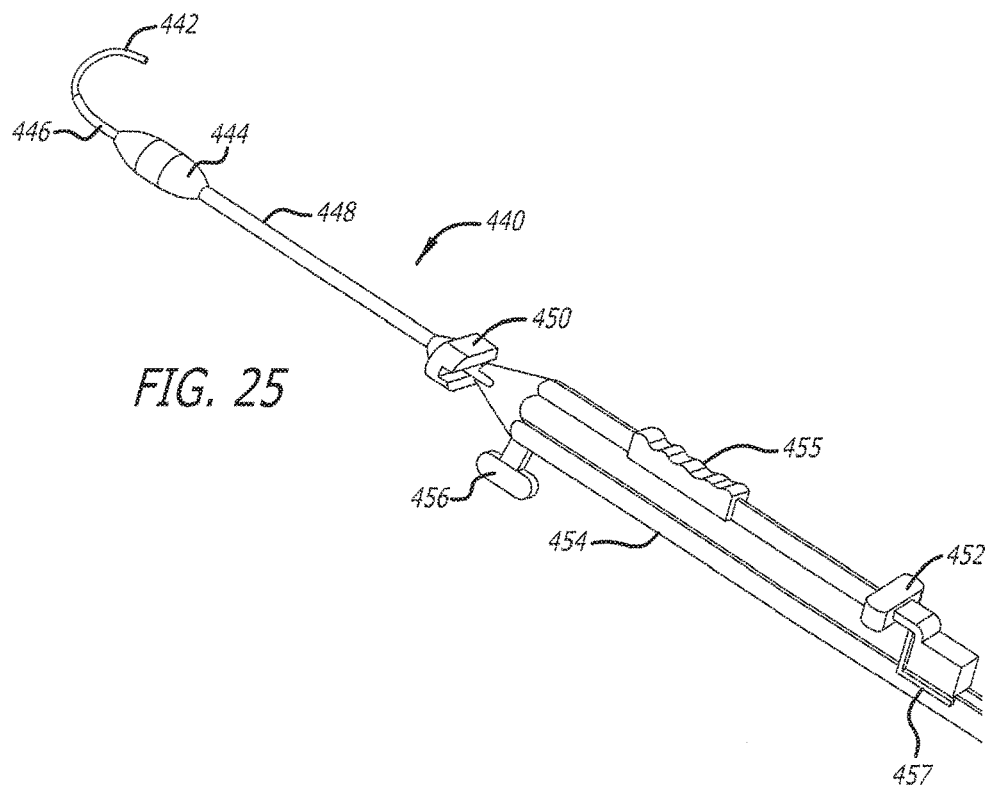
FIG. 25 is a perspective view depicting a probe device including details of a handle assembly.

In yet another approach, and with reference now to FIG. 25, a probe device 440 includes a separate internal element 442 that can be advanced and retracted to give tactile feedback to find a maxillary ostium. Once the maxillary ostium has been found, the user can independently advance a balloon portion 444 over a hypotube portion 446. The internal element 442 can be a wire or some other flexible element which can be extended out of the shaped hypotube 446 to probe for the sinus. In certain approaches, the internal element 442 can be coiled wire over a nitinol core, a solid flexible wire or plastic member, a light wire, or other flexible element. The shaped hypotube 446 can be formed from a steel or plastic tube that has a curve to direct the internal flexible member 442 and external balloon 444. In various embodiments, the tube can be pre-shaped for a specific sinus or malleable to allow the user to shape the device for a target trajectory.

The balloon 444 is configured about an outside of the shaped hypotube 446 and can be advanced independently of the internal element 442. A balloon shaft 448 is provided with one or two lumens to allow advancement of the balloon 444 and for inflation. The shaft 448 may extend over around the hypotube curve 446 or can start proximal the curve. A balloon pusher 450 is further provided to translate force from a balloon driver 452 to the balloon 444. This structure also may act as a manifold for fluid to fill/pressurize the balloon.

A probe handle 454 can be shaped to form an elongate structure and can be slender for easy holding and control. The handle 454 can further include a finger grip for assisting with traction for holding or advancing elements. The handle 454 also includes an internal element control 455 which slides within the handle 454 and allows the user to control advancing/retracting the internal element 442 as well as receiving tactile feedback from the internal element 442. The handle also includes a balloon driver 456 which slides within the handle 454 and allows user to advance/retract balloon. Rails 457 are further provided for guiding the movement of the internal control element 455 and push rods (not shown) connecting the balloon driver to the balloon pusher. In various alternative embodiments, balloon inflation fluid may be passed through one or both of the rails 457, if they are tubes, or alternatively, the probe device 440 may include one or more separate inflation lumens for delivering fluid/pressure to the balloon.

In certain circumstances, when attempting to access a maxillary sinus opening with a probe device including a shaping mandrel, it can be useful to have a mandrel with a very tight radius to send the probing end of the tip into the right place. It may also be useful to have the starting tip length itself be relatively short. The tip may need to have a finer selection end on the front. If the balloon catheter lumen itself is too large, bulky and/or stiff, it can pass by an ostium opening when advanced, without entering the opening, because the opening can be more like a hole in the side of the wall, and not necessarily at the end of an infundibular pocket. Further, even if the tip does momentarily engage the ostium, the stiffness of the balloon catheter can overpower it, and it will not enter the opening once the balloon is attempted to be advanced. Thus, a more flexible lead-in section that supports the balloon stiffness transition into the opening may be employed in some embodiments.

Figure 26:
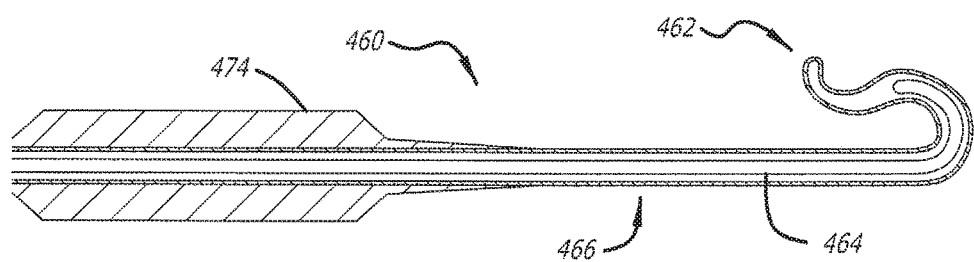
FIG. 26 is a partial cross-sectional view depicting a probe with a finder tip.

Turning now to FIG. 26, a probe device 460 having a small, short angled tip to select the side-hole ostium when that anatomy is present is described. This device includes a floppy lead-in catheter section that also has good column strength that permits advancement forward into an ostium to support the transition to the stiffer balloon. A nitinol super-elastic mandrel can be provided to form a very tight initial radius that maintains its shape as the floppy lead-in catheter is advanced but opens up as the stiffer balloon catheter is advanced.

As shown, the probe device 460 includes a finder tip 462, which could be shapeable or fixed and oriented outwardly to find an opening in a "wall" or infundibulum. The tip 462 could be made of a polymer or could be a wire tip. The probe device 460 can further embody a mandrel 464 formed from shape memory, super elastic, spring steel or other semi-rigid materials. This helps keep angles very tight when solely selecting with a flexible catheter. Moreover, the probe device 460 may include a flexible finder catheter body 464, which acts like a guidewire to track behind the tip 462 and acts to confirm access to the sinus by advancing without resistance.

Figure 27:
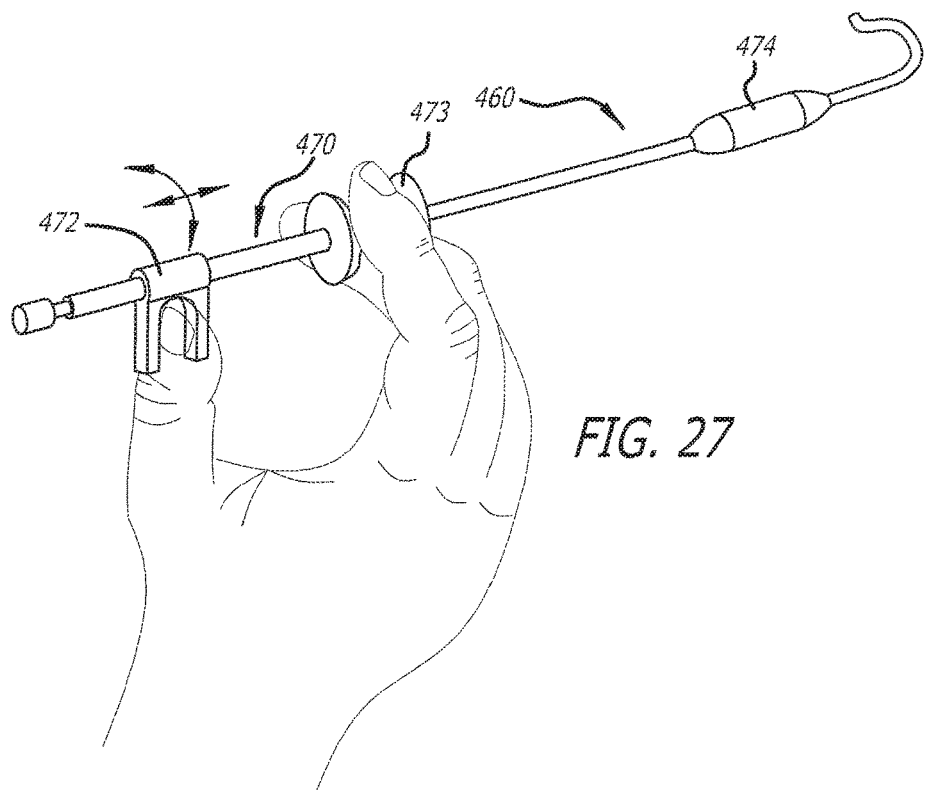
FIG. 27 is a perspective view of a handle for a probe device.

Referring now to FIG. 27, in one embodiment, a handle 470 for the probe device 460 may include a thumb pusher 472 operatively connected to the balloon portion 474 so that manipulation of the pusher 472 advances and/or retracts the balloon 474. The handle 470 may further include a stabilization substructure 473 sized and shaped to receive figures of an operator.

Figure 28A:
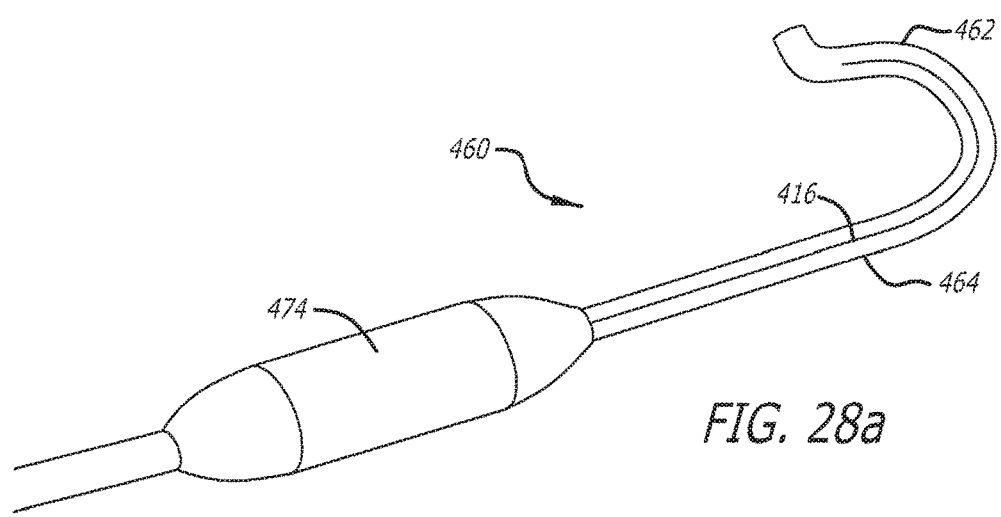
FIGS. 28a-c depict steps involved in a method of use of the device of FIG. 26.
Figure 28B:
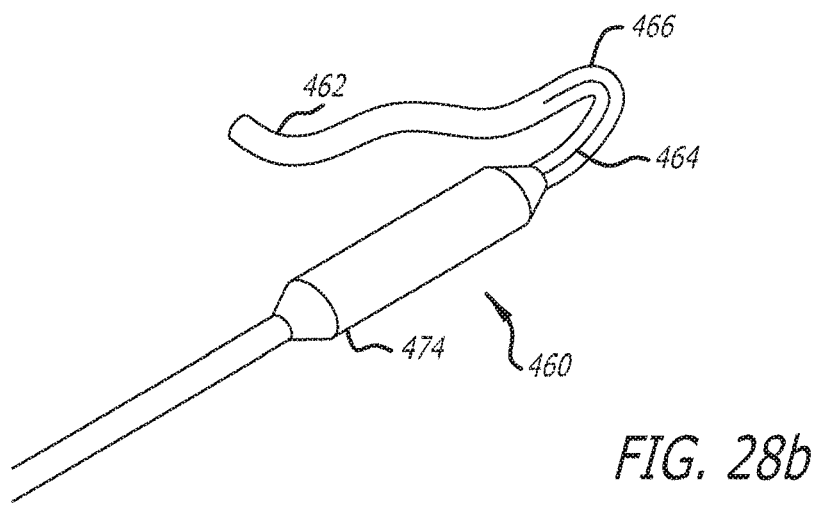
Figure 28C:
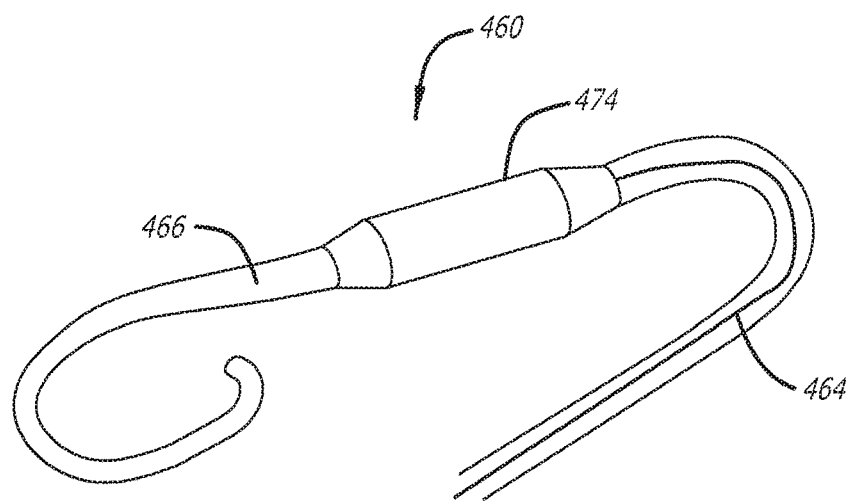

With reference now to FIGS. 28a-28c, in one embodiment of a method for using a probe device 460, the probe device 460 may be placed in a pre-deployment configuration (FIG. 28a), with the mandrel 464 loaded within the flexible catheter body 466. During mid-deployment (FIG. 28b), the mandrel 464 is withdrawn proximally, but is left to extend beyond the balloon portion 474. Next, the mandrel 464 is further withdrawn proximal the balloon 474 (FIG. 28c) to achieve complete deployment. The balloon 474 can then be expanded to create space or accomplish desired tissue manipulation.

The above description has often focused on embodiments of devices, systems and methods for use in maxillary paranasal sinuses. In some cases, however, the above-described embodiments may be used in procedures involving frontal, sphenoid and/or ethmoid sinuses. In some cases, these embodiments may be used as described in these other sinuses, while in other cases minor modifications may be made to the devices, systems or methods to make them more amenable to use in the frontal, sphenoid or ethmoid sinuses. In any event, the description above related to usage in the maxillary sinus should not be interpreted to limit the present invention to applications in only that sinus.

While the present invention has been described with reference to the specific embodiments thereof, various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An apparatus, comprising:
   (a) an elongated shaft, wherein the elongated shaft comprises:
      (i) a distal end,
      (ii) a proximal end,
      (iii) a curved region between the proximal and distal ends,
      (iv) an elongated tubular inner sheath, and
      (v) elongated tubular outer sheath, the inner sheath being positioned within the outer sheath;
   (b) a handle joined to the proximal end;
   (c) a longitudinal interior channel extending through the shaft and the handle;
   (d) an actuator element slidably mounted within a slot on the handle; and
   (e) an expandable dilator slidably disposed around a portion of an exterior of the elongate shaft; further comprising an extensible and retractable guidewire movably mounted within the interior channel; wherein the guide wire is reversibly movable between a retracted position and an extended position.

2. The apparatus of claim 1, further comprising a probe tip joined to an end of the guide wire, wherein the probe tip is configured to fit through a passageway in a paranasal cavity.

3. The apparatus of claim 2, wherein the probe tip is spherical.

4. The apparatus of claim 2, wherein the actuator element is mechanically coupled to the guide wire such that the guide wire is extensible and retractable according to adjustment of the actuator element relative to the handle.

5. The apparatus of claim 2, wherein the guide wire is reversibly movable between a retracted position and an extended position, wherein the probe tip is adjacent to the distal end of the elongated shaft at the retracted position, wherein the probe tip is separated from the distal end of the elongated shaft at the extended position.

6. The apparatus of claim 1, wherein the inner sheath is extensible and retractable with respect to the outer sheath.

7. The apparatus of claim 6, wherein the outer sheath includes a first slot and the inner sheath includes a second slot, wherein the first and second slots are structured and configured to allow the guide wire to be inserted into and removed from the interior channel through the first and second slots when the first and second slots are aligned with each other.

8. The apparatus of claim 1, wherein the shaft further comprises a longitudinal slot communicating with the longitudinal interior channel, wherein the longitudinal slot is structured and configured to allow the guide wire to be inserted into and removed from the interior channel through the longitudinal slot.

9. The apparatus of claim 1, wherein the shaft further comprises a front portion and a back portion joined to the front portion, the front and back portions defining a tubular shape, wherein the interior channel is located between the front and back portions.

10. The apparatus of claim 9, wherein the front portion further comprises a slot, the slot communicating with the interior channel, wherein the slot is structured and configured to allow the guide wire to be inserted into and removed from the interior channel through the slot.

11. The apparatus of claim 1, wherein the actuator element is operable to translate longitudinally relative to the handle to thereby extend and retract the guide wire.

12. The apparatus of claim 1, wherein the expandable dilator is slidably disposed about the guide wire.

13. The apparatus of claim 1, wherein the distal end of the elongated shaft is malleable.

14. An apparatus, comprising:
   (a) an elongated shaft, wherein the elongated shaft comprises:
      (i) a distal end,
      (ii) a proximal end,
      (iii) a curved region between the proximal and distal ends,
      (iv) an elongated tubular inner sheath, and
      (v) an elongated tubular outer sheath, wherein the inner sheath is positioned within the outer sheath, wherein the outer sheath includes a first slot and the inner sheath includes a second slot;
   (b) a handle joined to the proximal end;
   (c) a longitudinal interior channel extending through the shaft and the handle; and
   (d) an actuator element associated with the handle; further comprising an extensible and retractable guidewire movably mounted within the interior channel; wherein the first and second slots are structured and configured to allow the guide wire to be inserted into and removed from the interior channel through the first and second slots when the first and second slots are aligned with each other.

15. The apparatus of claim 14, further comprising a probe tip joined to an end of the guide wire, wherein the probe tip is configured to fit through a passageway in a paranasal cavity.

16. The apparatus of claim 14, wherein the actuator element is mechanically coupled to the guide wire such that the guide wire is extensible and retractable according to adjustment of the actuator element relative to the handle.

17. An apparatus, comprising:
   (a) an elongated shaft, wherein the elongated shaft comprises:
      (i) a distal end,
      (ii) a proximal end,
      (iii) a curved region between the proximal and distal ends,
      (iv) a front portion comprising a slot, and
      (v) a back portion joined to the front portion, the front and back portions defining a tubular shape;
   (b) a handle joined to the proximal end;
   (c) a longitudinal interior channel extending through the shaft and the handle, wherein the interior channel is located between the front portion and the back portion, the slot communicating with the interior channel; and
   (d) an actuator element associated with the handle; wherein the actuator element is mechanically coupled to a guide wire such that the guide wire is extensible and retractable according to adjustment of the actuator element relative to the handle.

\* \* \* \* \*